(12) United States Patent
Sokol et al.

(10) Patent No.: US 9,987,109 B2
(45) Date of Patent: Jun. 5, 2018

(54) MECHANICALLY-DRIVEN, SONIC TOOTHBRUSH AND WATER FLOSSER

(71) Applicant: WATER PIK, INC., Fort Collins, CO (US)

(72) Inventors: Gary L. Sokol, Longmont, CO (US); Harold A. Luettgen, Windsor, CO (US)

(73) Assignee: Water Pik, Inc., Fort Collins, CO (US)

( * ) Notice: Subject to any disclaimer, the term of this patent is extended or adjusted under 35 U.S.C. 154(b) by 239 days.

(21) Appl. No.: 14/216,779

(22) Filed: Mar. 17, 2014

(65) Prior Publication Data

US 2014/0259474 A1 Sep. 18, 2014

Related U.S. Application Data

(60) Provisional application No. 61/802,121, filed on Mar. 15, 2013.

(51) Int. Cl.
*A61C 17/36* (2006.01)
*A61C 17/02* (2006.01)
(Continued)

(52) U.S. Cl.
CPC .......... *A61C 17/36* (2013.01); *A61C 17/0202* (2013.01); *A61C 17/3418* (2013.01); *A61C 17/0205* (2013.01); *A61C 17/222* (2013.01)

(58) Field of Classification Search
CPC ......... A46B 13/04; A61C 17/00; A61C 17/02; A61C 17/0202; A61C 17/0214;
(Continued)

(56) References Cited

U.S. PATENT DOCUMENTS

| 669,402 A | 3/1901 | Rose |
|---|---|---|
| 684,951 A | 10/1901 | Rothkranz |

(Continued)

FOREIGN PATENT DOCUMENTS

| CH | 435553 | 10/1967 |
|---|---|---|
| CH | 502817 A | 2/1971 |

(Continued)

OTHER PUBLICATIONS

Sonex International: Brushing with the Ultima—The World's Only Dual-Frequency Ultrasonic Toothbrush, Jul. 28, 1999, published at Sonipic.com.

(Continued)

*Primary Examiner* — Mark Spisich
(74) *Attorney, Agent, or Firm* — Dorsey & Whitney LLP

(57) ABSTRACT

A sonic toothbrush system including an electric motor, a brush shaft, a drive assembly, a fluid conduit connected to a pressurized, pulsed water source, and a water jet nozzle positioned on the brush head and connected to the fluid conduit. The electric motor includes a drive shaft. When the electric motor is caused to operate, the drive shaft continuously rotates until the motor is caused to stop. The drive assembly is coupled between the drive shaft and brush shaft. The drive assembly is configured to convert the rotation of the drive shaft into sonic oscillation of a toothbrush supported on an end of the brush shaft. The drive assembly further forms part of the fluid conduit to deliver a pulsed water stream to the jet nozzle.

22 Claims, 38 Drawing Sheets

(51) Int. Cl.
   *A61C 17/34*  (2006.01)
   *A61C 17/22*  (2006.01)

(58) Field of Classification Search
   CPC ....... A61C 17/028; A61C 17/16; A61C 17/20;
            A61C 17/22; A61C 17/227; A61C 17/32;
            A61C 17/34; A61C 17/3409; A61C
            17/3418; A61C 17/3481; A61C 17/36;
            A61C 17/224; A61C 17/28
   USPC .... 15/22.1, 22.2, 24, 29; 433/80, 82, 84–86,
                            433/88, 89; 601/162, 165
   See application file for complete search history.

(56) References Cited

U.S. PATENT DOCUMENTS

| | | |
|---|---|---|
| 914,501 A | 3/1909 | McEachern |
| 933,718 A | 9/1909 | Mahoney |
| 958,371 A | 5/1910 | Danek |
| 1,018,927 A | 2/1912 | Sarrazin |
| 1,033,819 A | 7/1912 | McMann |
| 1,059,426 A | 4/1913 | Barnes |
| D45,199 S | 2/1914 | McDonagh et al. |
| D45,572 S | 4/1914 | Sarrazin |
| 1,128,139 A | 2/1915 | Hoffman |
| D49,472 S | 8/1916 | Dierke |
| 1,251,250 A | 12/1917 | Libby |
| 1,268,544 A | 6/1918 | Cates |
| 1,278,225 A | 9/1918 | Schamberg |
| 1,296,067 A | 3/1919 | Fuller |
| D53,453 S | 7/1919 | Lloyd |
| 1,313,490 A | 8/1919 | Larson |
| 1,337,173 A | 4/1920 | White |
| 1,355,037 A | 10/1920 | Dziuk |
| D57,327 S | 3/1921 | Gibson |
| 1,382,681 A | 6/1921 | Segal |
| 1,424,879 A | 8/1922 | Carlstedt |
| 1,440,785 A | 1/1923 | Levis |
| 1,452,258 A | 4/1923 | Smith |
| 1,456,535 A | 5/1923 | Cartwright |
| 1,480,310 A | 1/1924 | Smith |
| 1,488,214 A | 3/1924 | Mason |
| 1,494,448 A | 5/1924 | Sookne |
| 1,497,495 A | 6/1924 | Fincke |
| 1,517,320 A | 12/1924 | Stoddart |
| 1,527,853 A | 2/1925 | Ferdon |
| 1,588,785 A | 6/1926 | Van Sant |
| 1,639,880 A | 8/1927 | Butler |
| 1,657,450 A | 1/1928 | Barnes |
| 1,676,703 A | 7/1928 | Nuyts |
| 1,696,835 A | 12/1928 | Burnett |
| 1,703,642 A | 2/1929 | Sticht |
| 1,794,711 A | 3/1931 | Jacobs |
| 1,796,641 A | 3/1931 | Zimmerman et al. |
| 1,800,993 A | 4/1931 | Funk |
| 1,832,519 A | 11/1931 | Wheat et al. |
| 1,880,617 A | 10/1932 | White |
| 1,916,641 A | 7/1933 | Seeliger |
| 1,927,365 A | 9/1933 | Frolio |
| 1,940,111 A | 12/1933 | Austin |
| 1,943,225 A | 1/1934 | McIntyre |
| D93,019 S | 8/1934 | Hose |
| 1,977,782 A | 10/1934 | Roy |
| 1,992,770 A | 2/1935 | Rathbun |
| 2,016,597 A | 10/1935 | Drake |
| 2,016,644 A | 10/1935 | Luball |
| 2,042,239 A | 5/1936 | Planding |
| 2,044,863 A | 6/1936 | Sticht |
| D101,080 S | 9/1936 | Cosad |
| 2,114,947 A | 4/1938 | Warsaw |
| D113,743 S | 3/1939 | Kahn |
| D113,744 S | 3/1939 | Kahn |
| 2,158,738 A | 5/1939 | Baker et al. |
| 2,168,964 A | 8/1939 | Strasser |
| 2,206,726 A | 7/1940 | Lasater |
| 2,209,173 A | 7/1940 | Russell |
| 2,218,072 A | 10/1940 | Runnels |
| 2,226,663 A | 12/1940 | Hill et al. |
| 2,244,098 A | 6/1941 | Busick |
| 2,246,523 A | 6/1941 | Kulik |
| 2,273,717 A | 2/1942 | Millard et al. |
| 2,278,365 A | 3/1942 | Daniels |
| 2,279,355 A | 4/1942 | Wilensky |
| 2,282,700 A | 5/1942 | Bobbroff |
| 2,312,828 A | 3/1943 | Adamsson |
| D136,156 S | 8/1943 | Fuller |
| D139,532 S | 11/1944 | Trecek |
| D141,350 S | 5/1945 | Alexander et al. |
| D144,163 S | 3/1946 | Dolnick |
| 2,401,186 A | 5/1946 | Price |
| 2,405,029 A | 7/1946 | Gallanty et al. |
| D146,271 S | 1/1947 | Stavely |
| 2,414,775 A | 1/1947 | Stavely |
| 2,429,740 A | 10/1947 | Aufsesser |
| 2,450,635 A | 10/1948 | Dembenski |
| D154,598 S | 7/1949 | Gass |
| D155,668 S | 10/1949 | Zandberg et al. |
| D157,669 S | 3/1950 | Graves, Jr. |
| D159,872 S | 8/1950 | Skold |
| D160,101 S | 9/1950 | MacDonald |
| 2,531,730 A | 11/1950 | Henderson |
| 2,533,345 A | 12/1950 | Bennett |
| 2,543,999 A | 3/1951 | Voss |
| D163,707 S | 6/1951 | Pifer |
| 2,558,332 A | 6/1951 | Artale |
| 2,567,080 A | 9/1951 | Pifer |
| 2,577,597 A | 12/1951 | Wright et al. |
| 2,583,750 A | 1/1952 | Runnels |
| 2,595,666 A | 5/1952 | Hutson |
| 2,598,275 A | 5/1952 | Lakin |
| 2,618,003 A | 11/1952 | Robey |
| D169,131 S | 3/1953 | Fay |
| 2,651,068 A | 9/1953 | Seko |
| D170,680 S | 10/1953 | Del Mas |
| D172,693 S | 7/1954 | Wibbelsman et al. |
| D173,616 S | 12/1954 | Hernandez |
| 2,705,335 A | 4/1955 | Glassman et al. |
| 2,709,227 A | 5/1955 | Foley et al. |
| 2,722,703 A | 11/1955 | Green |
| 2,728,928 A | 1/1956 | Beeren |
| 2,734,139 A | 2/1956 | Murphy |
| 2,806,235 A | 9/1957 | Carstairs et al. |
| 2,819,482 A | 1/1958 | Applegate |
| 2,868,215 A | 1/1959 | Mechem |
| 2,875,458 A | 3/1959 | Tsuda |
| 2,917,758 A | 12/1959 | Held et al. |
| 2,931,371 A | 4/1960 | Petitta |
| 2,946,072 A | 7/1960 | Filler et al. |
| 2,962,033 A | 11/1960 | Lew |
| 2,977,614 A | 4/1961 | Demanuele |
| 2,977,682 A | 4/1961 | Flatray |
| 3,103,027 A | 9/1963 | Birch |
| 3,104,405 A | 9/1963 | Perrinjaquet |
| 3,106,216 A | 10/1963 | Kirby |
| D197,048 S | 12/1963 | Troy |
| D197,208 S | 12/1963 | Cassidy et al. |
| 3,143,697 A | 8/1964 | Springer |
| 3,145,404 A | 8/1964 | Fiedler |
| D199,560 S | 11/1964 | Thompson |
| D199,893 S | 12/1964 | Bond et al. |
| 3,159,859 A | 12/1964 | Rasmussen |
| 3,160,902 A | 12/1964 | Aymar |
| 3,168,834 A | 2/1965 | Smithson |
| 3,181,189 A | 5/1965 | Leyden |
| 3,183,538 A | 5/1965 | Hubner |
| 3,195,537 A | 7/1965 | Blasi |
| D202,041 S | 8/1965 | Burzlaff |
| D202,873 S | 11/1965 | Husted |
| 3,220,039 A | 11/1965 | Dayton et al. |
| 3,229,318 A | 1/1966 | Clemens |
| 3,230,562 A | 1/1966 | Birch |
| D204,127 S | 3/1966 | Syvertson |
| 3,258,805 A | 7/1966 | Rossnan |
| 3,270,416 A | 9/1966 | Massa |

(56) References Cited

U.S. PATENT DOCUMENTS

| | | |
|---|---|---|
| 3,278,963 A | 10/1966 | Bond |
| 3,289,681 A | 12/1966 | Chambers |
| 3,311,116 A | 3/1967 | Foster |
| 3,316,576 A | 5/1967 | Urbrush |
| 3,335,443 A | 8/1967 | Parisi et al. |
| 3,346,748 A | 10/1967 | McNair |
| 3,358,309 A | 12/1967 | Richardson |
| 3,358,314 A | 12/1967 | Matibag |
| 3,359,588 A | 12/1967 | Kobler |
| D210,018 S | 1/1968 | Mattingly et al. |
| D210,019 S | 1/1968 | Johnson et al. |
| 3,364,576 A | 1/1968 | Kern, Jr. |
| D210,066 S | 2/1968 | Johnson |
| 3,369,265 A | 2/1968 | Halberstadt et al. |
| 3,371,260 A | 2/1968 | Jackson et al. |
| D210,349 S | 3/1968 | Boldt |
| 3,375,820 A | 4/1968 | Kuris et al. |
| 3,393,673 A | 7/1968 | Mattingly et al. |
| 3,394,277 A | 7/1968 | Satkunas et al. |
| D212,208 S | 9/1968 | Rogers |
| 3,418,552 A | 12/1968 | Holmes |
| 3,421,524 A | 1/1969 | Waters |
| 3,430,279 A | 3/1969 | Hintze |
| 3,463,994 A | 8/1969 | Spohr |
| 3,466,689 A | 9/1969 | Aurelio et al. |
| 3,472,045 A | 10/1969 | Nelsen et al. |
| 3,472,247 A | 10/1969 | Borsum et al. |
| 3,474,799 A | 10/1969 | Cappello |
| D215,920 S | 11/1969 | McCarty et al. |
| 3,495,587 A | 2/1970 | Freedman |
| 3,509,874 A | 5/1970 | Stillman |
| 3,535,726 A | 10/1970 | Sawyer |
| 3,536,065 A | 10/1970 | Moret |
| 3,538,359 A | 11/1970 | Barowski |
| 3,552,022 A | 1/1971 | Axelsson |
| 3,559,292 A | 2/1971 | Weissman |
| 3,563,233 A | 2/1971 | Bodine |
| D220,334 S | 3/1971 | Mackay et al. |
| 3,570,525 A | 3/1971 | Borsum |
| D220,996 S | 6/1971 | Irons |
| 3,588,936 A | 6/1971 | Duve |
| 3,590,814 A | 7/1971 | Bennett et al. |
| D221,823 S | 9/1971 | Cook |
| 3,608,548 A | 9/1971 | Lewis |
| D222,862 S | 1/1972 | Cook |
| 3,638,264 A * | 2/1972 | Walton .............. A46B 13/04 15/29 |
| 3,642,344 A | 2/1972 | Corker |
| 3,651,576 A | 3/1972 | Massa |
| 3,660,902 A | 5/1972 | Axelsson |
| 3,667,483 A | 6/1972 | McCabe |
| 3,672,378 A | 6/1972 | Silverman |
| 3,676,218 A | 7/1972 | Sawyer |
| 3,685,080 A | 8/1972 | Hubner |
| 3,722,020 A | 3/1973 | Hills |
| 3,742,549 A | 7/1973 | Scopp et al. |
| 3,759,274 A | 9/1973 | Warner |
| 3,760,799 A | 9/1973 | Crowson |
| 3,792,504 A | 2/1974 | Smith |
| 3,809,506 A | 5/1974 | Malcosky |
| 3,809,977 A | 5/1974 | Balamuth et al. |
| 3,811,432 A | 5/1974 | Moret |
| 3,831,611 A | 8/1974 | Hendricks |
| 3,837,166 A | 9/1974 | Hiraoka |
| 3,840,932 A | 10/1974 | Balamuth et al. |
| 3,847,167 A | 11/1974 | Brien |
| 3,851,984 A | 12/1974 | Crippa |
| 3,863,628 A | 2/1975 | Vit |
| D234,518 S | 3/1975 | Gerlich |
| 3,871,560 A | 3/1975 | Crippa |
| 3,882,364 A | 5/1975 | Wright et al. |
| 3,902,510 A | 9/1975 | Roth |
| 3,903,601 A | 9/1975 | Anderson et al. |
| 3,939,599 A | 2/1976 | Henry et al. |
| 3,959,883 A | 6/1976 | Walls et al. |
| 3,967,617 A | 7/1976 | Krolik |
| 3,973,558 A | 8/1976 | Stouffer et al. |
| 3,977,084 A * | 8/1976 | Sloan .................. A61C 17/005 15/29 |
| 3,978,852 A | 9/1976 | Annoni |
| 3,980,906 A | 9/1976 | Kuris et al. |
| 4,004,344 A | 1/1977 | Gold et al. |
| 4,005,722 A | 2/1977 | Bragg |
| 4,008,728 A | 2/1977 | Sanchez |
| 4,010,509 A | 3/1977 | Huish |
| 4,013,227 A | 3/1977 | Herrera |
| 4,014,354 A | 3/1977 | Garrett |
| 4,019,522 A | 4/1977 | Elbreder |
| 4,033,008 A | 7/1977 | Warren et al. |
| 4,048,723 A | 9/1977 | Thorup |
| 4,051,571 A | 10/1977 | Ayers |
| D246,668 S | 12/1977 | Mackay et al. |
| 4,064,883 A | 12/1977 | Oldham |
| 4,094,311 A | 6/1978 | Hudson |
| 4,133,339 A | 1/1979 | Naslund |
| 4,141,352 A | 2/1979 | Ebner et al. |
| 4,156,620 A | 5/1979 | Clemens |
| 4,171,572 A | 10/1979 | Nash |
| 4,173,828 A * | 11/1979 | Lustig .................. A61C 1/07 15/28 |
| 4,177,434 A | 12/1979 | Ida |
| D254,162 S | 2/1980 | Barker |
| 4,192,035 A | 3/1980 | Kuris |
| 4,200,235 A | 4/1980 | Monschke |
| 4,203,431 A | 5/1980 | Abura et al. |
| 4,205,664 A | 6/1980 | Baccialon |
| 4,219,619 A | 8/1980 | Zarow |
| 4,235,253 A | 11/1980 | Moore |
| 4,245,658 A | 1/1981 | Lecouturier |
| D258,097 S | 2/1981 | Wistrand |
| RE30,536 E | 3/1981 | Perdreaux, Jr. |
| 4,255,693 A | 3/1981 | Keidl |
| 4,265,257 A | 5/1981 | Salyer |
| 4,268,933 A | 5/1981 | Papas |
| 4,271,382 A | 6/1981 | Maeda et al. |
| 4,271,384 A | 6/1981 | Beiling et al. |
| 4,271,854 A | 6/1981 | Bengtsson |
| 4,275,363 A | 6/1981 | Mishiro et al. |
| 4,288,883 A | 9/1981 | Dolinsky |
| 4,289,486 A | 9/1981 | Sargeant |
| 4,303,064 A | 12/1981 | Buffa |
| 4,306,862 A | 12/1981 | Knox |
| 4,307,740 A | 12/1981 | Florindez et al. |
| 4,319,377 A | 3/1982 | Tarrson et al. |
| 4,319,595 A | 3/1982 | Ulrich |
| 4,326,547 A | 4/1982 | Verplank |
| 4,326,548 A | 4/1982 | Wagner |
| 4,326,549 A | 4/1982 | Hinding |
| 4,331,422 A | 5/1982 | Heyman |
| 4,333,197 A | 6/1982 | Kuris |
| 4,336,622 A | 6/1982 | Teague, Jr. et al. |
| D265,515 S | 7/1982 | Levine |
| 4,338,957 A | 7/1982 | Meibauer |
| D265,698 S | 8/1982 | Roth |
| 4,346,492 A | 8/1982 | Solow |
| 4,347,839 A | 9/1982 | Youngclaus, Jr. |
| 4,353,141 A | 10/1982 | Teague, Jr. et al. |
| 4,356,585 A | 11/1982 | Protell et al. |
| 4,381,478 A | 4/1983 | Saijo et al. |
| 4,395,665 A | 7/1983 | Buchas |
| 4,397,327 A | 8/1983 | Hadary |
| D270,972 S | 10/1983 | Rosofsky |
| 4,416,628 A | 11/1983 | Cammack |
| D272,565 S | 2/1984 | Levine |
| D272,680 S | 2/1984 | Stocchi |
| 4,429,997 A | 2/1984 | Matthews |
| 4,432,729 A | 2/1984 | Fattaleh |
| 4,434,806 A | 3/1984 | Givens |
| 4,442,830 A | 4/1984 | Markau |
| D274,018 S | 5/1984 | Usui |
| 4,450,599 A | 5/1984 | Scheller et al. |
| 4,455,704 A | 6/1984 | Williams |
| 4,458,702 A | 7/1984 | Grollimund |
| 4,488,327 A | 12/1984 | Snider |

(56) References Cited

U.S. PATENT DOCUMENTS

| | | |
|---|---|---|
| 4,490,114 A | 12/1984 | Kleesattel |
| 4,505,678 A | 3/1985 | Andersson |
| 4,517,701 A | 5/1985 | Stanford, Jr. |
| 4,519,111 A | 5/1985 | Cavazza |
| 4,522,355 A | 6/1985 | Moran |
| 4,522,595 A | 6/1985 | Selvidge |
| 4,543,679 A | 10/1985 | Rosofsky et al. |
| D281,202 S | 11/1985 | Thompson |
| 4,561,214 A | 12/1985 | Inoue |
| 4,562,413 A | 12/1985 | Mishiro et al. |
| 4,564,794 A | 1/1986 | Kilen et al. |
| 4,571,768 A | 2/1986 | Kawashima |
| 4,576,190 A | 3/1986 | Youssef |
| 4,577,649 A | 3/1986 | Shimenkov |
| 4,578,033 A | 3/1986 | Mossle et al. |
| D283,374 S | 4/1986 | Cheuk-Yiu |
| 4,585,415 A | 4/1986 | Hommann |
| 4,586,521 A | 5/1986 | Urso |
| D284,236 S | 6/1986 | Collet |
| D284,528 S | 7/1986 | Jurado |
| 4,603,448 A | 8/1986 | Middleton et al. |
| 4,605,025 A | 8/1986 | McSpadden |
| 4,608,019 A | 8/1986 | Kumabe et al. |
| 4,610,043 A | 9/1986 | Vezjak |
| 4,617,695 A | 10/1986 | Amos et al. |
| 4,617,718 A | 10/1986 | Andersson |
| 4,619,009 A * | 10/1986 | Rosenstatter .......... A61C 17/28 15/29 |
| D287,073 S | 12/1986 | Thompson |
| 4,634,376 A | 1/1987 | Mossle et al. |
| 4,644,937 A | 2/1987 | Hommann |
| 4,655,198 A | 4/1987 | Hommann |
| 4,672,706 A | 6/1987 | Hill |
| D292,448 S | 10/1987 | Vianello |
| 4,698,869 A | 10/1987 | Mierau et al. |
| 4,706,322 A | 11/1987 | Nicolas |
| 4,706,695 A | 11/1987 | Urso |
| D294,885 S | 3/1988 | Mollenhoff |
| 4,729,142 A | 3/1988 | Yoshioka |
| D297,467 S | 8/1988 | McCann |
| 4,766,630 A | 8/1988 | Hegemann |
| 4,776,054 A | 10/1988 | Rauch |
| D298,565 S | 11/1988 | Kohler, Jr. et al. |
| 4,787,847 A | 11/1988 | Martin et al. |
| 4,791,940 A | 12/1988 | Hirshfeld et al. |
| 4,800,608 A | 1/1989 | Key |
| 4,802,255 A | 2/1989 | Breuer et al. |
| 4,811,445 A | 3/1989 | Lagieski et al. |
| 4,820,153 A | 4/1989 | Romhild et al. |
| 4,820,154 A | 4/1989 | Romhild et al. |
| 4,827,550 A | 5/1989 | Graham et al. |
| 4,827,551 A * | 5/1989 | Maser .................... A61H 13/00 15/24 |
| 4,827,552 A | 5/1989 | Bojar et al. |
| 4,832,063 A | 5/1989 | Smole |
| D301,770 S | 6/1989 | Bethany |
| 4,844,104 A | 7/1989 | Martin |
| 4,845,795 A | 7/1989 | Crawford et al. |
| 4,856,133 A | 8/1989 | Sanchez |
| 4,864,676 A | 9/1989 | Schaiper |
| D303,876 S | 10/1989 | Clemens et al. |
| 4,871,396 A | 10/1989 | Tsujita et al. |
| 4,873,496 A | 10/1989 | Ohgihara et al. |
| 4,875,265 A | 10/1989 | Yoshida |
| 4,877,934 A | 10/1989 | Spinello |
| 4,879,781 A | 11/1989 | Desimone |
| 4,880,382 A | 11/1989 | Moret et al. |
| 4,887,052 A | 12/1989 | Murakami et al. |
| 4,892,191 A | 1/1990 | Nakamura |
| 4,908,902 A | 3/1990 | McNab et al. |
| 4,913,133 A | 4/1990 | Tichy |
| 4,913,176 A | 4/1990 | DeNiro |
| 4,915,304 A | 4/1990 | Campani |
| 4,922,936 A | 5/1990 | Buzzi et al. |
| D308,765 S | 6/1990 | Johnson |
| 4,973,246 A | 11/1990 | Black |
| 4,974,278 A | 12/1990 | Hommann |
| 4,984,173 A | 1/1991 | Imam et al. |
| 4,989,287 A | 2/1991 | Scherer |
| 4,991,249 A | 2/1991 | Suroff |
| 4,995,403 A | 2/1991 | Beckman et al. |
| 5,000,684 A | 3/1991 | Odrich |
| 5,002,487 A | 3/1991 | Tichy |
| 5,007,127 A | 4/1991 | Paolo |
| 5,016,660 A | 5/1991 | Boggs |
| 5,020,179 A | 6/1991 | Scherer |
| 5,033,150 A | 7/1991 | Gross et al. |
| D318,918 S | 8/1991 | Hartwein |
| D319,363 S | 8/1991 | Uemura et al. |
| 5,046,212 A | 9/1991 | O'Conke |
| 5,050,625 A | 9/1991 | Siekmann |
| 5,054,149 A | 10/1991 | Si-Hoe et al. |
| 5,061,180 A | 10/1991 | Wiele |
| D321,285 S | 11/1991 | Hirabayashi |
| 5,062,797 A | 11/1991 | Gonser |
| 5,067,223 A | 11/1991 | Bruno |
| D321,986 S | 12/1991 | Snyder et al. |
| 5,068,939 A | 12/1991 | Holland |
| 5,069,233 A | 12/1991 | Ritter |
| 5,069,621 A | 12/1991 | Paradis |
| 5,071,348 A | 12/1991 | Woog |
| 5,072,477 A | 12/1991 | Pai |
| 5,072,482 A | 12/1991 | Bojar et al. |
| 5,077,855 A | 1/1992 | Ambasz |
| 5,085,236 A | 2/1992 | Odneal et al. |
| 5,088,145 A | 2/1992 | Whitefield |
| D324,957 S | 3/1992 | Piano |
| 5,094,256 A | 3/1992 | Barth |
| 5,095,470 A | 3/1992 | Oka et al. |
| 5,100,319 A | 3/1992 | Baum |
| 5,100,321 A | 3/1992 | Coss et al. |
| 5,120,225 A | 6/1992 | Amit |
| 5,123,841 A | 6/1992 | Millner |
| 5,125,837 A | 6/1992 | Warrin et al. |
| 5,133,661 A | 7/1992 | Euvrard |
| 5,138,733 A | 8/1992 | Bock |
| 5,145,369 A | 9/1992 | Lustig et al. |
| 5,146,643 A | 9/1992 | Bojar et al. |
| 5,150,492 A | 9/1992 | Suroff |
| 5,151,030 A | 9/1992 | Comeaux |
| D330,116 S | 10/1992 | Crawford et al. |
| D330,286 S | 10/1992 | Curtis et al. |
| D330,458 S | 10/1992 | Curtis et al. |
| 5,152,394 A | 10/1992 | Hughes |
| 5,163,375 A | 11/1992 | Withers et al. |
| 5,165,131 A | 11/1992 | Suroff |
| 5,167,193 A | 12/1992 | Withers et al. |
| 5,169,313 A | 12/1992 | Kline |
| 5,170,809 A | 12/1992 | Imai et al. |
| 5,174,314 A | 12/1992 | Charatan |
| 5,176,157 A | 1/1993 | Mazza |
| 5,177,826 A | 1/1993 | Vrignaud et al. |
| 5,180,363 A | 1/1993 | Idemoto et al. |
| D332,873 S | 2/1993 | Hall |
| 5,183,063 A | 2/1993 | Ringle et al. |
| 5,183,156 A | 2/1993 | Bruno |
| 5,184,368 A | 2/1993 | Holland |
| 5,184,632 A | 2/1993 | Gross et al. |
| 5,186,191 A | 2/1993 | Loubier |
| 5,188,133 A | 2/1993 | Romanus |
| 5,189,751 A | 3/1993 | Giuliani et al. |
| 5,193,678 A | 3/1993 | Janocik et al. |
| 5,198,732 A | 3/1993 | Morimoto |
| D334,472 S | 4/1993 | Curtis et al. |
| 5,201,092 A | 4/1993 | Colson |
| D335,579 S | 5/1993 | Chuang |
| 5,207,773 A | 5/1993 | Henderson |
| 5,213,434 A | 5/1993 | Hahn |
| 5,214,819 A | 6/1993 | Kirchner |
| 5,217,031 A | 6/1993 | Santoro |
| 5,224,500 A | 7/1993 | Stella |
| 5,226,206 A | 7/1993 | Davidovitz et al. |
| 5,236,358 A | 8/1993 | Sieffert |
| 5,245,117 A | 9/1993 | Withers et al. |

(56) References Cited

U.S. PATENT DOCUMENTS

| | | | |
|---|---|---|---|
| 5,246,022 A | 9/1993 | Israel et al. | |
| 5,247,716 A | 9/1993 | Bock | |
| 5,253,382 A | 10/1993 | Beny | |
| 5,261,430 A | 11/1993 | Mochel | |
| 5,263,218 A | 11/1993 | Giuliani et al. | |
| D341,943 S | 12/1993 | Si-Hoe | |
| D342,160 S | 12/1993 | Curtis et al. | |
| D342,161 S | 12/1993 | Curtis et al. | |
| D342,162 S | 12/1993 | Curtis et al. | |
| 5,267,579 A | 12/1993 | Bushberger | |
| D343,064 S | 1/1994 | Reno | |
| 5,279,314 A | 1/1994 | Poulos et al. | |
| 5,289,604 A | 3/1994 | Kressner | |
| 5,293,886 A | 3/1994 | Czapor | |
| 5,294,896 A | 3/1994 | Kjellander et al. | |
| 5,295,832 A | 3/1994 | Evans | |
| D346,212 S | 4/1994 | Hosl | |
| 5,299,723 A | 4/1994 | Hempel | |
| 5,301,381 A * | 4/1994 | Klupt | A46B 11/06 15/22.1 |
| 5,305,492 A | 4/1994 | Giuliani et al. | |
| D346,697 S | 5/1994 | O'Conke | |
| 5,309,590 A | 5/1994 | Giuliani et al. | |
| 5,309,591 A | 5/1994 | Hägele et al. | |
| 5,311,632 A | 5/1994 | Center | |
| 5,311,633 A | 5/1994 | Herzog et al. | |
| 5,315,731 A | 5/1994 | Millar | |
| D347,943 S | 6/1994 | Perry | |
| 5,323,796 A | 6/1994 | Urso | |
| 5,335,389 A | 8/1994 | Curtis et al. | |
| 5,337,435 A | 8/1994 | Krasner et al. | |
| 5,339,482 A | 8/1994 | Desimone et al. | |
| 5,341,534 A | 8/1994 | Serbinski et al. | |
| 5,341,537 A | 8/1994 | Curtis et al. | |
| 5,351,358 A | 10/1994 | Larrimore | |
| 5,353,460 A | 10/1994 | Bauman | |
| 5,354,246 A | 10/1994 | Gotman | |
| 5,355,638 A | 10/1994 | Hoffman | |
| 5,358,328 A | 10/1994 | Inoue et al. | |
| D352,396 S | 11/1994 | Curtis et al. | |
| D352,829 S | 11/1994 | Perry | |
| 5,359,747 A | 11/1994 | Amakasu | |
| 5,365,627 A | 11/1994 | Jousson et al. | |
| D353,490 S | 12/1994 | Hartwein | |
| 5,369,831 A | 12/1994 | Bock | |
| 5,371,915 A | 12/1994 | Key | |
| 5,373,602 A | 12/1994 | Bang | |
| D354,168 S | 1/1995 | Hartwein | |
| D354,559 S | 1/1995 | Knute | |
| 5,378,153 A | 1/1995 | Giuliani et al. | |
| 5,383,242 A | 1/1995 | Bigler et al. | |
| 5,392,483 A | 2/1995 | Heinzelman et al. | |
| 5,393,229 A | 2/1995 | Ram | |
| 5,396,678 A | 3/1995 | Bredall et al. | |
| 5,398,368 A | 3/1995 | Elder | |
| 5,400,811 A | 3/1995 | Meibauer | |
| 5,404,608 A | 4/1995 | Hommann | |
| 5,406,664 A | 4/1995 | Hukuba | |
| 5,406,965 A | 4/1995 | Levine | |
| D358,486 S | 5/1995 | Loew | |
| D358,713 S | 5/1995 | Perry | |
| D358,801 S | 5/1995 | Vos | |
| 5,411,041 A | 5/1995 | Ritter | |
| 5,412,827 A | 5/1995 | Muller et al. | |
| 5,416,942 A | 5/1995 | Baldacci et al. | |
| 5,419,346 A | 5/1995 | Tipp | |
| 5,419,703 A | 5/1995 | Warrin et al. | |
| D358,938 S | 6/1995 | Schneider et al. | |
| 5,421,726 A | 6/1995 | Okada | |
| 5,435,032 A | 7/1995 | McDougall | |
| 5,438,726 A | 8/1995 | Leite | |
| 5,446,940 A | 9/1995 | Curtis et al. | |
| D363,605 S | 10/1995 | Kou et al. | |
| 5,459,898 A | 10/1995 | Bacolot | |
| 5,461,744 A | 10/1995 | Merbach | |
| 5,467,494 A | 11/1995 | Muller et al. | |
| 5,467,495 A | 11/1995 | Boland et al. | |
| 5,482,466 A | 1/1996 | Haynes | |
| 5,484,281 A | 1/1996 | Renow et al. | |
| 5,496,256 A | 3/1996 | Bock et al. | |
| 5,499,420 A | 3/1996 | Boland | |
| 5,504,958 A | 4/1996 | Herzog | |
| 5,504,959 A | 4/1996 | Yukawa et al. | |
| 5,511,270 A | 4/1996 | Eliachar et al. | |
| 5,511,275 A | 4/1996 | Volpenhein et al. | |
| D370,125 S | 5/1996 | Craft et al. | |
| 5,518,012 A | 5/1996 | Dolan et al. | |
| D370,347 S | 6/1996 | Heinzelman et al. | |
| 5,529,494 A | 6/1996 | Vlacancich | |
| D371,242 S | 7/1996 | Shimatsu et al. | |
| 5,530,981 A | 7/1996 | Chen | |
| 5,544,382 A | 8/1996 | Giuliani et al. | |
| 5,545,968 A | 8/1996 | Hilfinger et al. | |
| 5,546,624 A | 8/1996 | Bock | |
| 5,546,626 A | 8/1996 | Chung | |
| 5,554,014 A | 9/1996 | Becker | |
| 5,561,881 A | 10/1996 | Klinger et al. | |
| D375,841 S | 11/1996 | Serbinski | |
| 5,573,020 A | 11/1996 | Robinson | |
| 5,577,285 A | 11/1996 | Drossler | |
| D376,695 S | 12/1996 | Tveras | |
| D376,893 S | 12/1996 | Gornet | |
| 5,579,786 A | 12/1996 | Wolk et al. | |
| 5,584,690 A | 12/1996 | Maassarani | |
| 5,588,452 A | 12/1996 | Peck | |
| 5,606,984 A | 3/1997 | Gao | |
| 5,609,170 A | 3/1997 | Roth | |
| 5,613,258 A | 3/1997 | Hilfinger et al. | |
| 5,613,259 A | 3/1997 | Craft et al. | |
| 5,617,601 A | 4/1997 | McDougall | |
| 5,617,602 A | 4/1997 | Okada | |
| 5,618,275 A | 4/1997 | Bock | |
| 5,619,766 A | 4/1997 | Zhadanov et al. | |
| 5,623,746 A | 4/1997 | Ichiro | |
| 5,625,916 A | 5/1997 | McDougall | |
| 5,626,472 A | 5/1997 | Pennetta | |
| 5,628,082 A | 5/1997 | Moskovich | |
| D380,903 S | 7/1997 | Moskovich | |
| D381,468 S | 7/1997 | Dolan et al. | |
| 5,651,157 A | 7/1997 | Hahn | |
| D382,407 S | 8/1997 | Craft et al. | |
| 5,652,990 A | 8/1997 | Driesen et al. | |
| 5,653,591 A | 8/1997 | Loge | |
| 5,678,274 A | 10/1997 | Liu | |
| 5,678,578 A | 10/1997 | Kossak et al. | |
| D386,314 S | 11/1997 | Moskovich | |
| 5,687,446 A | 11/1997 | Chen et al. | |
| 5,697,117 A | 12/1997 | Craft | |
| 5,700,146 A | 12/1997 | Kucar | |
| RE35,712 E | 1/1998 | Murayama | |
| D388,612 S | 1/1998 | Stutzer et al. | |
| D388,613 S | 1/1998 | Stutzer et al. | |
| D389,091 S | 1/1998 | Dickinson | |
| 5,704,087 A | 1/1998 | Strub | |
| 5,709,233 A | 1/1998 | Boland et al. | |
| D390,934 S | 2/1998 | McKeone | |
| 5,718,667 A | 2/1998 | Sugimoto et al. | |
| 5,732,433 A | 3/1998 | Göcking et al. | |
| 5,735,011 A | 4/1998 | Asher | |
| 5,738,575 A | 4/1998 | Bock | |
| 5,742,972 A | 4/1998 | Bredall et al. | |
| 5,749,380 A | 5/1998 | Zebuhr | |
| 5,762,078 A | 6/1998 | Zebuhr | |
| 5,775,346 A | 7/1998 | Szyszkowski | |
| 5,779,471 A | 7/1998 | Tseng et al. | |
| 5,784,742 A | 7/1998 | Giuliani et al. | |
| 5,784,743 A | 7/1998 | Shek | |
| D397,251 S | 8/1998 | Eguchi et al. | |
| D397,254 S | 8/1998 | Moskovich | |
| 5,787,908 A | 8/1998 | Robinson | |
| 5,794,295 A | 8/1998 | Shen | |
| 5,796,325 A | 8/1998 | Lundell et al. | |
| 5,815,872 A | 10/1998 | Meginnis, III et al. | |
| 5,816,271 A | 10/1998 | Urso | |

(56) References Cited

U.S. PATENT DOCUMENTS

| | | |
|---|---|---|
| 5,822,821 A | 10/1998 | Sham |
| 5,827,064 A | 10/1998 | Bock |
| D400,713 S | 11/1998 | Solanki |
| 5,836,030 A | 11/1998 | Hazeu et al. |
| 5,842,244 A | 12/1998 | Hilfinger et al. |
| 5,850,655 A | 12/1998 | Göcking et al. |
| 5,851,514 A | 12/1998 | Hassan et al. |
| D403,511 S | 1/1999 | Serbinski |
| 5,855,216 A | 1/1999 | Robinson |
| 5,862,558 A | 1/1999 | Hilfinger et al. |
| 5,864,911 A | 2/1999 | Arnoux |
| 5,864,915 A | 2/1999 | Ra |
| 5,867,856 A | 2/1999 | Herzog |
| 5,875,797 A | 3/1999 | Chiang et al. |
| 5,893,175 A | 4/1999 | Cooper |
| 5,896,614 A | 4/1999 | Flewitt |
| 5,896,615 A | 4/1999 | Zaksenberg |
| 5,899,693 A | 5/1999 | Himeno et al. |
| 5,900,230 A | 5/1999 | Cutler |
| 5,901,397 A | 5/1999 | Hafele et al. |
| D410,787 S | 6/1999 | Barre et al. |
| 5,908,038 A | 6/1999 | Bennett |
| D411,769 S | 7/1999 | Wright |
| 5,921,254 A | 7/1999 | Carlucci et al. |
| 5,927,300 A | 7/1999 | Boland et al. |
| 5,927,976 A | 7/1999 | Wu |
| 5,930,858 A | 8/1999 | Jung |
| 5,931,170 A | 8/1999 | Wu |
| 5,934,908 A | 8/1999 | Woog et al. |
| 5,943,723 A | 8/1999 | Hilfinger et al. |
| 5,944,033 A | 8/1999 | Robinson |
| D413,694 S | 9/1999 | Bennett |
| D414,937 S | 10/1999 | Cornu et al. |
| D414,939 S | 10/1999 | Pedro, Jr. et al. |
| D416,999 S | 11/1999 | Miyamoto |
| 5,974,613 A | 11/1999 | Herzog |
| 5,974,615 A | 11/1999 | Schwarz-Hartmann et al. |
| 5,980,541 A | 11/1999 | Tenzer |
| 5,987,681 A | 11/1999 | Hahn et al. |
| 5,991,957 A | 11/1999 | Watanabe |
| D417,960 S | 12/1999 | Moskovich et al. |
| 6,000,083 A | 12/1999 | Blaustein et al. |
| 6,009,589 A | 1/2000 | Driesen et al. |
| 6,021,538 A | 2/2000 | Kressner et al. |
| 6,026,828 A | 2/2000 | Altshuler |
| 6,032,313 A | 3/2000 | Tsang |
| 6,035,476 A | 3/2000 | Underwood et al. |
| 6,047,429 A * | 4/2000 | Wu ................... A61C 17/36 15/29 |
| 6,047,711 A | 4/2000 | Wagner |
| 6,050,818 A | 4/2000 | Boland et al. |
| RE36,699 E | 5/2000 | Murayama |
| D423,784 S | 5/2000 | Joulin |
| D424,181 S | 5/2000 | Caplow |
| 6,056,548 A | 5/2000 | Neuberger et al. |
| 6,065,176 A | 5/2000 | Watanabe et al. |
| 6,081,957 A | 7/2000 | Webb |
| 6,092,252 A | 7/2000 | Fischer et al. |
| 6,095,811 A | 8/2000 | Stearns |
| 6,102,700 A | 8/2000 | Haczek et al. |
| 6,106,294 A | 8/2000 | Daniel |
| 6,120,755 A | 9/2000 | Jacobs |
| 6,138,310 A | 10/2000 | Porper et al. |
| 6,140,723 A | 10/2000 | Matsui et al. |
| 6,148,462 A | 11/2000 | Zseng |
| D434,563 S | 12/2000 | Lim et al. |
| 6,154,912 A | 12/2000 | Li |
| 6,162,202 A | 12/2000 | Sicurelli et al. |
| 6,164,967 A * | 12/2000 | Sale ................... A46B 11/002 15/22.1 |
| 6,165,131 A | 12/2000 | Cuce et al. |
| D437,049 S | 1/2001 | Hartwein |
| D437,090 S | 1/2001 | Lang et al. |
| D437,091 S | 1/2001 | Lang et al. |
| 6,178,579 B1 | 1/2001 | Blaustein et al. |
| D437,663 S | 2/2001 | Lang et al. |
| D437,976 S | 2/2001 | Narayanan et al. |
| D437,977 S | 2/2001 | Lang et al. |
| D438,306 S | 2/2001 | Narayanan |
| 6,183,254 B1 | 2/2001 | Cohen |
| 6,195,828 B1 | 3/2001 | Fritsch |
| 6,200,134 B1 | 3/2001 | Kovac |
| 6,202,242 B1 | 3/2001 | Salmon et al. |
| 6,203,320 B1 | 3/2001 | Williams et al. |
| 6,220,857 B1 | 4/2001 | Abels |
| 6,230,354 B1 | 5/2001 | Sproat |
| 6,230,717 B1 | 5/2001 | Marx et al. |
| 6,233,773 B1 | 5/2001 | Karge et al. |
| 6,237,178 B1 | 5/2001 | Krammer et al. |
| D444,629 S | 7/2001 | Etter et al. |
| 6,253,404 B1 | 7/2001 | Boland et al. |
| 6,267,593 B1 | 7/2001 | Haczek et al. |
| 6,280,190 B1 | 8/2001 | Hoffman |
| 6,299,444 B1 | 10/2001 | Cohen |
| 6,308,358 B2 | 10/2001 | Gruber et al. |
| 6,308,359 B2 | 10/2001 | Fritsch et al. |
| 6,341,400 B1 | 1/2002 | Kobayashi et al. |
| 6,343,396 B1 | 2/2002 | Simovitz et al. |
| 6,343,400 B1 | 2/2002 | Massholder et al. |
| 6,347,425 B1 | 2/2002 | Fattori et al. |
| 6,349,442 B1 | 2/2002 | Cohen et al. |
| 6,353,956 B1 | 3/2002 | Berge |
| 6,360,395 B2 | 3/2002 | Blaustein et al. |
| 6,360,398 B1 | 3/2002 | Wiegner et al. |
| D455,201 S | 4/2002 | Jones |
| D455,203 S | 4/2002 | Jones |
| 6,363,565 B1 | 4/2002 | Paffrath |
| 6,365,108 B1 | 4/2002 | Philyaw |
| 6,367,108 B1 | 4/2002 | Fritsch et al. |
| 6,374,448 B2 | 4/2002 | Seifert |
| 6,375,459 B1 | 4/2002 | Kamen et al. |
| D457,949 S | 5/2002 | Krug |
| 6,381,795 B1 | 5/2002 | Hofmann et al. |
| 6,401,288 B1 | 6/2002 | Porper et al. |
| 6,421,865 B1 | 7/2002 | McDougall |
| 6,421,866 B1 | 7/2002 | McDougall |
| 6,421,867 B1 | 7/2002 | Weihrauch |
| 6,422,867 B2 | 7/2002 | Lang et al. |
| 6,434,773 B1 | 8/2002 | Kuo |
| D463,627 S | 9/2002 | Lang et al. |
| 6,446,294 B1 | 9/2002 | Specht |
| 6,446,295 B1 | 9/2002 | Calabrese |
| 6,447,293 B1 | 9/2002 | Sokol et al. |
| 6,453,497 B1 | 9/2002 | Chiang et al. |
| 6,453,498 B1 | 9/2002 | Wu |
| 6,453,499 B1 | 9/2002 | Leuermann |
| D464,799 S | 10/2002 | Crossman et al. |
| 6,463,615 B1 | 10/2002 | Gruber et al. |
| 6,490,747 B1 | 12/2002 | Metwally |
| 6,497,237 B1 | 12/2002 | Ali |
| 6,510,575 B2 | 1/2003 | Calabrese |
| 6,526,994 B1 | 3/2003 | Santoro |
| 6,536,066 B2 | 3/2003 | Dickie |
| 6,564,940 B2 | 5/2003 | Blaustein et al. |
| 6,571,804 B2 | 6/2003 | Adler |
| 6,574,820 B1 | 6/2003 | DePuydt et al. |
| 6,581,233 B1 | 6/2003 | Cheng |
| 6,581,234 B2 | 6/2003 | Lee et al. |
| D476,743 S | 7/2003 | D'Silva |
| 6,588,042 B2 | 7/2003 | Fritsch et al. |
| 6,599,048 B2 | 7/2003 | Kuo |
| 6,609,527 B2 | 8/2003 | Brown |
| 6,609,910 B2 | 8/2003 | Narayanan |
| 6,619,219 B2 | 9/2003 | Marcon et al. |
| 6,622,333 B1 | 9/2003 | Rehkemper et al. |
| 6,647,577 B2 | 11/2003 | Tam |
| D484,311 S | 12/2003 | Cacka et al. |
| 6,654,979 B2 | 12/2003 | Calabrese |
| 6,659,674 B2 | 12/2003 | Carlucci et al. |
| 6,663,386 B1 | 12/2003 | Moelsgaard |
| 6,665,901 B2 | 12/2003 | Driesen et al. |
| D484,971 S | 1/2004 | Hartwein |
| 6,681,418 B1 | 1/2004 | Bierend |
| 6,691,363 B2 | 2/2004 | Huen |

(56) References Cited

U.S. PATENT DOCUMENTS

| | | |
|---|---|---|
| 6,701,565 B2 | 3/2004 | Hafemann |
| 6,709,185 B2 | 3/2004 | Lefevre |
| 6,721,986 B2 | 4/2004 | Zhuan |
| 6,725,490 B2 | 4/2004 | Blaustein et al. |
| 6,735,803 B2 | 5/2004 | Kuo |
| 6,735,804 B2 | 5/2004 | Carlucci et al. |
| 6,739,012 B2 | 5/2004 | Grez et al. |
| 6,751,823 B2 | 6/2004 | Biro et al. |
| 6,760,945 B2 | 7/2004 | Ferber et al. |
| 6,760,946 B2 | 7/2004 | DePuydt |
| 6,766,548 B1 | 7/2004 | Lukas et al. |
| 6,766,549 B2 | 7/2004 | Klupt |
| 6,766,807 B2 | 7/2004 | Piccolo et al. |
| 6,779,126 B1 | 8/2004 | Lin et al. |
| 6,779,215 B2 | 8/2004 | Hartman et al. |
| 6,785,926 B2 | 9/2004 | Green |
| 6,785,929 B2 | 9/2004 | Fritsch et al. |
| 6,792,640 B2 | 9/2004 | Lev |
| 6,795,993 B2 | 9/2004 | Lin |
| 6,798,169 B2 | 9/2004 | Stratmann et al. |
| 6,799,346 B2 | 10/2004 | Jeng et al. |
| 6,802,097 B2 | 10/2004 | Hafliger et al. |
| 6,808,331 B2 | 10/2004 | Hall et al. |
| 6,810,550 B1 | 11/2004 | Wuelknitz et al. |
| 6,813,793 B2 | 11/2004 | Eliav |
| 6,813,794 B2 | 11/2004 | Weng |
| 6,821,119 B2 | 11/2004 | Shortt et al. |
| 6,823,875 B2 | 11/2004 | Hotta et al. |
| 6,827,910 B2 | 12/2004 | Chen |
| 6,829,801 B2 | 12/2004 | Schutz |
| 6,832,819 B1 | 12/2004 | Weihrauch |
| D500,599 S | 1/2005 | Callaghan |
| D501,084 S | 1/2005 | Schaefer et al. |
| 6,836,917 B2 | 1/2005 | Blaustein et al. |
| 6,845,537 B2 | 1/2005 | Wong |
| 6,848,141 B2 | 2/2005 | Eliav et al. |
| 6,851,150 B2 | 2/2005 | Chiang |
| 6,851,153 B2 | 2/2005 | Lehman |
| 6,854,965 B2 | 2/2005 | Ebner et al. |
| 6,862,771 B1 | 3/2005 | Muller |
| 6,871,373 B2 | 3/2005 | Driesen et al. |
| 6,874,509 B2 | 4/2005 | Bergman |
| 6,886,207 B1 | 5/2005 | Solanki |
| 6,889,401 B2 | 5/2005 | Fattori et al. |
| 6,889,829 B2 | 5/2005 | Lev et al. |
| 6,892,412 B2 | 5/2005 | Gatzemeyer et al. |
| 6,892,413 B2 | 5/2005 | Blaustein et al. |
| 6,895,625 B2 | 5/2005 | Lev et al. |
| 6,895,629 B1 | 5/2005 | Wenzler |
| 6,902,337 B2 | 6/2005 | Kuo |
| 6,907,636 B2 | 6/2005 | Hafemann |
| 6,918,153 B2 | 7/2005 | Gruber |
| 6,920,659 B2 | 7/2005 | Cacka et al. |
| 6,920,660 B2 | 7/2005 | Lam |
| 6,928,685 B1 | 8/2005 | Blaustein et al. |
| 6,931,688 B2 | 8/2005 | Moskovich et al. |
| 6,938,293 B2 | 9/2005 | Eliav et al. |
| 6,938,294 B2 | 9/2005 | Fattori et al. |
| 6,944,901 B2 | 9/2005 | Gatzemeyer et al. |
| 6,945,397 B2 | 9/2005 | Brattesani et al. |
| 6,948,209 B2 | 9/2005 | Chan |
| 6,952,854 B2 | 10/2005 | Blaustein et al. |
| 6,952,855 B2 | 10/2005 | Lev et al. |
| 6,954,961 B2 | 10/2005 | Ferber et al. |
| 6,955,539 B2 | 10/2005 | Shortt et al. |
| 6,957,468 B2 | 10/2005 | Driesen et al. |
| 6,957,469 B2 | 10/2005 | Davies |
| 6,966,093 B2 | 11/2005 | Eliav et al. |
| 6,973,694 B2 | 12/2005 | Schutz et al. |
| 6,983,507 B2 | 1/2006 | McDougall |
| 6,988,777 B2 | 1/2006 | Pfenniger et al. |
| 6,990,706 B2 | 1/2006 | Broecker et al. |
| D515,215 S | 2/2006 | Wang |
| D515,318 S | 2/2006 | Chan et al. |
| 6,993,803 B2 | 2/2006 | Chan |
| 6,997,191 B2 | 2/2006 | Nudo, Sr. |
| 7,007,331 B2 | 3/2006 | Davics et al. |
| 7,008,225 B2 | 3/2006 | Ito et al. |
| 7,020,925 B1 | 4/2006 | Gitelis |
| 7,021,851 B1 | 4/2006 | King |
| 7,024,717 B2 | 4/2006 | Hilscher et al. |
| 7,024,718 B2 | 4/2006 | Chu |
| 7,036,180 B2 | 5/2006 | Hanlon |
| 7,055,205 B2 | 6/2006 | Aoyama |
| 7,059,334 B2 | 6/2006 | Dougan et al. |
| 7,065,821 B2 | 6/2006 | Fattori |
| RE39,185 E | 7/2006 | Noe et al. |
| 7,070,354 B1 | 7/2006 | Gutierrez-Caro |
| 7,080,980 B2 | 7/2006 | Klupt |
| 7,082,638 B2 | 8/2006 | Koh |
| 7,082,950 B2 | 8/2006 | Kossak et al. |
| 7,086,111 B2 | 8/2006 | Hilscher et al. |
| 7,089,621 B2 | 8/2006 | Hohlbein |
| 7,120,960 B2 | 10/2006 | Hilscher et al. |
| 7,122,921 B2 | 10/2006 | Hall et al. |
| 7,124,461 B2 | 10/2006 | Blaustein et al. |
| 7,124,462 B2 | 10/2006 | Lee |
| 7,128,492 B1 | 10/2006 | Thames, Jr. |
| D532,570 S | 11/2006 | Vizcarra |
| 7,131,838 B2 | 11/2006 | Suzuki et al. |
| 7,137,136 B1 | 11/2006 | Gatzemeyer et al. |
| 7,140,058 B2 | 11/2006 | Gatzemeyer et al. |
| 7,146,675 B2 | 12/2006 | Ansari et al. |
| 7,162,764 B2 | 1/2007 | Drossler et al. |
| 7,162,767 B2 | 1/2007 | Pfenniger et al. |
| 7,168,122 B1 | 1/2007 | Riddell |
| 7,168,125 B2 | 1/2007 | Hohlbein |
| 7,174,596 B2 | 2/2007 | Fischer et al. |
| 7,175,238 B1 | 2/2007 | Barman |
| 7,181,799 B2 | 2/2007 | Gavney, Jr. et al. |
| 7,185,383 B2 | 3/2007 | Gatzemeyer et al. |
| 7,186,226 B2 | 3/2007 | Woolley |
| D540,542 S | 4/2007 | Harada |
| 7,198,487 B2 | 4/2007 | Luettgen et al. |
| 7,207,080 B2 | 4/2007 | Hilscher et al. |
| 7,210,184 B2 | 5/2007 | Eliav et al. |
| 7,213,293 B1 | 5/2007 | Schraga |
| 7,213,995 B2 | 5/2007 | Bravo-Loubriel |
| 7,217,332 B2 | 5/2007 | Brown, Jr. et al. |
| 7,222,381 B2 | 5/2007 | Kraemer |
| 7,222,382 B2 | 5/2007 | Choi et al. |
| 7,225,494 B2 | 6/2007 | Chan et al. |
| 7,228,583 B2 | 6/2007 | Chan et al. |
| 7,234,187 B2 | 6/2007 | Blaustein et al. |
| 7,234,192 B2 | 6/2007 | Barbar |
| D553,980 S | 10/2007 | VerWeyst |
| 7,469,440 B2 | 12/2008 | Boland et al. |
| D585,132 S | 1/2009 | Pukall |
| D588,262 S | 3/2009 | Pukall |
| D592,748 S | 5/2009 | Boulton |
| 7,554,225 B2 | 6/2009 | Kraus et al. |
| D601,694 S | 10/2009 | Rocklin |
| D608,430 S | 1/2010 | Slothower |
| 7,732,952 B1 | 6/2010 | Taylor |
| D622,928 S | 9/2010 | Griebel |
| D623,376 S | 9/2010 | Griebel |
| D625,406 S | 10/2010 | Seki et al. |
| 7,857,623 B2 * | 12/2010 | Grez ..................... A61C 17/02 15/22.1 |
| 8,032,964 B2 | 10/2011 | Farrell et al. |
| D651,409 S | 1/2012 | Papenfu |
| D651,805 S | 1/2012 | Hay |
| D653,340 S | 1/2012 | Goerge et al. |
| D655,380 S | 3/2012 | Taylor |
| D658,381 S | 5/2012 | Gebski |
| D658,538 S | 5/2012 | Korzeniowski |
| 8,196,245 B2 | 6/2012 | Schwarz-Hartmann et al. |
| 8,220,726 B2 | 7/2012 | Qiu et al. |
| 8,256,979 B2 | 9/2012 | Hilscher et al. |
| D668,339 S | 10/2012 | Luoto |
| 8,297,534 B2 | 10/2012 | Li et al. |
| D671,637 S | 11/2012 | Gebski et al. |
| D672,018 S | 12/2012 | Bucher |
| 8,366,024 B2 | 2/2013 | Leber |

(56) References Cited

U.S. PATENT DOCUMENTS

| | | | |
|---|---|---|---|
| 8,403,577 B2 | 3/2013 | Khoshnevis |
| 8,418,300 B2 | 4/2013 | Miller et al. |
| 8,453,285 B2 | 6/2013 | Dickie |
| D686,311 S | 7/2013 | Mori |
| D694,378 S | 11/2013 | Bates |
| D694,398 S | 11/2013 | Taylor |
| D700,343 S | 2/2014 | Liu |
| D702,819 S | 4/2014 | Garland |
| D702,821 S | 4/2014 | Garland |
| D707,350 S | 6/2014 | Woodard |
| D709,183 S | 7/2014 | Kemlein |
| D714,929 S | 10/2014 | Kim et al. |
| D714,930 S | 10/2014 | Kim et al. |
| D717,412 S | 11/2014 | Bucher |
| D717,427 S | 11/2014 | Kim |
| D718,855 S | 12/2014 | Kim et al. |
| D723,387 S | 3/2015 | Fath |
| D725,770 S | 3/2015 | Kim et al. |
| D731,640 S | 6/2015 | Kim et al. |
| D740,936 S | 10/2015 | Kim et al. |
| D745,329 S | 12/2015 | Ong |
| D746,975 S | 1/2016 | Schenck |
| D747,464 S | 1/2016 | Taylor |
| D754,330 S | 4/2016 | Kim et al. |
| D756,122 S | 5/2016 | Taylor |
| 2001/0035194 A1 | 11/2001 | Narayanan |
| 2001/0039955 A1 | 11/2001 | Winters et al. |
| 2001/0054563 A1 | 12/2001 | Lang et al. |
| 2002/0017474 A1 | 2/2002 | Blaustein et al. |
| 2002/0029988 A1 | 3/2002 | Blaustein et al. |
| 2002/0032941 A1 | 3/2002 | Blaustein et al. |
| 2002/0039720 A1 | 4/2002 | Marx et al. |
| 2002/0059685 A1 | 5/2002 | Paffrath |
| 2002/0078514 A1 | 6/2002 | Blaustein et al. |
| 2002/0084707 A1 | 7/2002 | Tang |
| 2002/0088068 A1 | 7/2002 | Levy et al. |
| 2002/0090252 A1 | 7/2002 | Hall et al. |
| 2002/0092104 A1 | 7/2002 | Ferber |
| 2002/0095734 A1 | 7/2002 | Wong |
| 2002/0100134 A1 | 8/2002 | Dunn et al. |
| 2002/0106607 A1 | 8/2002 | Horowitz |
| 2002/0108193 A1* | 8/2002 | Gruber ............... A46B 11/063 15/22.1 |
| 2002/0137728 A1 | 9/2002 | Montgomery |
| 2002/0138926 A1 | 10/2002 | Brown, Jr. et al. |
| 2002/0152563 A1 | 10/2002 | Sato |
| 2002/0152564 A1 | 10/2002 | Blaustein et al. |
| 2002/0152565 A1* | 10/2002 | Klupt ................. A61C 17/36 15/29 |
| 2002/0174498 A1 | 11/2002 | Li |
| 2002/0178519 A1 | 12/2002 | Zarlengo |
| 2003/0005544 A1 | 1/2003 | Felix |
| 2003/0033679 A1 | 2/2003 | Fattori et al. |
| 2003/0033680 A1 | 2/2003 | Davies et al. |
| 2003/0041396 A1 | 3/2003 | Dickie |
| 2003/0060743 A1 | 3/2003 | Chang |
| 2003/0064348 A1 | 4/2003 | Sokol et al. |
| 2003/0066145 A1 | 4/2003 | Prineppi |
| 2003/0074751 A1 | 4/2003 | Wu |
| 2003/0079305 A1 | 5/2003 | Takahata et al. |
| 2003/0084525 A1 | 5/2003 | Blaustein et al. |
| 2003/0084526 A1 | 5/2003 | Brown et al. |
| 2003/0084527 A1 | 5/2003 | Brown et al. |
| 2003/0097723 A1 | 5/2003 | Li |
| 2003/0099502 A1 | 5/2003 | Lai |
| 2003/0101526 A1 | 6/2003 | Hilscher |
| 2003/0106565 A1 | 6/2003 | Andrews |
| 2003/0140435 A1 | 7/2003 | Eliav et al. |
| 2003/0140437 A1 | 7/2003 | Eliav et al. |
| 2003/0140937 A1 | 7/2003 | Cook |
| 2003/0150474 A1 | 8/2003 | Doyscher |
| 2003/0154567 A1 | 8/2003 | Drossler et al. |
| 2003/0154568 A1 | 8/2003 | Boland et al. |
| 2003/0163881 A1 | 9/2003 | Driesen et al. |
| 2003/0163882 A1 | 9/2003 | Blaustein et al. |
| 2003/0182743 A1 | 10/2003 | Gatzemeyer et al. |
| 2003/0182746 A1 | 10/2003 | Fattori et al. |
| 2003/0192139 A1 | 10/2003 | Fattori et al. |
| 2003/0196283 A1 | 10/2003 | Eliav et al. |
| 2003/0196677 A1 | 10/2003 | Wiseman |
| 2003/0213075 A1 | 11/2003 | Hui et al. |
| 2003/0221267 A1 | 12/2003 | Chan |
| 2003/0221269 A1 | 12/2003 | Zhuan |
| 2003/0226223 A1 | 12/2003 | Chan |
| 2004/0010870 A1 | 1/2004 | McNair |
| 2004/0010871 A1 | 1/2004 | Nishinaka et al. |
| 2004/0016068 A1 | 1/2004 | Lee |
| 2004/0016069 A1 | 1/2004 | Lee |
| 2004/0034951 A1 | 2/2004 | Davies et al. |
| 2004/0045106 A1 | 3/2004 | Lam |
| 2004/0045107 A1 | 3/2004 | Egeresi |
| 2004/0049867 A1 | 3/2004 | Hui |
| 2004/0049868 A1 | 3/2004 | Ng |
| 2004/0060137 A1 | 4/2004 | Eliav |
| 2004/0063603 A1 | 4/2004 | Dave et al. |
| 2004/0068811 A1 | 4/2004 | Fulop et al. |
| 2004/0074026 A1 | 4/2004 | Blaustein et al. |
| 2004/0083566 A1 | 5/2004 | Blaustein et al. |
| 2004/0087882 A1 | 5/2004 | Roberts et al. |
| 2004/0088806 A1 | 5/2004 | DePuydt et al. |
| 2004/0088807 A1 | 5/2004 | Blaustein et al. |
| 2004/0091834 A1 | 5/2004 | Rizoiu et al. |
| 2004/0107521 A1 | 6/2004 | Chan et al. |
| 2004/0119344 A1 | 6/2004 | Lau et al. |
| 2004/0123409 A1 | 7/2004 | Dickie |
| 2004/0126730 A1 | 7/2004 | Panagotacos |
| 2004/0128778 A1 | 7/2004 | Wong |
| 2004/0129296 A1 | 7/2004 | Treacy et al. |
| 2004/0134001 A1 | 7/2004 | Chan |
| 2004/0143917 A1 | 7/2004 | Ek |
| 2004/0154112 A1 | 8/2004 | Braun et al. |
| 2004/0163191 A1 | 8/2004 | Cuffaro et al. |
| 2004/0168269 A1 | 9/2004 | Kunita et al. |
| 2004/0168272 A1 | 9/2004 | Prineppi |
| 2004/0177458 A1 | 9/2004 | Chan et al. |
| 2004/0187889 A1 | 9/2004 | Kemp et al. |
| 2004/0200016 A1 | 10/2004 | Chan et al. |
| 2004/0209222 A1 | 10/2004 | Snyder |
| 2005/0004498 A1 | 1/2005 | Klupt |
| 2005/0008986 A1 | 1/2005 | Sokol et al. |
| 2005/0064371 A1 | 3/2005 | Soukos et al. |
| 2005/0102773 A1* | 5/2005 | Obermann ......... A61C 17/3418 15/4 |
| 2005/0144745 A1* | 7/2005 | Russell ................ A46B 7/10 15/23 |
| 2005/0177079 A1 | 8/2005 | Pan |
| 2005/0189000 A1 | 9/2005 | Cacka et al. |
| 2005/0255427 A1 | 11/2005 | Shortt et al. |
| 2005/0266376 A1 | 12/2005 | Sokol et al. |
| 2006/0010624 A1* | 1/2006 | Cleland ................. A46B 13/06 15/29 |
| 2006/0078844 A1* | 4/2006 | Goldman ............. A61C 1/0084 433/80 |
| 2007/0082317 A1 | 4/2007 | Chuang |
| 2007/0151051 A1 | 7/2007 | Filsouf |
| 2008/0189951 A1 | 8/2008 | Molema et al. |
| 2008/0213719 A1 | 9/2008 | Giniger et al. |
| 2008/0213731 A1 | 9/2008 | Fishburne |
| 2008/0253906 A1 | 10/2008 | Strong |
| 2008/0307591 A1 | 12/2008 | Farrell et al. |
| 2009/0019650 A1 | 1/2009 | Grez et al. |
| 2009/0019651 A1 | 1/2009 | Dickie |
| 2009/0178215 A1 | 7/2009 | Gall |
| 2009/0188780 A1 | 7/2009 | Watanabe |
| 2009/0281454 A1 | 11/2009 | Baker et al. |
| 2010/0010524 A1 | 1/2010 | Barrington |
| 2010/0055634 A1 | 3/2010 | Spaulding et al. |
| 2010/0132139 A1 | 6/2010 | Jungnickel |
| 2010/0186179 A1 | 7/2010 | Miller |
| 2011/0010874 A1 | 1/2011 | Dickie |
| 2011/0041268 A1 | 2/2011 | Iwahori et al. |
| 2011/0047729 A1 | 3/2011 | Iwahori |
| 2011/0076090 A1 | 3/2011 | Wu et al. |
| 2011/0083288 A1 | 4/2011 | Kressner |

(56) References Cited

U.S. PATENT DOCUMENTS

| | | | |
|---|---|---|---|
| 2011/0307039 A1 | 12/2011 | Cornell | |
| 2012/0021374 A1 | 1/2012 | Cacka et al. | |
| 2012/0064480 A1 | 3/2012 | Hegemann | |
| 2012/0112566 A1 | 5/2012 | Doll | |
| 2012/0179118 A1 | 7/2012 | Hair | |
| 2012/0189976 A1 | 7/2012 | McDonough et al. | |
| 2012/0192366 A1 | 8/2012 | Cobabe | |
| 2012/0198635 A1 | 8/2012 | Hilscher | |
| 2012/0216358 A1 | 8/2012 | Kloster | |
| 2012/0266396 A1 | 10/2012 | Leung | |
| 2012/0277663 A1 | 11/2012 | Millman et al. | |
| 2012/0279002 A1 | 11/2012 | Sokol et al. | |
| 2013/0295520 A1 | 11/2013 | Hsieh | |
| 2014/0106296 A1 | 4/2014 | Woodard et al. | |
| 2014/0259469 A1 | 9/2014 | Garrigues | |
| 2014/0259474 A1 | 9/2014 | Sokol et al. | |
| 2014/0272769 A1 | 9/2014 | Luettgen et al. | |
| 2014/0272782 A1 | 9/2014 | Luettgen et al. | |
| 2014/0352088 A1* | 12/2014 | Wu | A61C 17/36 15/22.1 |
| 2015/0107035 A1 | 4/2015 | Sokol et al. | |
| 2015/0182319 A1 | 7/2015 | Wagner et al. | |
| 2015/0327965 A1 | 11/2015 | Garrigues | |

FOREIGN PATENT DOCUMENTS

| | | | |
|---|---|---|---|
| CH | 609238 | | 2/1979 |
| CN | 201223467 | | 4/2009 |
| CN | 102111032 | | 6/2011 |
| CN | 204049908 | | 12/2014 |
| DE | 243224 | | 4/1910 |
| DE | 2019003 | | 11/1971 |
| DE | 2714876 | | 10/1978 |
| DE | 1766651 | | 12/1981 |
| DE | 3346651 | | 7/1985 |
| DE | 3431481 | | 2/1986 |
| DE | 3512190 | | 10/1986 |
| DE | 8626725 | | 5/1987 |
| DE | 3736308 | | 7/1989 |
| DE | 4142404 | | 7/1991 |
| DE | 4003305 | | 8/1991 |
| DE | 4223195 | | 1/1994 |
| DE | 4223196 | | 1/1994 |
| DE | 4226658 | | 2/1994 |
| DE | 4226659 | | 2/1994 |
| DE | 4241576 | | 6/1994 |
| DE | 4309078 | | 9/1994 |
| DE | 29715234 | | 12/1997 |
| DE | 29919053 | | 12/2000 |
| DE | 19961447 | | 7/2001 |
| DE | 20319996 | | 3/2004 |
| DE | 102006061381 | | 6/2008 |
| EP | 0210094 | | 6/1986 |
| EP | 0354352 | | 2/1990 |
| EP | 0661025 | | 7/1995 |
| EP | 0704180 | | 4/1996 |
| EP | 0968686 | | 1/2000 |
| EP | 1825827 | | 8/2007 |
| FR | 429447 | | 9/1911 |
| FR | 1171337 | | 1/1959 |
| FR | 2530135 | * | 1/1984 |
| GB | 477799 | | 1/1938 |
| GB | 500517 | | 2/1939 |
| GB | 838564 | | 6/1960 |
| GB | 899618 | | 6/1962 |
| GB | 1365729 | * | 9/1974 |
| GB | 1583558 | | 8/1977 |
| GB | 2175494 | | 12/1986 |
| GB | 2250428 | | 6/1992 |
| JP | 53029847 | | 3/1978 |
| JP | 53033753 | | 3/1978 |
| JP | 3222905 | | 10/1991 |
| KR | 20120126265 | | 11/2012 |
| SE | 324221 | | 5/1970 |
| WO | WO 91/13570 | | 9/1991 |
| WO | WO 91/19437 | | 12/1991 |
| WO | WO 92/10146 | | 6/1992 |
| WO | WO 92/16160 | | 10/1992 |
| WO | WO 93/10721 | | 6/1993 |
| WO | WO 93/15628 | | 8/1993 |
| WO | WO 94/04093 | | 3/1994 |
| WO | WO 94/26144 | | 11/1994 |
| WO | WO 95/02375 | | 1/1995 |
| WO | WO 95/33419 | | 12/1995 |
| WO | WO 98/47443 | | 10/1998 |
| WO | WO 01/28452 | | 4/2001 |
| WO | WO 01/45582 | | 6/2001 |
| WO | WO 02/071970 | | 9/2002 |
| WO | WO 02/071971 | | 9/2002 |
| WO | 2004060259 A2 | | 7/2004 |
| WO | WO2004/062518 | | 7/2004 |
| WO | WO05/063143 | | 7/2005 |
| WO | WO 2006/012974 | | 2/2006 |
| WO | WO 2008/070730 | | 6/2008 |
| WO | WO2008/070730 | | 6/2008 |
| WO | 2008157585 A1 | | 12/2008 |
| WO | 2013124691 A1 | | 8/2013 |
| WO | WO 2014/145890 | | 9/2014 |
| WO | WO 2014/150418 | | 9/2014 |

OTHER PUBLICATIONS

Teledyne Water Pik "Plaque Control 3000" plaque removal instrument (Jul. 1991).
American Dentronics Incorporated "Soniplak" sonic plaque removal system (May 1993).
Teledyne Water Pik "Sensonic" Toothbrush, sales brochure (at least as early as Sep. 1994).
Design of a Toothbrush, p. 361, Danish Official Design Gazette, published May 16, 1997.
International Search Report and Written Opinion, PCT Application No. PCT/US2012/036092, 8 pages, Jul. 10, 2012.
Waterpik WP350W Oral Irrigator. Dentist.net. Copyright date 2013. Date accessed: Mar. 30, 2017, 2 pages <http://www.dentalhoo.com/waterpik-wp350.asp>.
iPik Portable Oral Irrigator. AliExpress. Date reviewed: Oct. 5, 2016. <https://www.allexpress.com/...e-Oral-Care-Product-Nasal-Irrigator-Tooth-Flosser-Water/1525541997.html?aff_platform=aaf &cpt=1490913714609&sk=yfAeyJa &aff_trace_key=c5a300c4f02e46d08c042f5292e1762f-1490913714609-07517-yfAeyJa>, 18 pages.
Brite Leafs Professional Portable 2-in-1 Nasal Sinus & Oral Irrigator. Brite Leafs. Copyright date 2012, <http://www.briteleafs.com/product6.html>, 1 page.
AliExpress. Date reviewed: Jan. 12, 2017. <https://www.aliexpress.com/item/Cordless-Water-Floss-Portable-Oral-Irrigator-Dental-Water-Flosser-Waterpic-Whatpick-Dental-Water-Pic-Whater-Pick/32769416341.html?spm=2114.40010308.4.75.Owuzfj>.

* cited by examiner

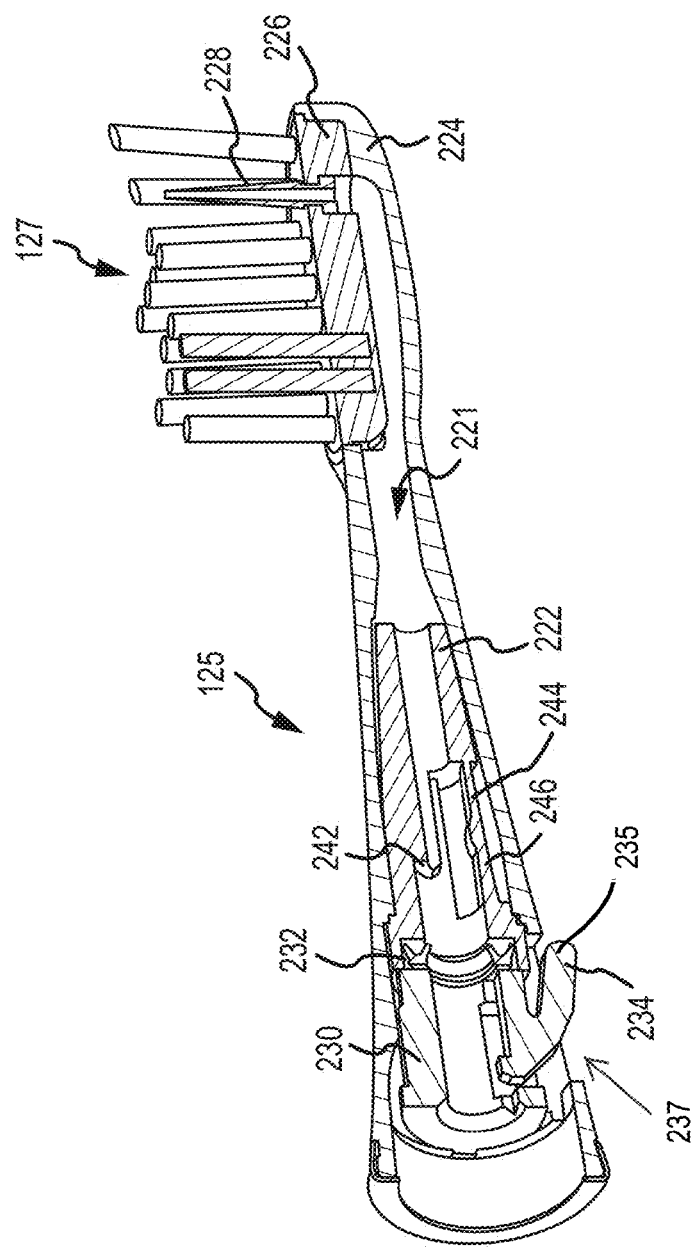

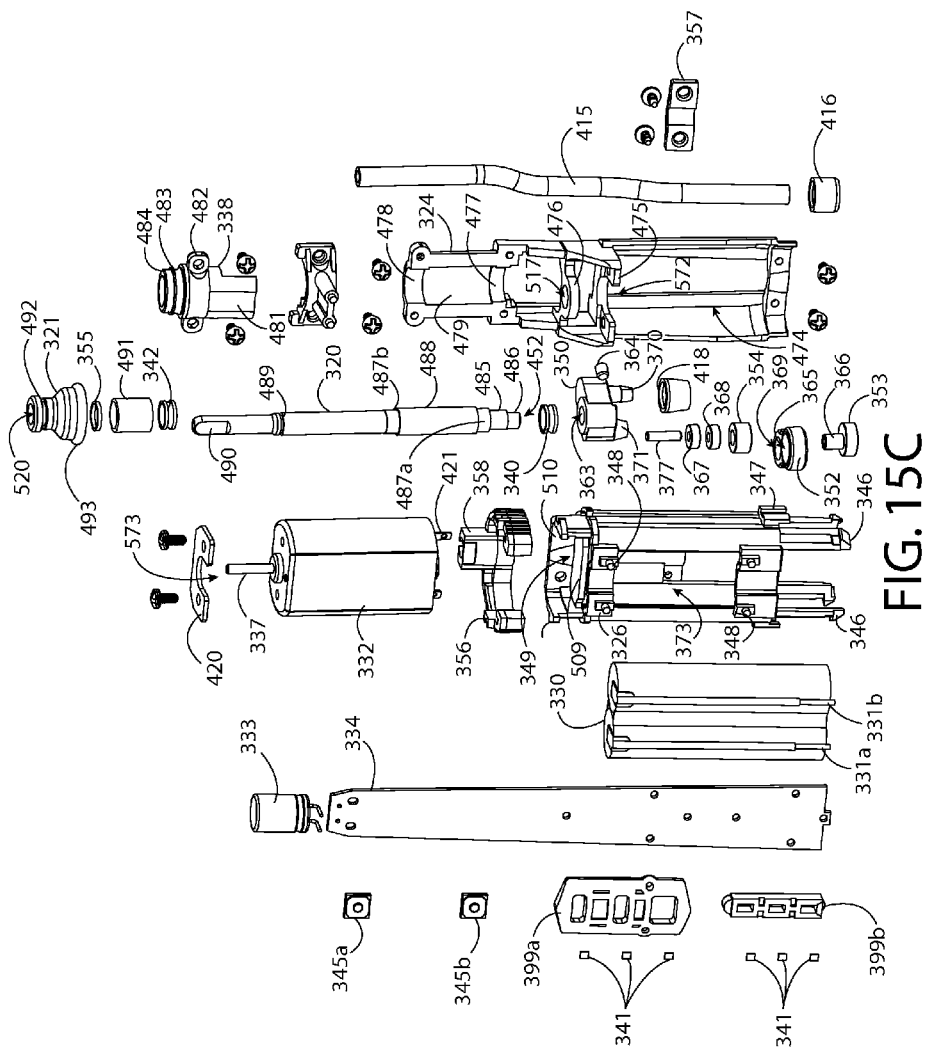

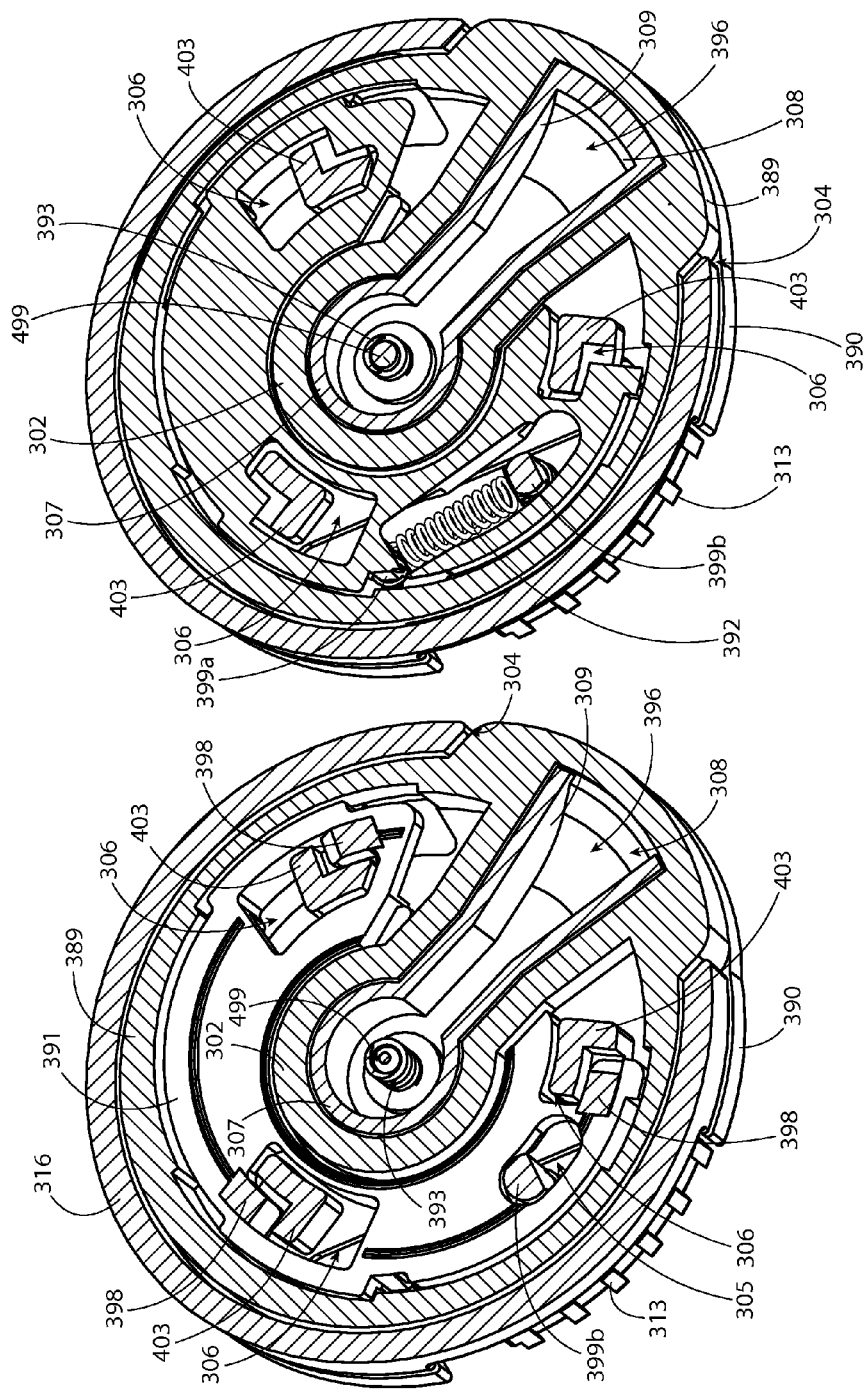

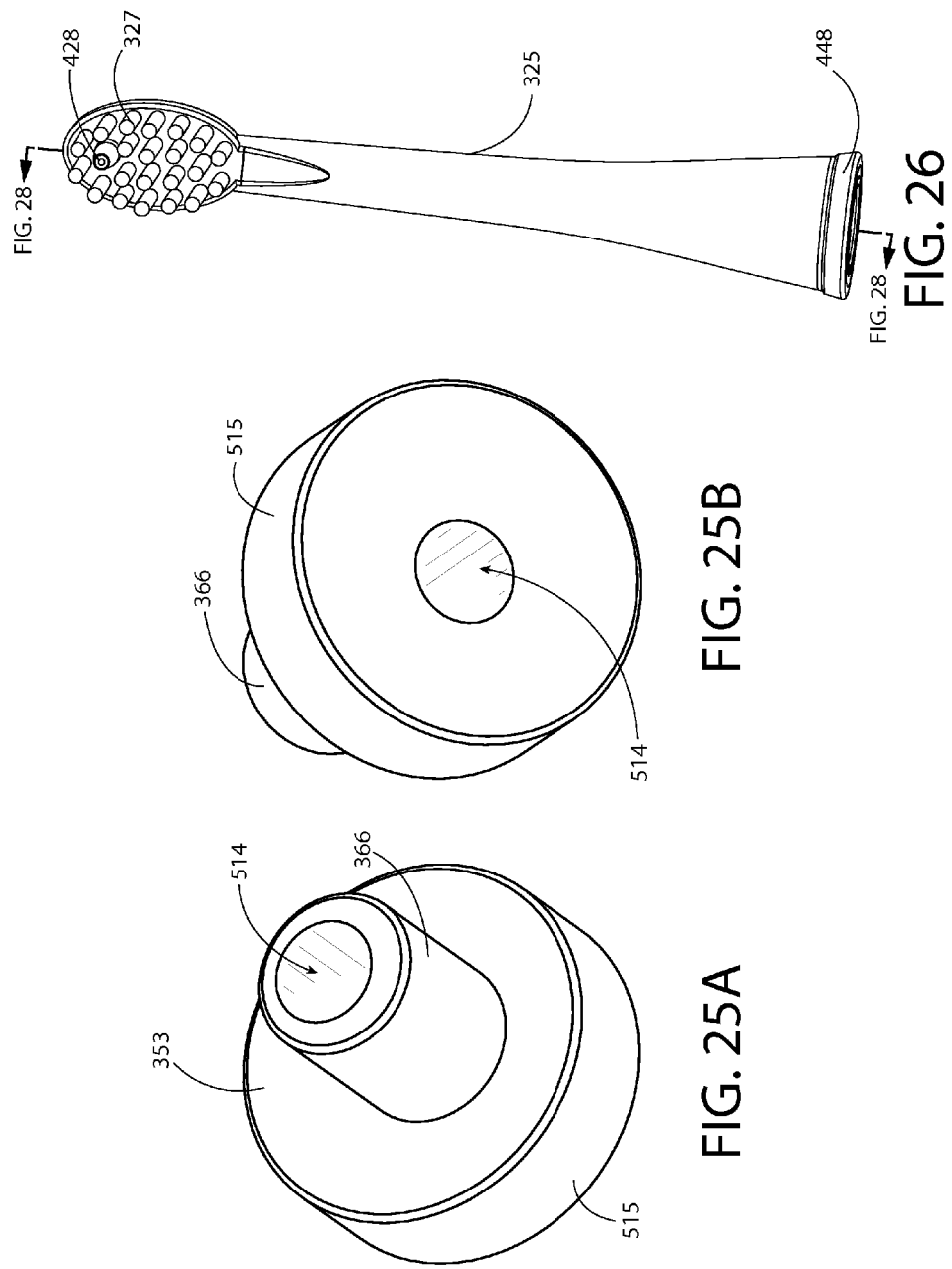

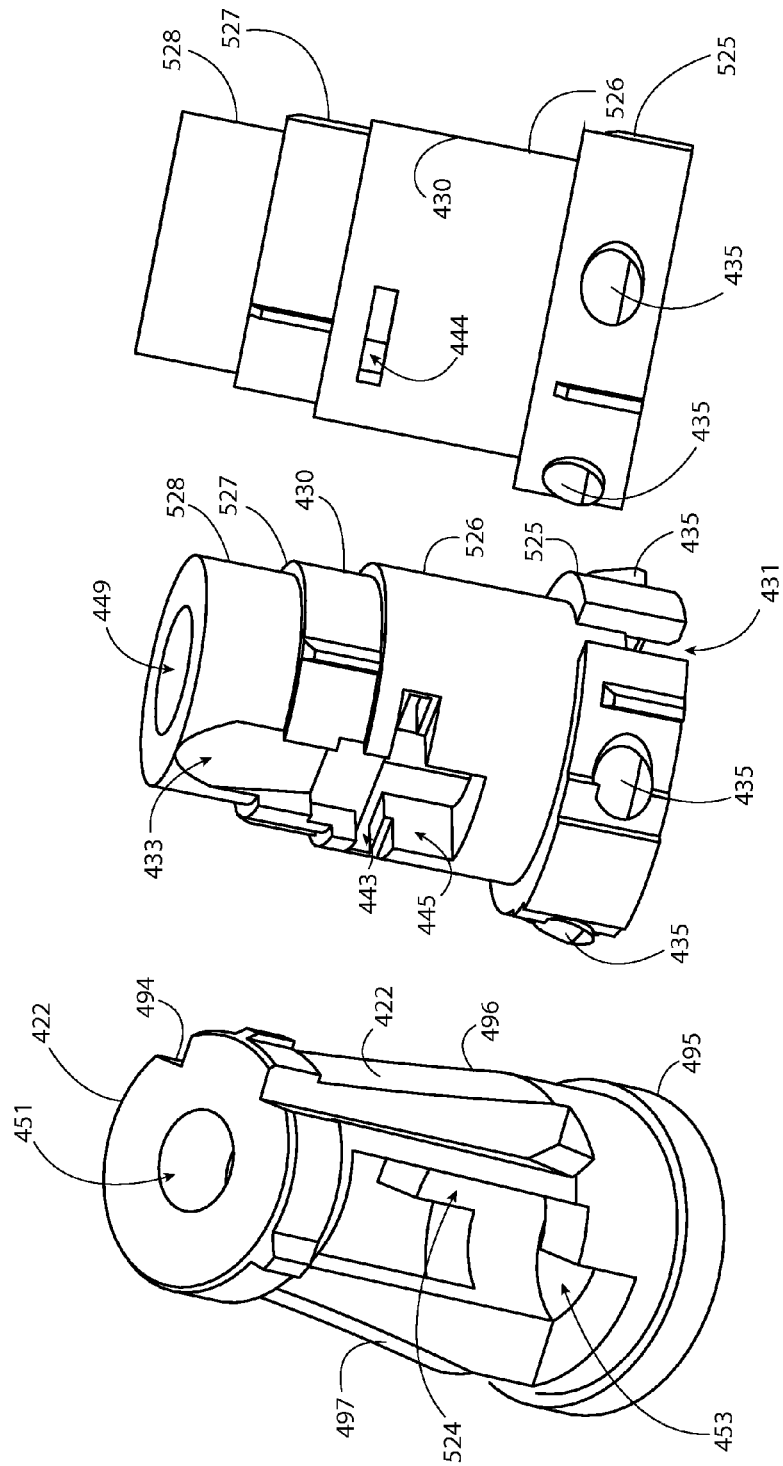

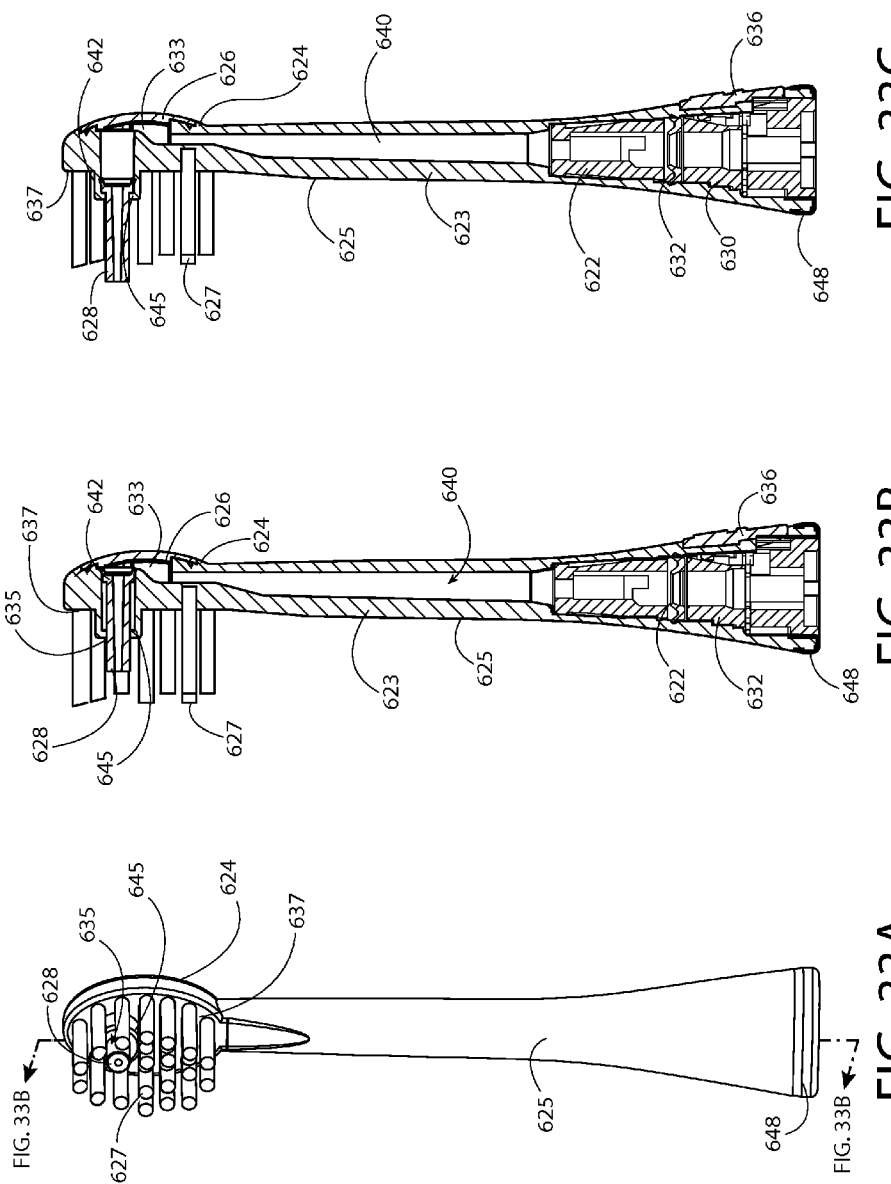

MECHANICALLY-DRIVEN, SONIC TOOTHBRUSH AND WATER FLOSSER

CROSS REFERENCE TO RELATED APPLICATIONS

The present application claims priority pursuant to 35 U.S.C. § 119(e) to U.S. provisional application No. 61/802,121 filed 15 Mar. 2013 entitled "Mechanically driven sonic toothbrush and water flosser," which is hereby incorporated herein by reference in its entirety.

The present application is related to U.S. patent application Ser. No. 13/462,614 filed 2 May 2012 entitled "Mechanically driven sonic toothbrush system."

TECHNICAL FIELD

The present disclosure relates to oral health products. More specifically, the present disclosure relates to sonic toothbrush systems with water flosser features.

BACKGROUND

The state of the art in sonic toothbrush technology centers around drive systems that create a desired oscillating toothbrush output motion by using electro-magnetic drivers and centering return springs to directly create oscillating motion. No continuous input rotation or drivers are involved in these electro-magnetic systems and such electro-magnetic systems have a relatively high production cost.

There are also currently many toothbrushes that provide oscillating output brush motion from continuously rotating input drivers. Such mechanically-driven toothbrushes typically have a reduced manufacturing cost as compared to toothbrushes employing electro-magnetic drivers. However, such rotating systems all perform the oscillating function at speeds well below sonic level. There are no continuously rotating input drive systems that operate at sonic speeds.

Present water jet flossers are standalone units that provide only the pulsing water jet stream using a dedicated, unique handle and flossing tip. There are some devices known as "combo" units that provide toothbrush function along with a water flosser function from a single unit. These devices essentially take a water flosser base unit with a handle and tip assembly, enlarge the base unit, and add a separate toothbrush handle that sits on the enlarged base. Two handles are required to provide both the water flosser and toothbrush functions. There are no systems that provide both the water flosser and toothbrush functions using only one handle assembly and one toothbrush/tip.

The information included in this Background section of the specification, including any references cited herein and any description or discussion thereof, is included for technical reference purposes only and is not to be regarded subject matter by which the scope of the invention as defined in the claims is to be bound.

SUMMARY

A combination toothbrush and water flosser brush head system provides the capability for sonic toothbrush bristle tip movement as well as the delivery of a high pressure, pulsating water flosser fluid stream through an extendable and retractable jet tip nozzle within a single toothbrush head assembly. This brush head assembly is no larger than a single function powered toothbrush brush head. The extension of the jet tip nozzle above the height of the bristle tufts affords the user the ability to accurately locate and control the fluid stream for optimal efficacy without interference from the bristles, while the capability to retract the nozzle allows for unimpeded sonic toothbrush movement without interference from the jet tip nozzle. The brush head system has the capability to perform these functions while delivering the higher fluid pressures necessary for truly effective water flossing.

When the toothbrush tip is attached to the toothbrush shaft of the power handle, the internal water path of the toothbrush tip is sealed to the brush shaft of the power handle. This provides a continuous, sealed water path through the power handle up to and out of the water jet nozzle located between the toothbrush bristles. An external, pulsed water jet generating system is attached to the input portion of the water path within the power handle. When activated, this water jet generating system supplies a stream of pulsed water which passes through the power handle, through the toothbrush tip, and exits from the semi rigid nozzle within the toothbrush head bristle pattern. This pulsed water jet can be directed along the gum line to provide the water flossing effect of a standard, standalone water flosser mechanism.

The water supply connection between the power handle and the water jet generating system may be detachable. This allows the power handle to be untethered from the water supply and water jet base unit, when desired, to be used as a standalone toothbrush. The power handle may have the capability to control only the sonic toothbrush function or both the toothbrush function and the pulsed water jet function.

In one implementation, a toothbrush with combined sonic brushing and water flossing attributes includes an electric motor, a brush tip, a drive assembly, and a fluid passage. The electric motor further includes a drive shaft. When the electric motor is caused to operate, the drive shaft continuously rotates in a single direction. The brush tip supports a brush head on a distal end and defines a fluid conduit therein. The drive assembly is coupled between the drive shaft and the brush tip and is configured to convert rotation of the drive shaft into sonic oscillation of the brush head whereby the brush tip pivots back and forth about a longitudinal axis of the brush tip. The fluid passage is configured to transport fluid from a fluid source external to the toothbrush to the fluid conduit in the brush tip. A portion of the fluid passage is formed within the drive assembly.

In another implementation, a toothbrush with combined sonic brushing and water flossing attributes includes an electric motor, a brush tip, a drive assembly, a fluid passage, a removable base plate, and a valve. The electric motor further includes a drive shaft. When the electric motor is caused to operate, the drive shaft continuously rotates in a single direction. The brush tip supports a brush head on a distal end and defines a fluid conduit therein. The drive assembly is coupled between the drive shaft and the brush tip and is configured to convert rotation of the drive shaft into sonic oscillation of the brush head whereby the brush tip pivots back and forth about a longitudinal axis of the brush tip. The fluid passage is configured to transport fluid from a fluid source external to the toothbrush to the fluid conduit in the brush tip. The removable base plate includes a fluid inlet in fluid communication with the fluid passage and configured for connection with the fluid source. The valve is positioned within the fluid passage and configured to close the fluid passage when the base plate is removed from the toothbrush and configured to open when the base plate is connected to the toothbrush.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIG. 11 is a side isometric view in cross section of the brush tip of the toothbrush/flosser of FIG. 1.

FIG. 15C is an exploded isometric view of the component parts of the toothbrush/flosser of FIG. 12A.

FIG. 19A is an isometric view in cross section of a portion of the removable base taken along line 19A-19A in FIG. 18.

FIG. 19B is an isometric view in cross section of a portion of the removable base taken along line 19B-19B in FIG. 18.

FIG. 25A is a top isometric view of the eccentric cam that mounts on the motor shaft.

FIG. 25B is a bottom isometric view of the eccentric cam of FIG. 25A.

FIG. 26 is an isometric view of a second exemplary implementation of a removable toothbrush/flosser head.

FIG. 30 is an isometric view of an alignment insert for the brush shaft housed within the brush tip.

FIG. 31A is a rear, left side, isometric view of a shaft support for the brush shaft housed within the brush tip.

FIG. 31B is a front isometric view of the shaft support of FIG. 31A.

FIG. 33A is an isometric view of a second exemplary implementation of a removable toothbrush/flosser head.

FIG. 33B is a cross section view of the toothbrush/flosser head of FIG. 33A taken along line 33B-33B in FIG. 33A with the flosser tip in a retracted position.

FIG. 33C is a cross section view of the toothbrush/flosser head of FIG. 33A similar to the section taken along line 33B-33B in FIG. 33A with the flosser tip in an extended position.

DETAILED DESCRIPTION

Figure 1:
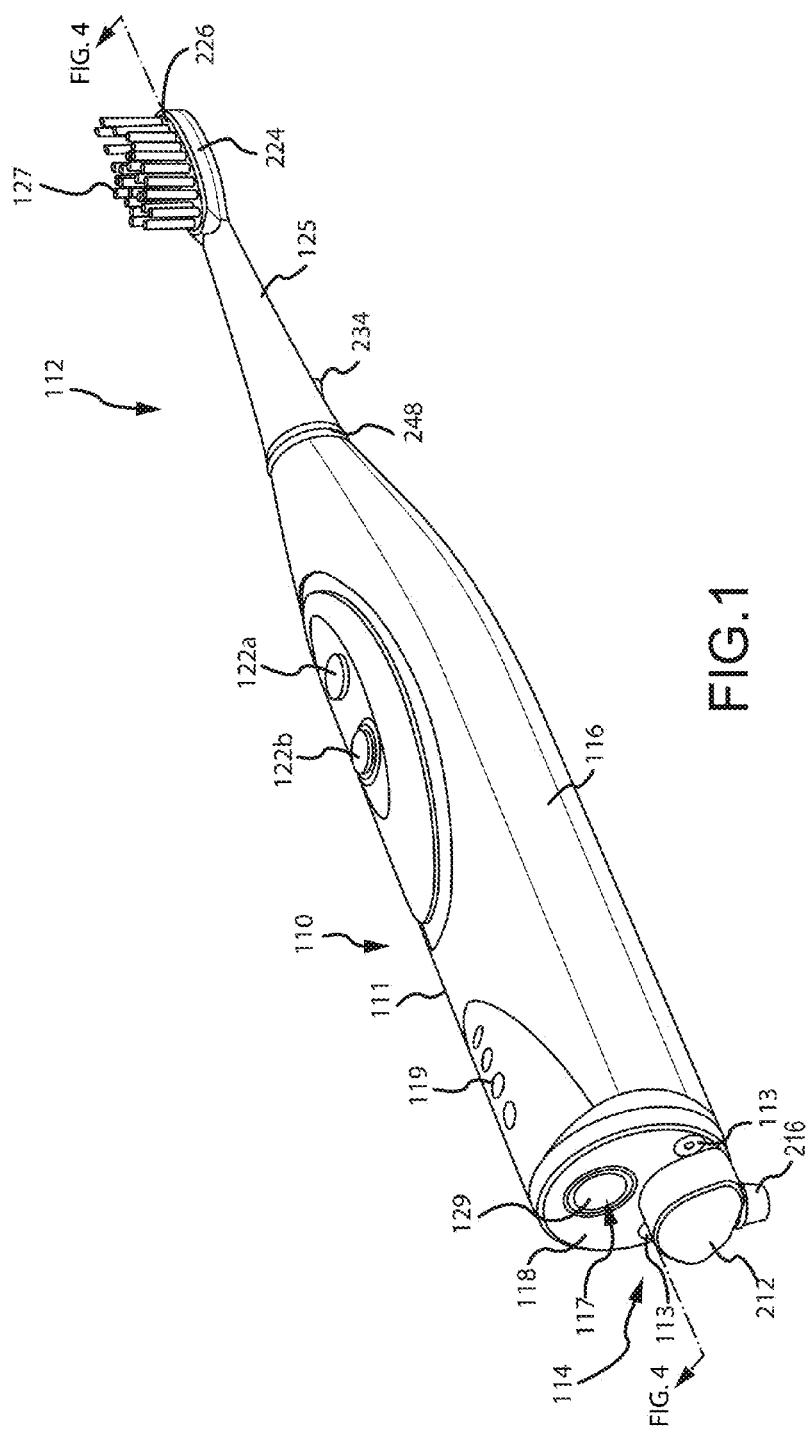
FIG. 1 is an isometric view of an exemplary implementation of a combination mechanically-driven, sonic toothbrush and water flosser.

Several exemplary embodiments of a mechanically-driven, sonic toothbrush system, with a water flossing tip, are disclosed herein. The sonic toothbrush/flosser system makes use of a continuously rotating input driver (e.g., a DC or AC motor) that operates a balanced linkage system to change the continuous rotation of the input driver into a desired oscillating output motion, which drives the attached toothbrush head at a sonic speed or speeds.

Use of DC drive motors for input drive motion may result in a lower production cost of the mechanically-driven, sonic toothbrush/flosser system than the current electro-magnetic sonic toothbrush systems as well as the use of relatively inexpensive molded plastic components.

The sonic toothbrush/flosser systems disclosed herein may provide a continuously rotating input drive system that provides oscillating, sonic-speed toothbrush output motion with an extremely low level of mechanical vibration and noise. Also, the exemplary mechanically-driven, sonic toothbrush systems disclosed herein provide a sonic toothbrush system at a reduced production cost.

Some embodiments of a mechanically-driven sonic toothbrush may be configured for attachment to a water flosser base unit. In these embodiments, the sonic toothbrush may include a fluid inlet for connection with a fluid tube from the flosser base unit. A fluid flow conduit is provided through the handle of the sonic toothbrush and also through a portion of the oscillation drive motion mechanism. The fluid flow conduit exits through a replaceable brush tip that carries an irrigator nozzle mounted within the bristles on the brush head. When the brush tip is attached to the output shaft of the handle, the internal water path of the brush tip is sealed with the outlet of the fluid flow conduit through the output shaft. This provides a continuous, sealed water path through the power handle up to and out of the water jet nozzle located between the toothbrush bristles.

An external, water flosser base system that generates a pulsed water jet is attached to an inlet port on the handle via a hose. When activated, this water jet generating system supplies a stream of pulsed water which passes through the handle, through the rush tip, and exits from the nozzle within the toothbrush head bristle pattern. This pulsed water jet can be directed along the gum line to provide the water flossing effect of a standard, standalone water flosser. The water flosser base unit pumps water or other fluid from a reservoir in the base unit, through the connection hose, through the fluid pathway in the sonic toothbrush, and out the irrigator tip in the brush head to provide a water flossing device in combination with the benefits of a sonic toothbrush.

The water supply connection between the handle and the water flosser base system is detachable. This allows the handle to be untethered from the water flosser, when desired, to be used as a standalone toothbrush. The handle has the capability to control both the toothbrush function and the pulsed water jet function. This system thereby provides two capabilities, a sonic toothbrush as well as a water jet, water flosser, from just one convenient handle.

The handheld toothbrush/flosser disclosed herein provides a much more compact, efficient, and less costly "combination" toothbrush/water flosser unit. With only one handheld device, considerable space is saved by not having to accommodate a second handle, and the space utilization can be more efficient. In addition, a single handle affords the potential for the combined system to be more economical. The detachable water source also allows the power handle to function untethered as a toothbrush for travel or when the brushing function is desired to be more portable. The single handle has the capability to control both the toothbrush function as well as the pulsed water jet function. In addition, a single, replaceable toothbrush head provides for both the brushing function as well as a directable nozzle for the pulsed water jet function without the requirement for separate, dedicated attachments for each of the two function.

On exemplary implementation of a combination mechanically-driven, sonic toothbrush and water flosser 110 is presented in FIGS. 1-11. As shown in FIG. 1, the combination sonic toothbrush and flosser 110 is composed of a handle 111 and a removable brush tip 125. The brush tip 125 may extend distally to form a brush head 224 housing a bristle insert 226 from which a plurality of bristle tufts 127 may extend. For purposes of reference, the distal end of the toothbrush/flosser 110 may be referred to as the brush end 112 and the proximal end may be referred to as a base end 114.

The handle 111 is defined by a housing 116 that generally extends between the base end 114 and the brush end 112. The housing 116 may be generally cylindrical in shape to ergonomically fit in the hand of a user, but it may be formed in any other desirable ergonomic shapes. The cylindrical shape may taper in the direction of the brush end 112 approximately one third the length of the housing 116 from the brush end 112. The housing 116 may expose one or more actuation buttons 122a, 122b to activate and control the functionality of the toothbrush/flosser 110. A face plate 123 may be supported on the housing 116 in a region extending about the control buttons 122a, 122b as either a separate plate or as an overmolded surface on the housing 116. The housing 116 may further expose one or more status indicators 119, e.g., an LED, for indicating to a user a mode or status of operation of the toothbrush/flosser 110. Exemplary modes may be low speed, high speed, or water flosser mode. Exemplary status indications may be low battery, charging, and fully charged battery.

The base end 114 of the housing 116 may be enclosed by a generally flat base cap 118 upon which the toothbrush/flosser 110 may be stood upright on a planar surface, such as a countertop. Additionally, the base end 114 of the toothbrush/flosser 110 may be placed within an inductive charging unit (not shown) between brushing and flossing sessions to charge internal batteries that provide power to drive the motor for the sonic toothbrush as further described herein. The base cap 118 may define an opening 117 to expose an inner wall of a coil bobbin 129 that may be placed upon an induction post of the charging unit. The base cap 118 may be attached to the housing 116 (or a chassis structure contained within the housing and further described below) with one or more screws 113 or other appropriate fastening devices. In order to provide a water flosser feature, an external connector 212 may be provided for coupling at one end with the base cap 118 and at another end with a fluid hose from a separate water flosser base unit (not shown).

Figure 2:
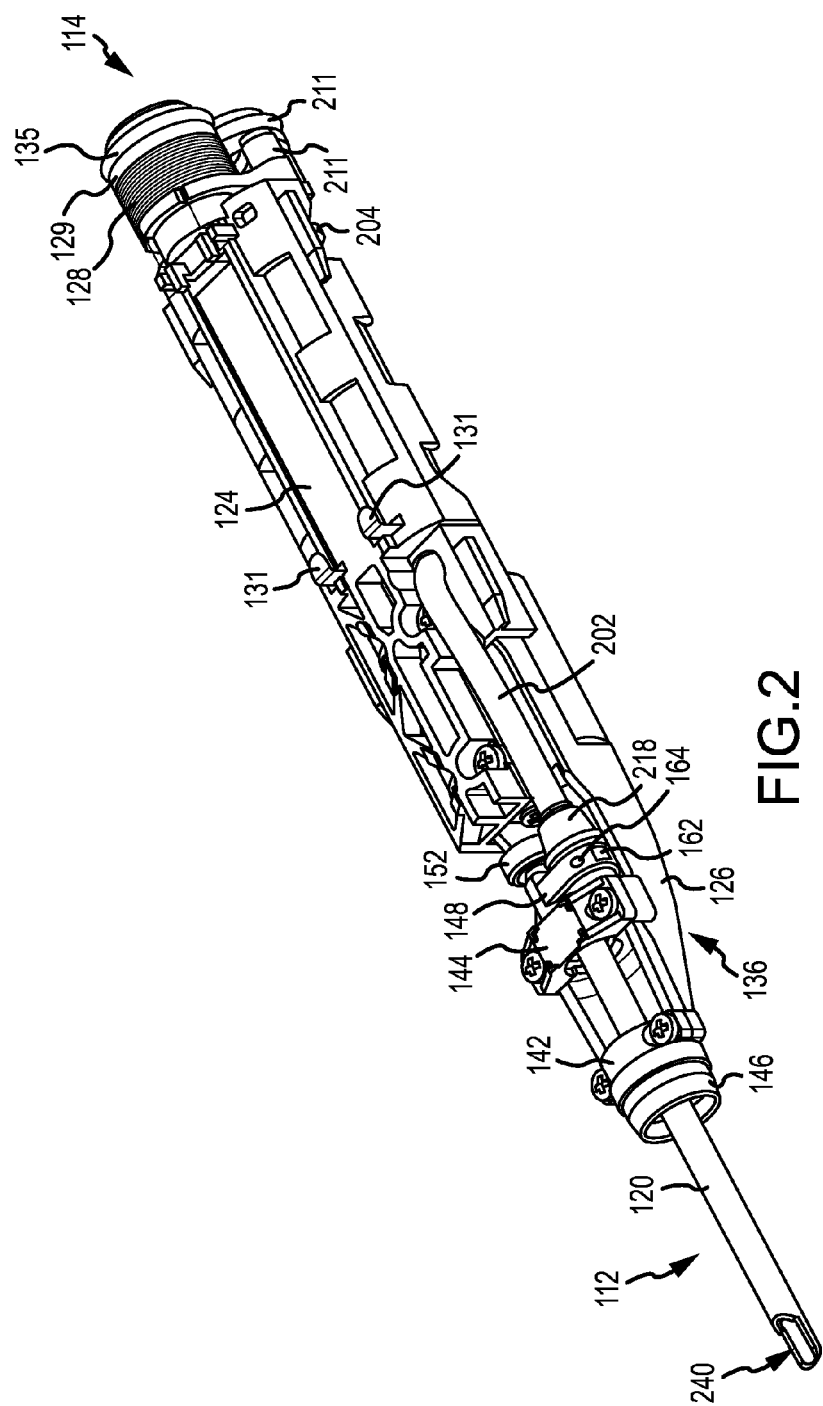
FIG. 2 is a front, top isometric view of the toothbrush/flosser of FIG. 1 with the housing, base cap, and brush tip removed.
Figure 3:
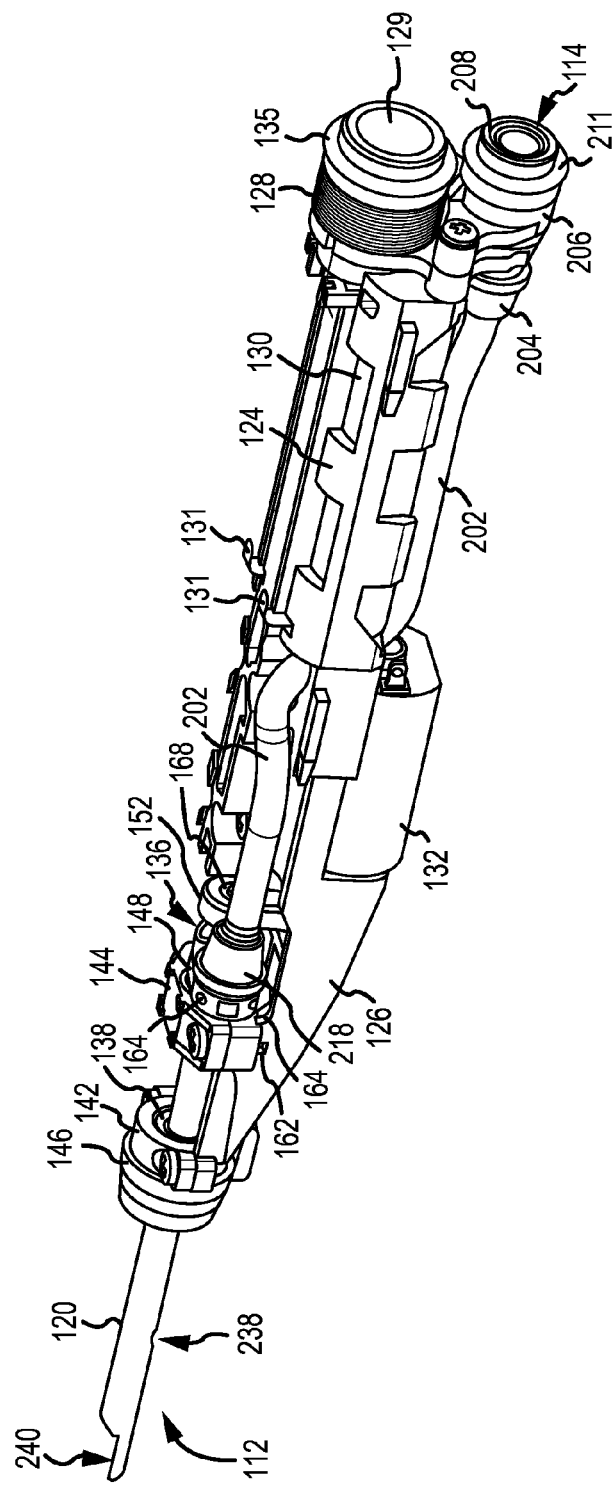
FIG. 3 is a rear, bottom isometric with the housing, base cap, and brush tip removed.
Figure 4:
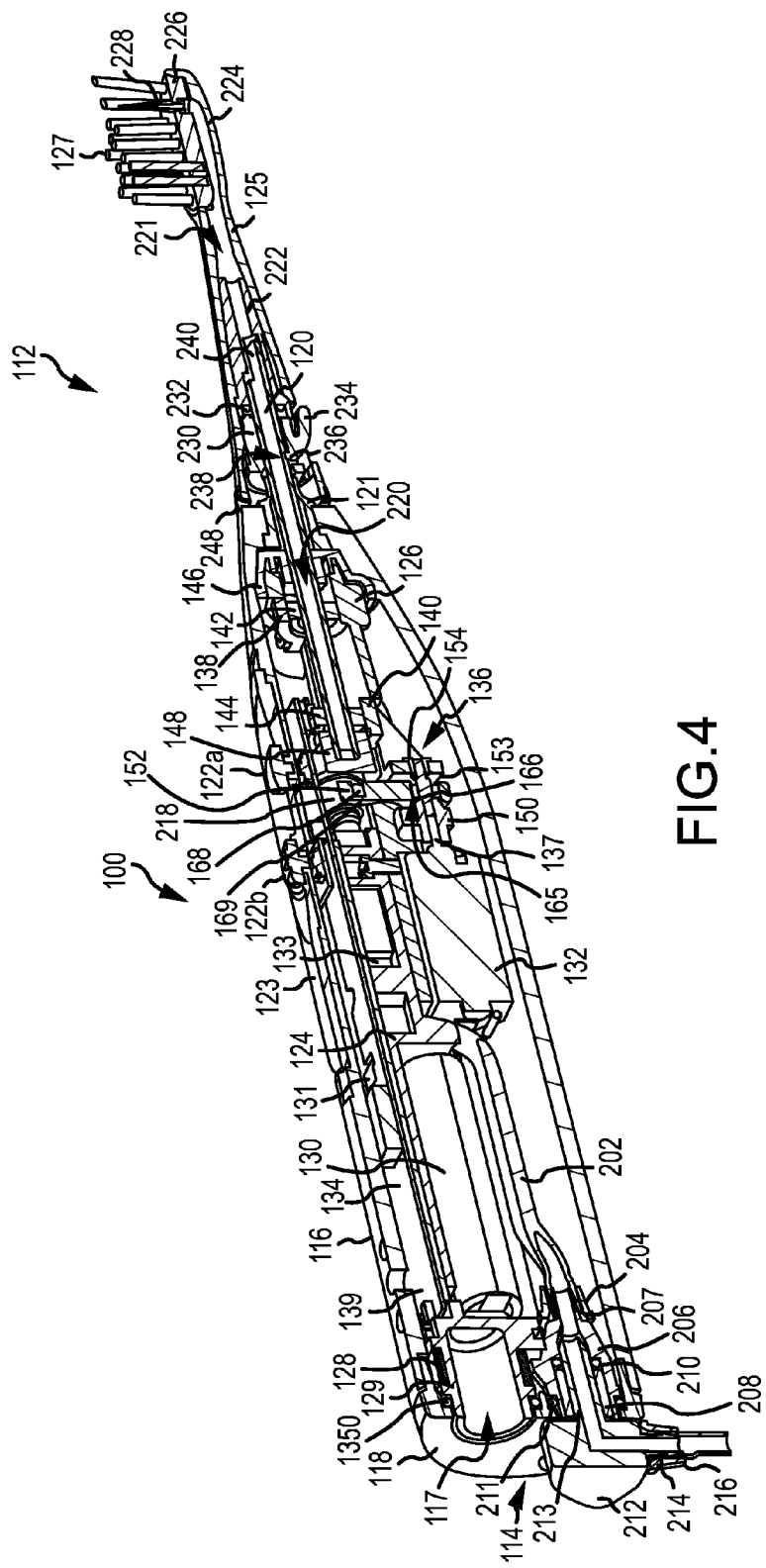
FIG. 4 is a side isometric view in cross section of the toothbrush/flosser of FIG. 1 taken along line 4-4 in FIG. 1.

FIGS. 2 and 3 are, respectively front top and rear side isometric views of the toothbrush/flosser 110 of FIG. 1 with the housing 116, base cap 118, and brush tip 125 removed to reveal the inner structures of the toothbrush/flosser 110. FIG. 4 is a side isometric view in cross section of the toothbrush/ flosser 110 with the housing 116, base cap 118, and brush tip 125 intact. A brush shaft 120 extends distally out of the housing 116 at the brush end 112 from the drive assembly 136 further discussed below. A shaft seal 121 extends about the shaft 120 between the housing 116 and the shaft 120 at the brush end 112 and is configured to allow the shaft 120 to oscillate while preventing the ingress of fluids into the interior of the housing.

Figure 10:
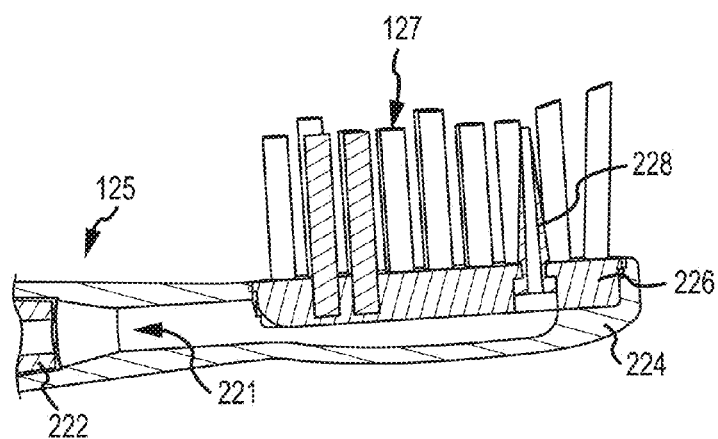
FIG. 10 is an enlarged side elevation view in cross section of the brush head portion of the brush tip of the toothbrush/flosser of FIG. 1.

The toothbrush/flosser 110 may be built upon and around an internal support structure formed by a rear chassis 124 extending toward the base end 114 and a drive bracket 126 extending toward the brush end 112. A rechargeable battery pack 130 is supported in a pocket of the rear chassis 124. An electric DC motor 132 is supported on the rear chassis 124 near the interface between the rear chassis 124 and the drive bracket 126. The motor 132 is electrically coupled to the battery pack 130 via a printed circuit board 134 supported across the chassis 124 and the drive bracket 126 with a damper sheet 133 of vibration damping material placed in between. As best seen in FIG. 10, the battery pack 130 is recharged by an induction coil 128 that is wound around a bobbin 129 that is mounted to the rear end of the chassis below the battery pack 130 and on the interior side of the bottom cap 118. The induction coil 128 connected to the battery pack 130 via the circuit board 134 to allow the circuit board 134 to appropriately condition the power input to the battery pack 130. An aperture 117 in the bottom cap 118 is aligned with a cavity within the bobbin 129 and allows the toothbrush/flosser 110 to be placed upon an induction post of a charging unit to inductively charge the battery pack 130 via the induction coil 128. A coil seal 135, e.g., and O-ring, may be positioned between the bobbin 129 and the base cap 118 in order to prevent water or other fluid from infiltrating the handle 111 from the base end 114 at the interface of the bobbin 129 and the base cap 118.

Control circuits on the circuit board 134 are actuated via the control buttons 122a, 122b to cause the motor 132 to operate at different states (e.g., on, off, high speed, low speed, etc.). In one embodiment, the toothbrush/flosser 110 may be electrically connected with the base water flosser unit and the control buttons 122a, 122b may control the actuation and operation of the base water flosser unit per the design of the circuits on the circuit board 134. In an alternate embodiment, the circuit board 134 may be provided with a radio frequency (RF) transmitter or transceiver to wirelessly communicate with and control a water flosser base unit to provide control commands to the base unit. In one exemplary embodiment the circuit board 134 and the base unit may both be equipped with Bluetooth transceivers. In another exemplary embodiment, the wireless connection may be an infrared communication link.

Figure 5:
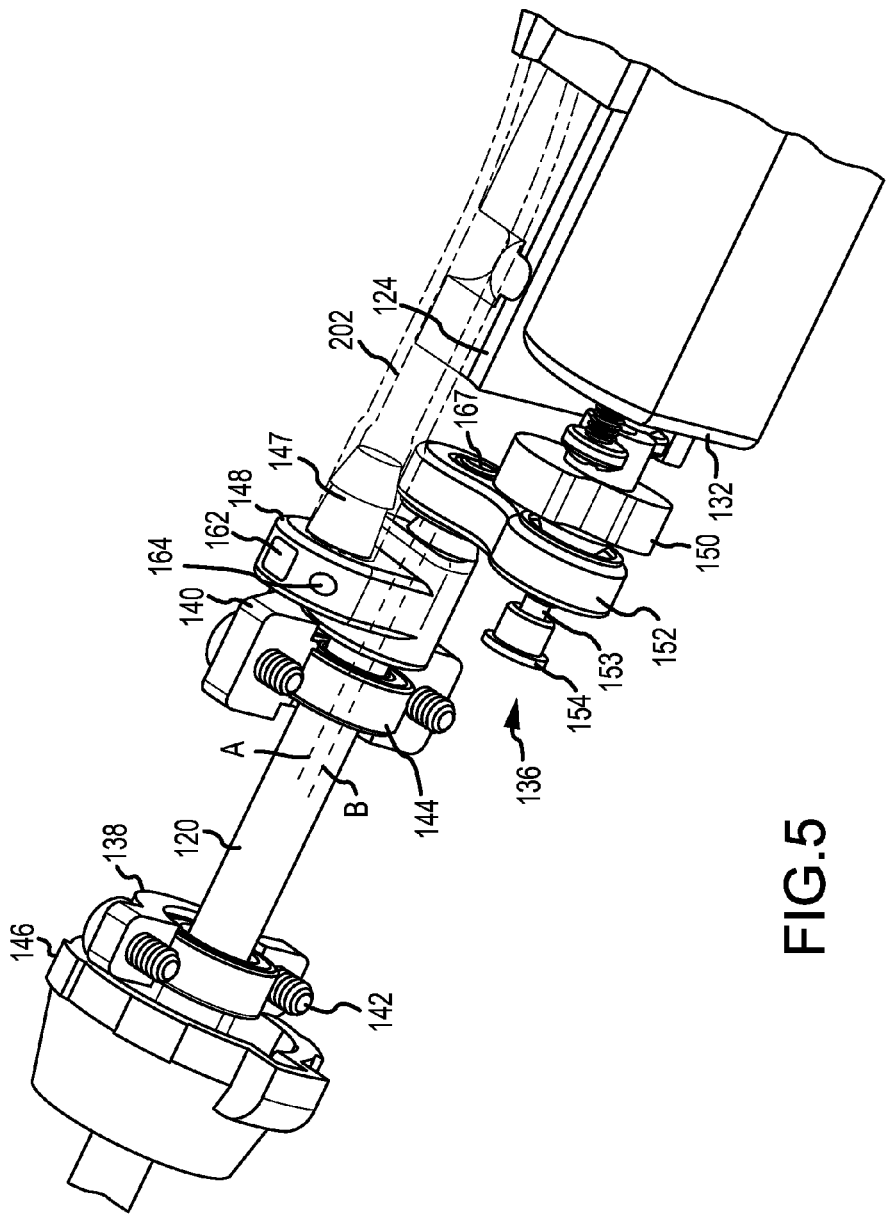
FIG. 5 is an enlarged bottom isometric view of the drive assembly of the toothbrush/flosser of FIG. 1 with the housing, brush tip, drive bracket, and rear chassis removed and the irrigator hose shown in phantom for clarity.
Figure 6:
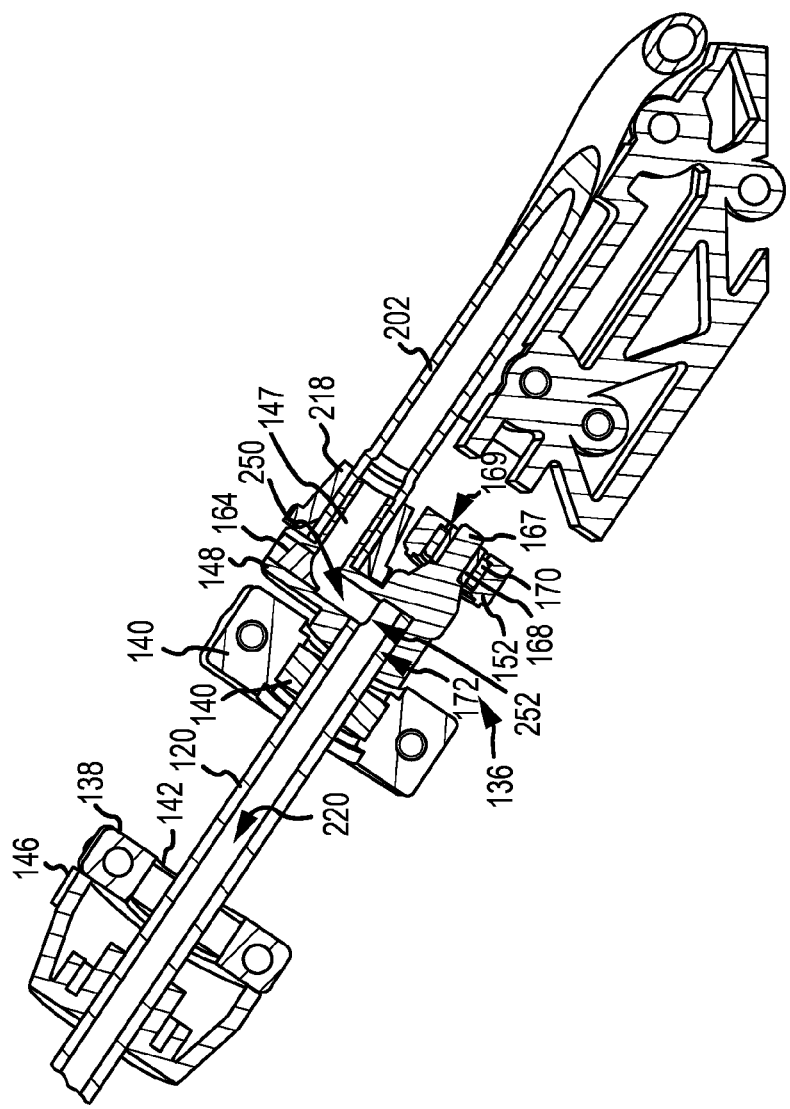
FIG. 6 is an enlarged bottom isometric view in cross section of the drive assembly of the toothbrush/flosser of FIG. 1 with the housing, brush tip, drive bracket, and rear chassis removed for clarity.

As depicted in FIGS. 2 and 3, the drive assembly 136 is supported within a pocket of the drive bracket 126 at the interface of the drive bracket 126 and the rear chassis 124. The drive assembly 136 mechanically couples the output shaft 137 of the motor 132 to the brush shaft 120 to cause the brush shaft 120 to oscillate at sonic speeds when the motor 132 causes its output shaft 137 to continuously rotate. As illustrated in FIGS. 4-7, the drive bracket 126 may support a front bearing bracket 138 and a rear bearing bracket 140 that, in combination with the drive bracket 126 form front and rear pillow blocks that respectively hold a front bearing 142 and a rear bearing 144. The bearings 142, 144 may be ball or roller type bearings in circular races through which the brush shaft 120 extends. The bearing 144 of the rear bearing bracket 140 supports the rear end of the brush shaft 120, and the bearing ring 142 of the front bearing bracket 138 supports the brush shaft 120 near the midpoint of the brush shaft 120. As best seen in FIGS. 5-6, an isolator damper 146 is mounted on the drive bracket 126 and surrounds the brush shaft 120 in front of the front bearing bracket 138 to vibrationally isolate the moving components of the drive assembly 136 from the housing 116.

Figure 7:
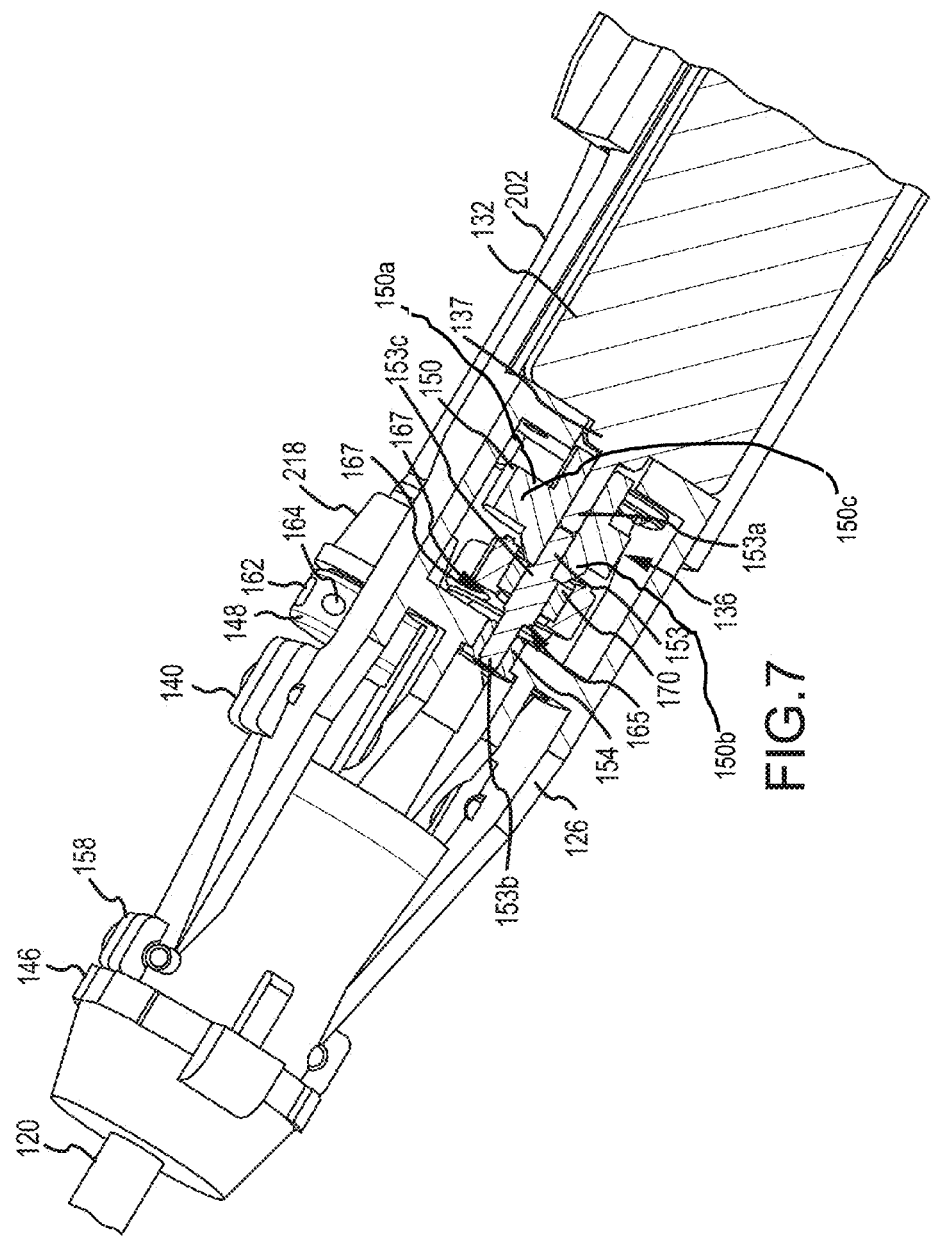
FIG. 7 is an enlarged bottom isometric view in cross section of the drive assembly of the toothbrush/flosser of FIG. 1 with the housing and brush tip removed for clarity.

As further shown in FIGS. 4-7, the drive assembly 136 is mechanically coupled to an output shaft 137 of the motor 132 for operation. As best seen in FIG. 7, the motor output shaft 137 extends from the motor 132 into a through-bore in a motor crank arm 150 to fixedly connect with the motor crank arm 150 and form a rear end of the drive assembly 136. An eccentric pin 153 extends from the front end of through-bore of the motor crank arm 150 in which a rear shaft 153a of the eccentric pin 153 is fixedly attached. A cam portion 153c in a middle section of the eccentric pin 153 extends through a lower aperture 165 in a dog bone coupler 152. A front shaft 153b of the eccentric pin 153 extends distally from the cam portion 153c toward the brush end 112 and is received in a support bushing 154 mounted within the framework of the drive bracket 126. The front shaft 153b and the rear shaft 153a may be of the same diameter and are axially aligned. The cam portion 153c may have a center of mass offset from the axis of alignment of the rear and front shafts 153a, 153b and may be of a larger diameter than the diameter of the rear and front shafts 153a, 153b and thus have a pivot axis offset, but parallel to, the common pivot axis of the rear and front shafts 153a, 153b. The cam portion 153c may be supported in the lower aperture 165 of the dog bone coupler 152 by a cam bearing 166.

A rocker arm 148 may be positioned in front of an upper aperture 169 of the dog bone coupler 152. The rocker arm 148 may be formed with a pivot shaft 167 that extends from a rear surface proximally toward the base end 114 through the upper aperture 169 in the dog bone coupler 152 as best seen in FIG. 6. The pivot shaft 167 may be supported in the upper aperture 169 by a combination of a pivot sleeve 168 and a bushing 170 to allow the pivot shaft 167 of the rocker arm 148 to freely pivot with low resistance within the upper aperture 169. In some embodiments, the rocker arm 148 may be made of a molded plastic material as further described below. As such, the pivot sleeve 168 may be made of a metal to provide for a more resilient and smooth pivot joint with the bushing 170. A front surface of the rocker arm 148 may define an aperture or cavity 172 into which the brush shaft 120 is inserted and mechanically connected. The shaft cavity 172 is aligned with an axis A parallel to, but offset from, an axis B of the pivot shaft 167 on the opposite side of the rocker arm 148. Through this linkage the motor crank arm 150 is thereby coupled with the rocker arm 148 via the dog bone coupler 152 and further to the brush shaft via the rocker arm 148.

In this implementation, the crank arm 150 may be amorphously shaped and sized as seen in FIG. 5. As shown in FIG. 7, the crank arm 150 may have a cylindrical rear receiver section 150a extending toward the base end 114 that receives the output shaft 137 of the motor 132. The thickness of the wall of the rear receiver section 150a may be designed to accommodate a set screw (not shown) to tightly hold the output shaft 137 within the crank arm 150. The crank arm 150 may further have a front receiver section 150b extending toward the brush end 112 that receives the rear shaft 153a of the eccentric pin 153. The front receiver section 150b may be formed as a rounded frustum with the narrow diameter portion adjacent the cam bearing 166 in order to minimize the possibility of interference between the crank arm 150 and the cam bearing 166. The rear portion of the front receiver section 150*b* may have a thicker wall and may be designed to accommodate a set screw (not shown) to tightly hold the rear shaft 153*a* of the eccentric pin 153 within the crank arm 150.

A balance section 150*c* of the crank arm 150 may be formed between the rear receiver section 150*a* and the front receiver section 150*b* and may be of an amorphous shape that is tuned to help balance the oscillations in the drive assembly 136 to reduce noise and vibration in the drive assembly 136. For example, as shown in FIG. 5, the crank arm may be formed of two lobes of different sizes with scooped sidewalls in between. In this implementation, the crank arm 150 is not provided with cavities for the addition of various additional balance weights (although such is possible).

In this implementation, however, the rocker arm 148 may be formed with one or cavities to introduce balance weights 162 to improve the balance of the drive system 136 to reduce noise and transmission of extraneous vibration to the handle 111. The balance weights 162 may be held in place by one or more plug pins 164 as shown in FIGS. 5-7.

As best shown in FIG. 5, once the motor 132 is actuated by the control button 122, the motor drive shaft 137, which is fixedly received in the through-bore of the motor crank arm 150, rotates continuously in a single rotational direction until the control button 22 is depressed to deactivate the motor 132 and stop its rotation. The rear shaft 153*a* of the eccentric pin 153 is fixedly received in the front end of the through-bore of the motor crank arm 150. The enlarged cam portion 153*c* of the eccentric pin 153 is rotationally received within the cam bearing 166, which is fixedly received in the lower aperture 165 of the dog bone coupler 152. The front shaft 153*b* of the eccentric pin 153 is rotationally received in the support bushing 154 fixedly mounted in the drive bracket 126. Thus, the rotating motor drive shaft 137 causes the motor crank arm 150 and the eccentric pin 153 to rotate in the same direction. Thus, the cam portion 153*c* and the front shaft 153*b* of the eccentric pin 153 rotate in the same direction within the cam bearing 166 and the bushing 154, respectively. The rotation of the cam portion 153*c* causes the dog bone coupler 152 to move back and forth or, in other words, oscillate, primarily in an oblong or linear orientation.

The pivot pin 167 extending from the rocker arm 148 is pivotally or oscillatingly received in the pivot sleeve 168 and bushing 170, which is fixedly received in the upper aperture 169 of the dog bone coupler 152. Thus, the back and forth or oscillating displacement of the dog bone coupler 152 causes the rocker arm 148 to displace back and forth or oscillate about an axis passing through the center of the rocker arm 148. As a result, the brush shaft 120, which is mounted in the shaft cavity 172 in the rocker arm 148, is caused to pivot back and forth or oscillate about the longitudinal axis of the shaft 120.

In the embodiment of FIGS. 1-11, the toothbrush/flosser device 110 of the delivers water or other fluid through the device 110 to an irrigator tip 228 provided among the bristles 127 within the brush head 224. As such, the brush shaft 120 in this implementation is hollow and defines a fluid channel 220 therethrough. The entire fluid pathway through the toothbrush/flosser device 110 from the base end 114 to the brush end 112 is depicted in FIGS. 2-11.

Figure 8:
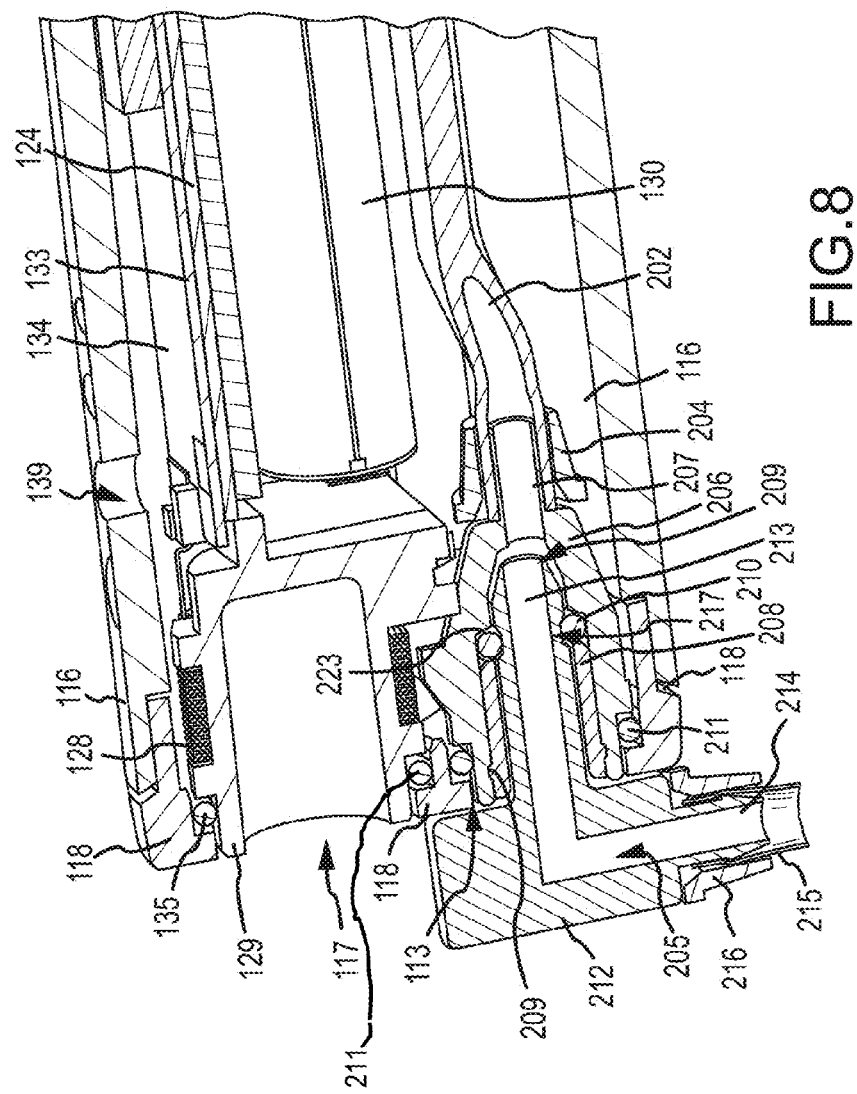
FIG. 8 is an enlarged side isometric view in cross section of the base end of the toothbrush/flosser of FIG. 1.
Figure 9:
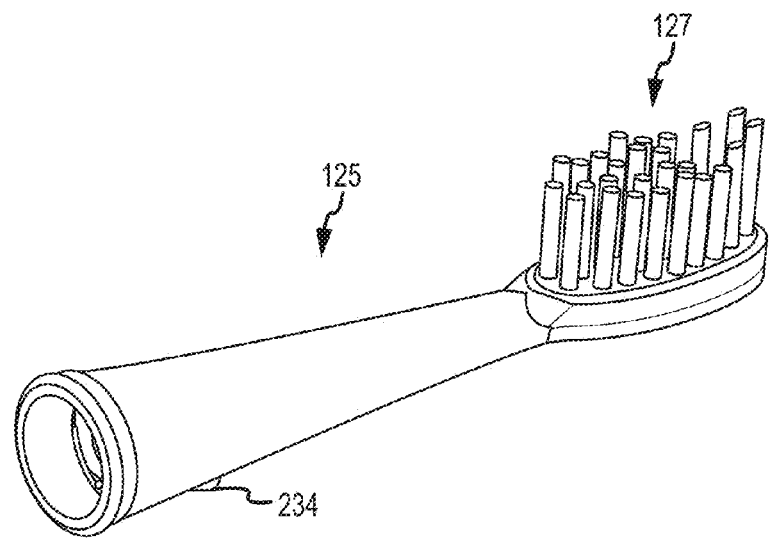
FIG. 9 is an isometric view of the brush tip of the toothbrush/flosser of FIG. 1.

As shown in detail in FIG. 8, the toothbrush/flosser device 110 may be connected with an irrigator hose 215 from a water flosser base unit (not shown) having a fluid reservoir and pump to provide a pulsating, high pressure water flow to the irrigator tip 228. The irrigator hose 215 is connected to an external connector 212 that may be removably connected to toothbrush/flosser device 110 within an irrigator socket 206 mounted within the base end 14 of the housing 116 and extending through an aperture in the base cap 118 adjacent the bobbin aperture 117. A socket seal 211 (e.g., an O-ring) may be positioned between the irrigator socket 206 and the base cap 118 in order to prevent water or other fluid from infiltrating the handle 111 from the base end 114 at the interface of the irrigator socket 206 and the base cap 118.

The external connector 212 defines a fluid flow channel 205 from an inlet end formed as a hose barb 214 for attachment to the irrigator hose 215 to an outlet end formed as a hollow tube socket connector 213 that is inserted within a cavity 209 defined within the irrigator socket 206. In one exemplary implementation, the hose barb 214 and the socket connector 213 are arranged perpendicular to each other on the external connector 212 such that the fluid channel 205 bends from the inlet at the hose barb 214, which is oriented radially with respect to the longitudinal axis of the toothbrush/flosser device 110, to exit through the socket connector 213 in which the fluid channel 205 is oriented parallel to the longitudinal axis of the toothbrush/flosser device 110.

A locking sleeve 216 may be placed over the irrigator hose 215 around the hose barb 214 to ensure a mechanically secure and fluid tight seal. A fluid tight seal is ensured between the irrigator socket 206 and the socket connector 213 within the cavity 209 by a connector seal 210 (e.g., an O-ring) that seats against a shoulder 223 in the irrigator socket 206. The socket connector 213 may define an annular recess 217 about an outer wall that interfaces with the connector seal 210, helping to provide a mechanical interface and friction fit between the socket connector 213 and the irrigator socket 206. The connector seal may be retained within the cavity 209 of the irrigator socket 206 by a retainer sleeve 208 that presses the connector seal 210 against the shoulder 223. The retainer sleeve 208 may mechanically interface with the irrigator socket 206 via a snap or detent connection between an annular rib 219 formed on the outer diameter of the retainer sleeve 208 and a corresponding annular recess 219 formed in the inner diameter of the irrigator socket 206 (or vice versa).

The external connector 212 interfaces with the irrigator socket 206 in a fluid-tight, friction fit, but is also easily removable upon application of rearward axial force in order to disconnect the toothbrush/flosser device 110 from the irrigator hose 215, which fits tightly over the hose barb 214 of the external connector 212 and is difficult to remove. The external connector 212 may be removed to place the toothbrush/flosser device 110 in an inductive charging unit or to provide mobility for toothbrush/flosser device 110 (e.g., to take the device 110 on a trip and use it only as a mechanically-drive sonic toothbrush while away from the water flosser base unit).

Figure 17:
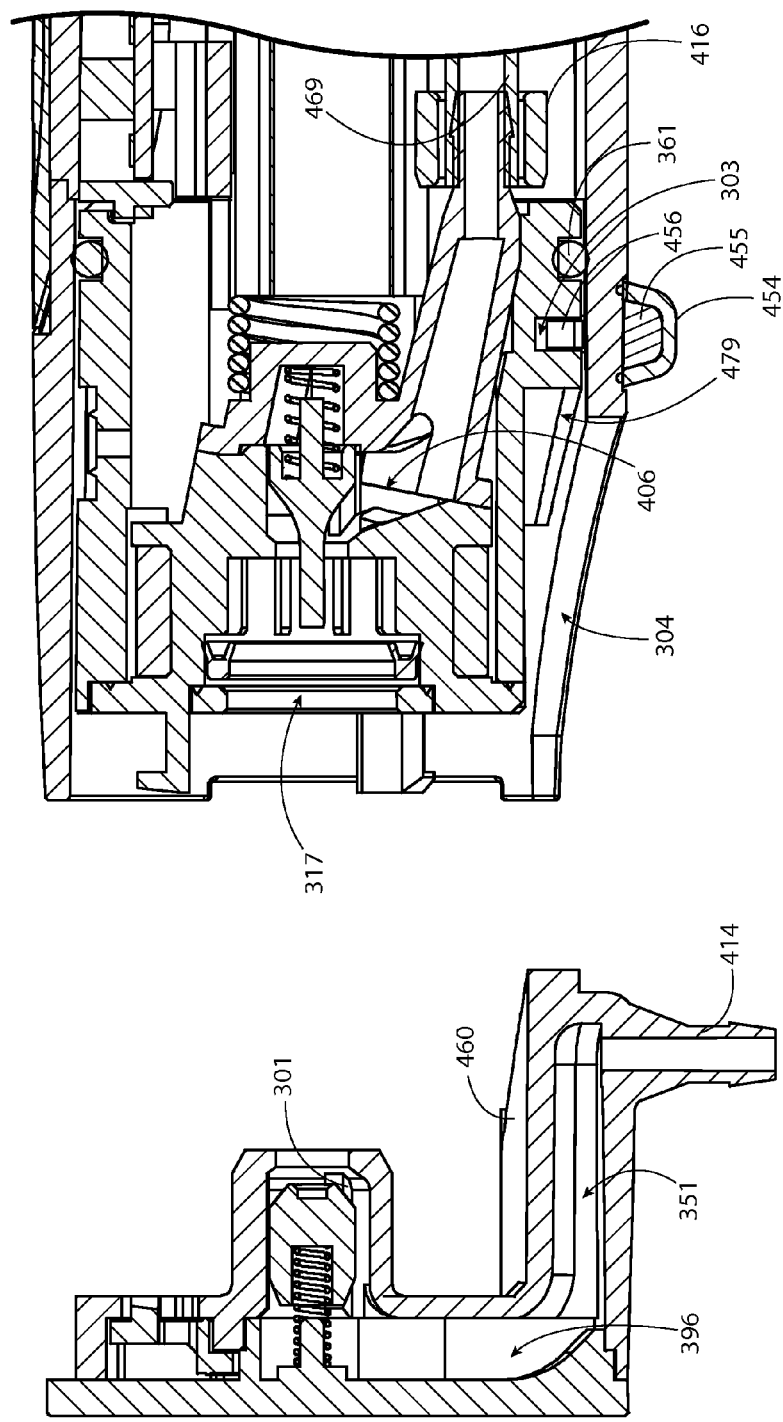
FIG. 17 is an enlarged, right side, isometric view in cross section of the toothbrush/flosser of FIG. 12A taken along line 14-14 in FIG. 12A detailing the detachable base in a removed configuration and operation of the poppet valves.
Figure 18:
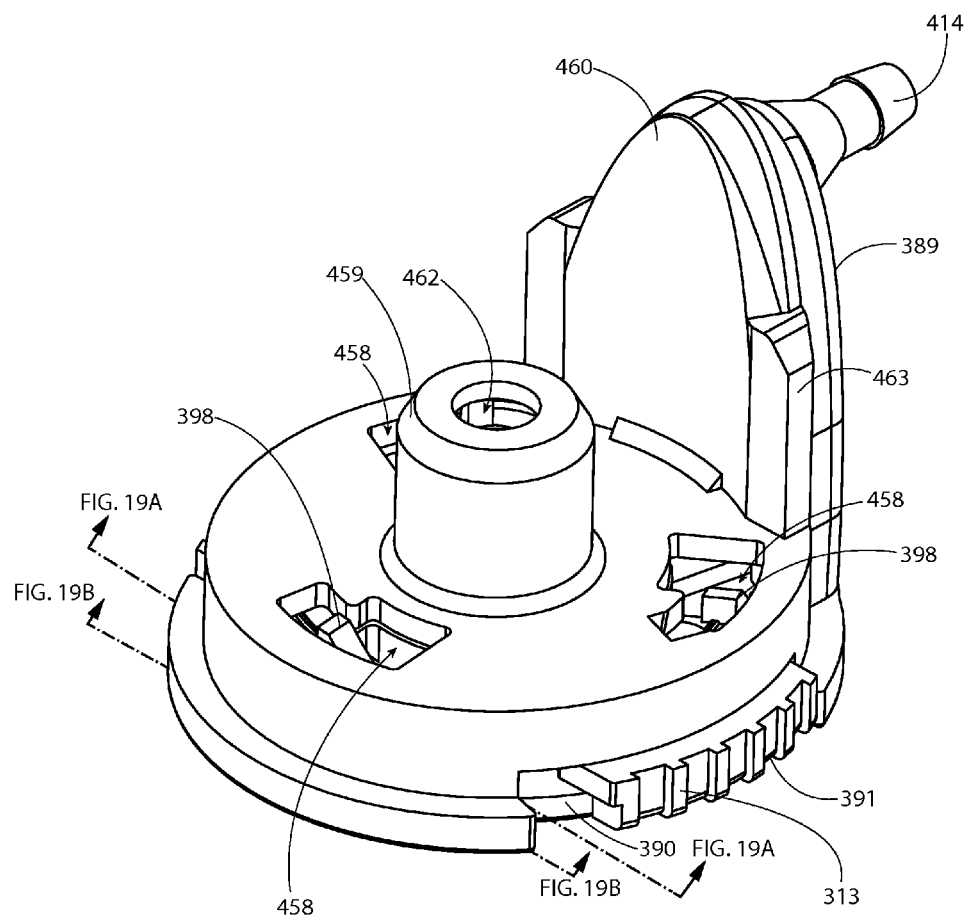
FIG. 18 is an isometric view of the removable base.
Figure 20A:
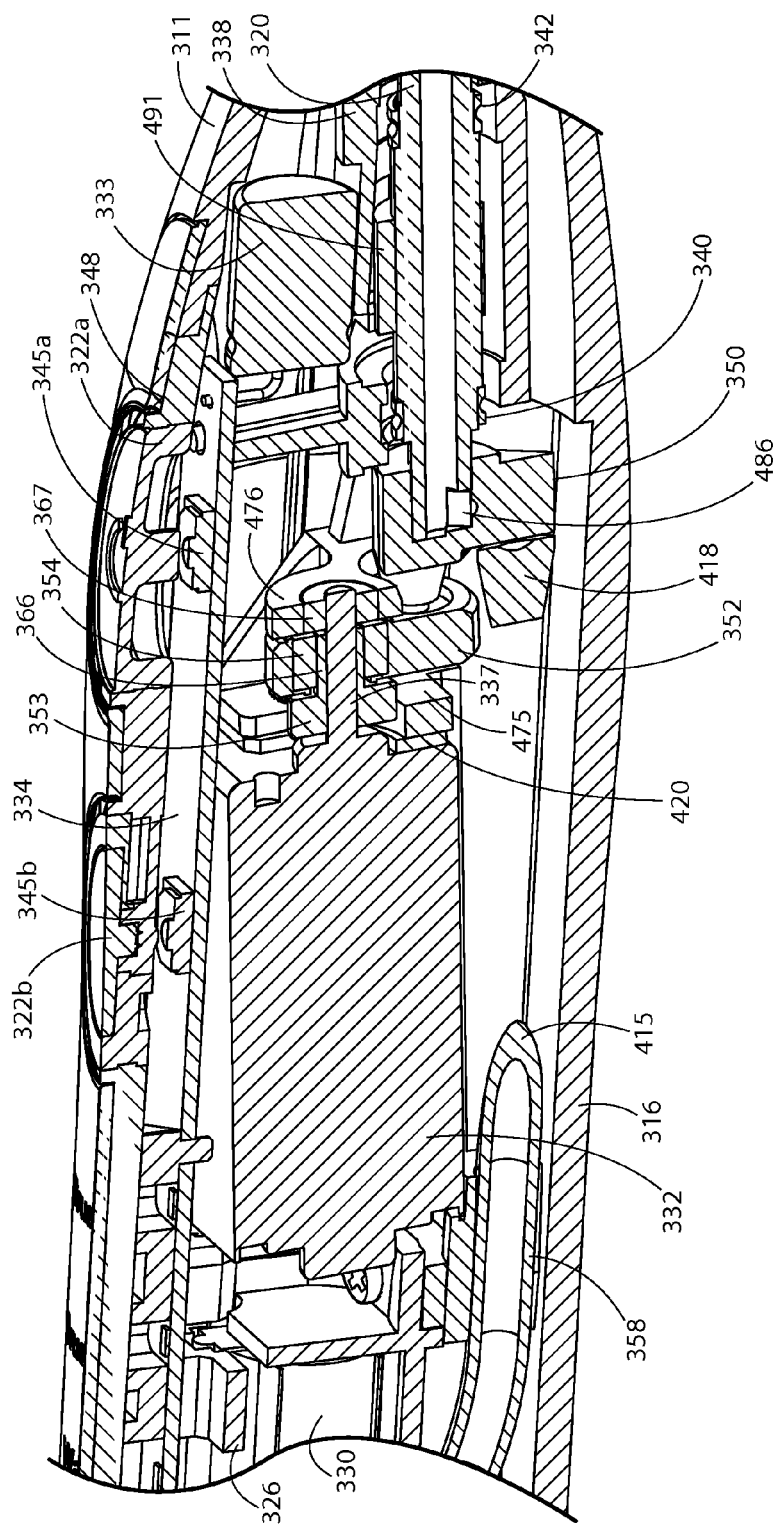
FIG. 20A is an enlarged, right side, isometric view in cross section of the toothbrush/flosser of FIG. 12A taken along line 14-14 in FIG. 12A detailing the middle portion of the handle including the motor and the drive train.
Figure 20B:
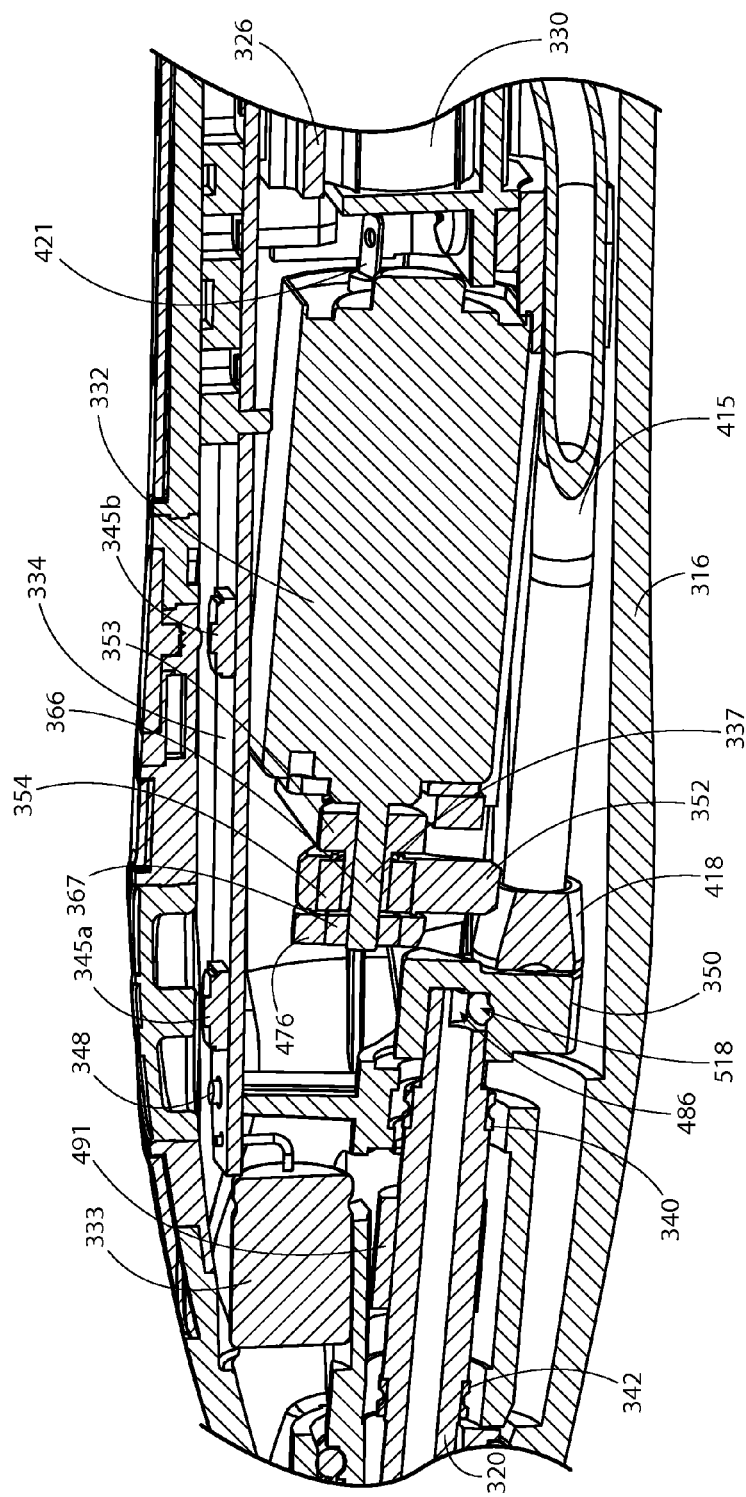
FIG. 20B is an enlarged, left side, isometric view in cross section of the toothbrush/flosser of FIG. 12A taken along line 14-14 in FIG. 12A detailing the middle portion of the handle including the motor and the drive train.
Figure 21:
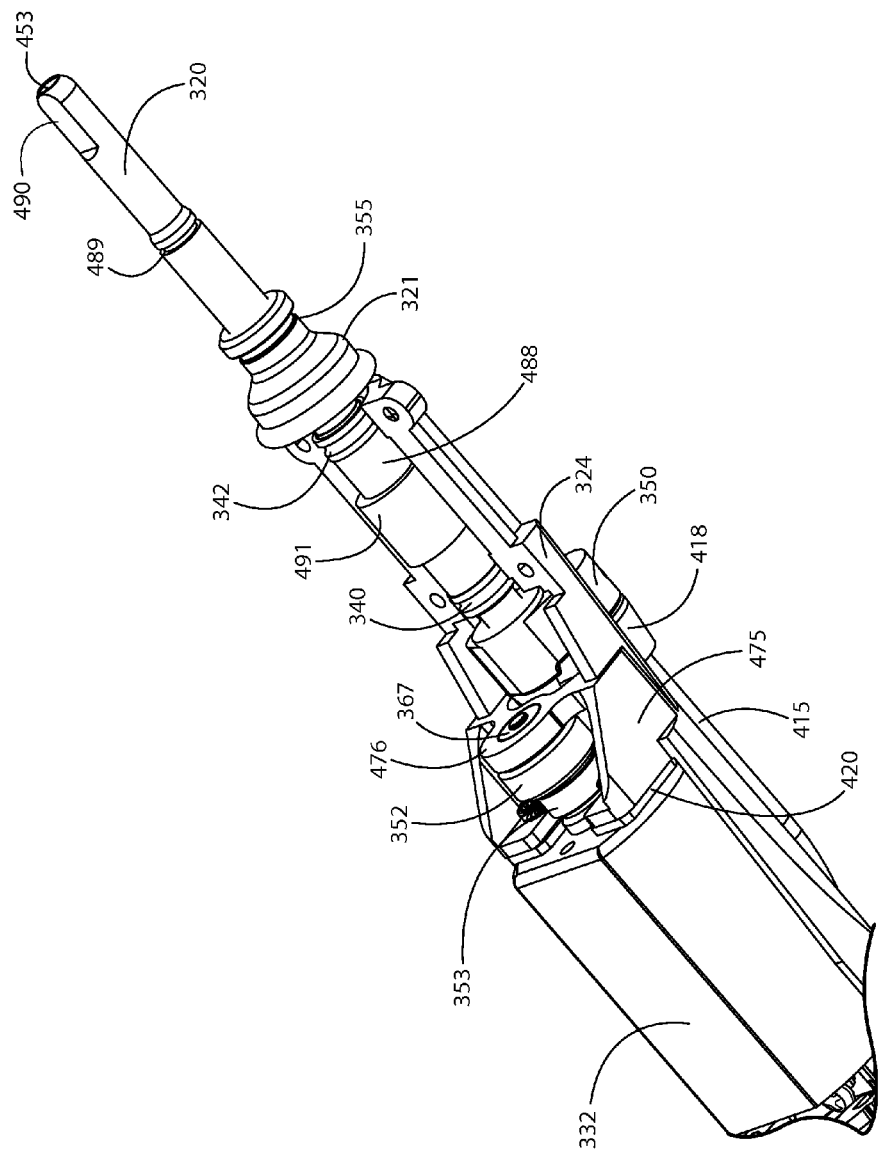
FIG. 21 is a front, right side isometric view of the drive train of the toothbrush/flosser of FIG. 12A with the housing and portions of the chassis removed.
Figure 22:
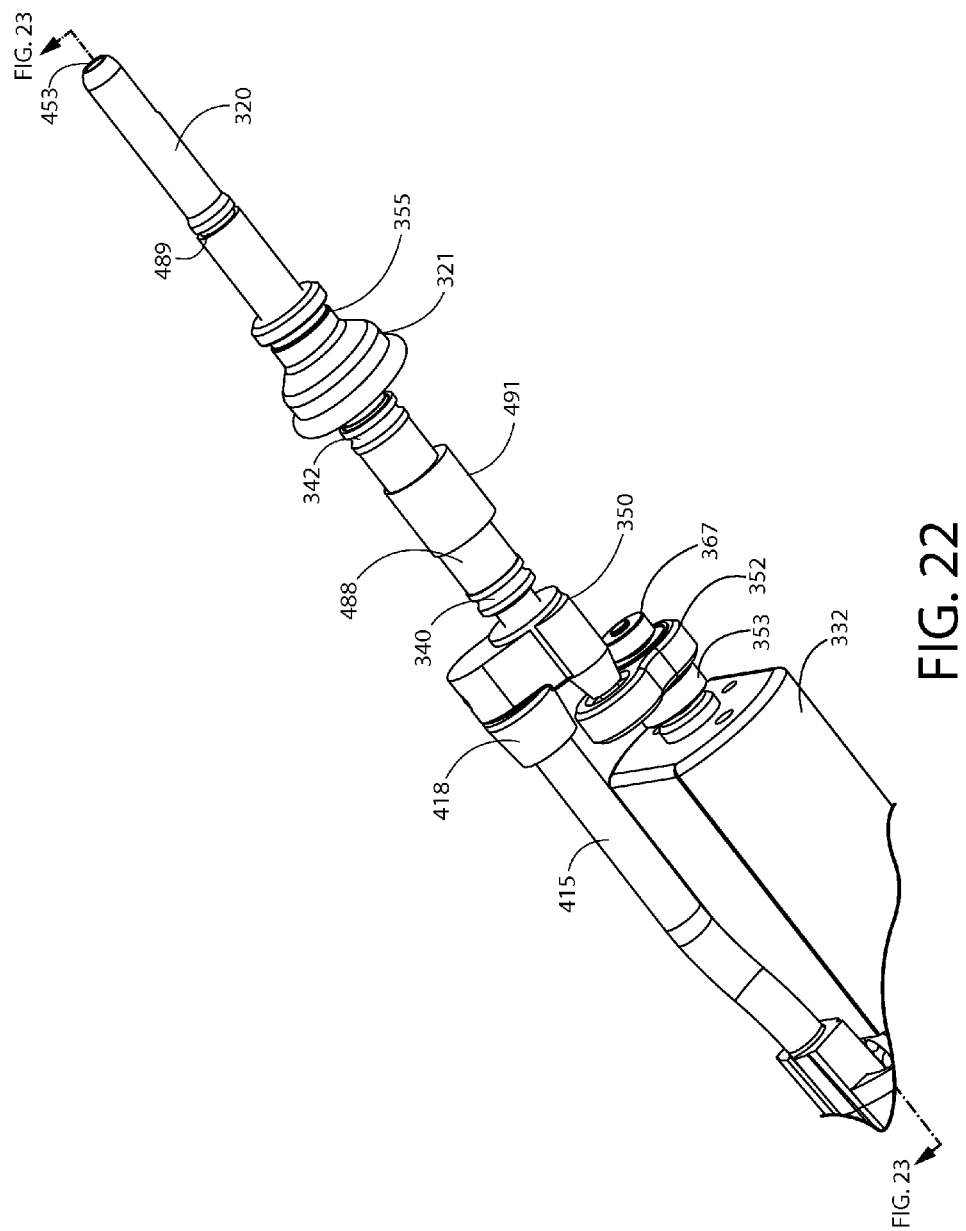
FIG. 22 is a rear, left side isometric view of the drive train of the toothbrush/flosser of FIG. 12A with the housing and the chassis removed.
Figure 23:
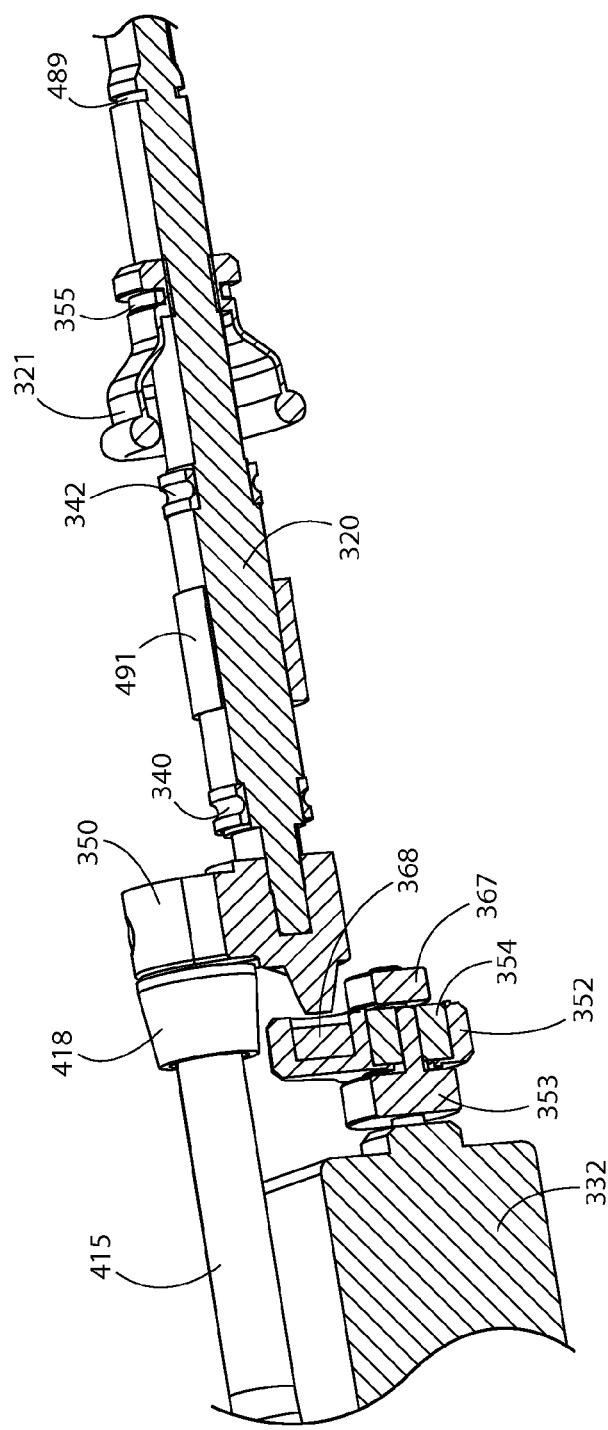
FIG. 23 is a left side, isometric view in cross section of the drive train of the toothbrush/flosser taken along line 23-23 in FIG. 22.
Figure 24:
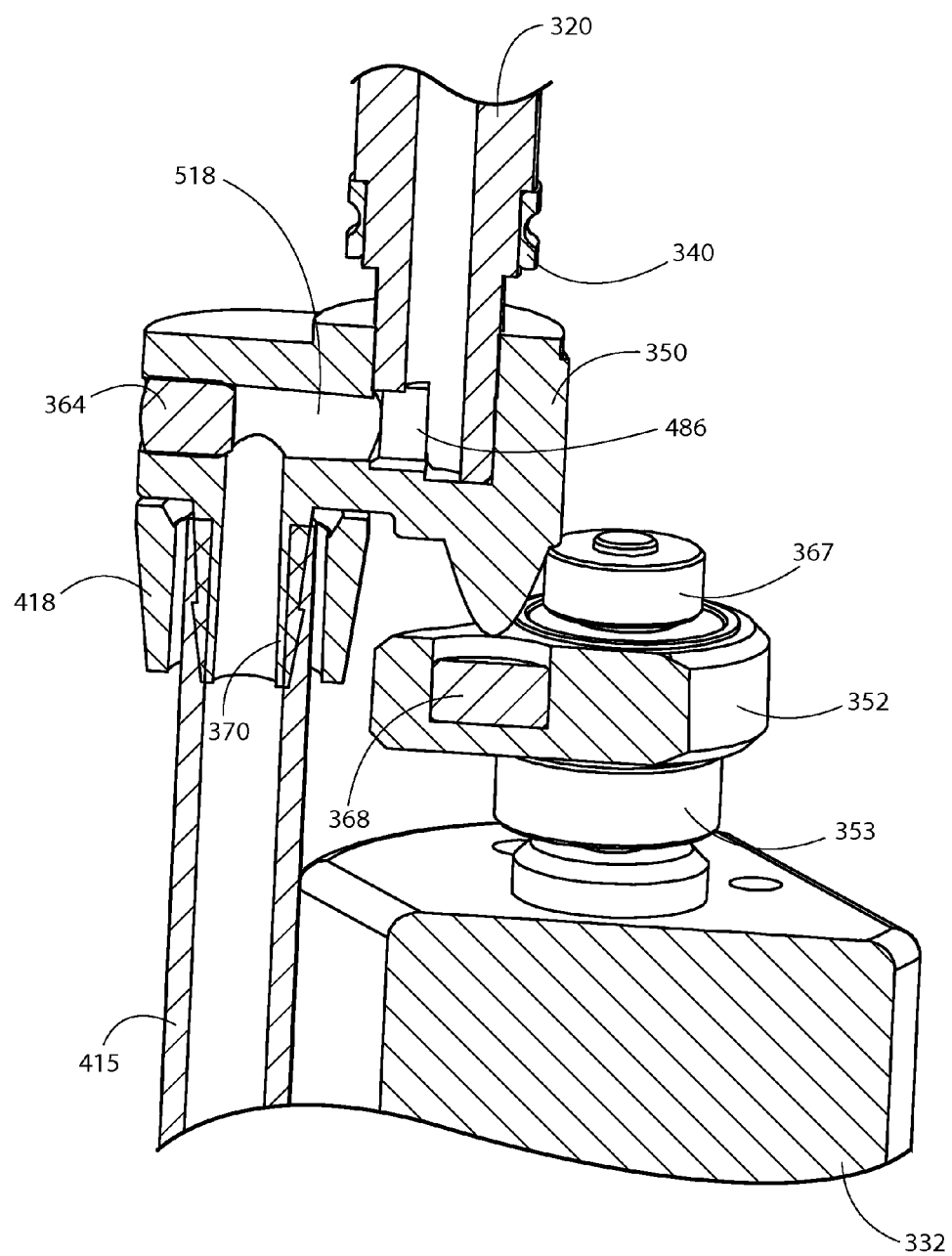
FIG. 24 is a rear, left side, isometric view in cross section of the drive train of the toothbrush/flosser taken along line 24-24 in FIG. 22.

The distal or front end of the irrigator socket 206 is formed as a barbed outlet 207 that connects with an internal transport hose 202 that carries water or other fluid from the irrigator socket 206 to the rocker arm 148. Another locking sleeve 204 may be placed over the transport hose 202 around the barbed outlet 207 to ensure a mechanically secure and fluid-tight seal. The transport hose 202 travels within the housing 116 and, in the present exemplary embodiment, through an aperture in the chassis 124 (as shown in FIGS. 17 and 18), and ultimately connects with an inlet barb 147 formed on the rocker arm 148 extending rearward parallel to the pivot shaft 167 as shown in FIGS. 5 and 6. A further locking sleeve 218 may be placed over the transport hose 202 around the barbed inlet 147 to ensure a mechanically secure and fluid-tight seal.

In this implementation, the rocker arm 148 further defines a fluid passage 250 that conducts fluid from the transport hose 202 to the channel 220 in the brush shaft 120. The fluid passage 250 extends from the inlet barb 147, which is oriented parallel with respect to the longitudinal axis of the toothbrush/flosser device 110, and bends laterally across the rocker arm 148 to intersect with the shaft cavity 172. The brush shaft 120 that is mounted within the shaft cavity 172 of the rocker arm 148 has a shaft inlet 252 formed as a cutout in the sidewall of the brush shaft 120 at the proximal or rear end that is aligned with the lateral branch of the fluid passage 250 within the rocker arm 148, thereby allowing fluid to flow from fluid passage 250 in the rocker arm 148 into the channel 220 in the brush shaft 120.

The front end of the brush shaft 120 is configured to engage with a brush tip 125 as shown in FIGS. 1 and 4. An exemplary brush tip 125 is shown in greater detail in FIGS. 9-11. The brush tip 125 may define a fluid flow channel 221 from the proximal or bottom end to the brush head 224. A shaft alignment insert 222 may be placed within the fluid flow channel 221 at the proximal end to align upon and engage with the distal tip of the brush shaft 120. As show in FIGS. 2-4, the brush shaft 120 may define an alignment step 240 at its distal tip wherein a portion of the sidewall of the brush shaft 120 is removed. The shaft alignment insert 222 may have a corresponding alignment shoulder 242 formed upon an inner wall for engagement with the alignment step 240. Thus, in order for the brush tip 125 to be placed fully upon and mechanically engaged with the brush shaft 120, the alignment step 240 and the alignment shoulder 242 must be oriented properly with respect to each other to fully interface.

In one exemplary embodiment, a portion of the sidewall of the alignment insert 222 may be windowed to define a longitudinal web 244 that is formed with a bump 246 that is aligned radially inward. The web 244 thus has some flexibility and can expand as needed to provide clearance to the brush shaft 120 while trying to appropriately orient the brush tip 125 thereon. Once the brush tip 125 and brush shaft 120 are properly oriented, the bump 246 may provide an additional mechanical retention force on the side of the brush shaft 120.

The brush tip 125 is further retained on the brush shaft 120 with a shaft clip 234 that has a detent 236 that interfaces with a detent receiver recess 238 formed along the sidewall of the brush shaft 120. In this exemplary embodiment, the shaft clip 234 is formed as part of a seal retainer 230 that retains a U-cup seal 323 within the brush tip 125 against the alignment insert 222. The U-cup seal 232 forms a fluid tight seal between the brush shaft 120 and the brush tip 125. The shaft retainer 230 may be formed extending from a living hinge molded as part of the sidewall of the seal retainer 230. The shaft clip 234 is biased radially inward in order to engage the detent 236 with the detent receiver 238 in the brush shaft 120. A release arm 235 of the shaft clip 234 make extend through an opening 237 in the sidewall of the brush tip 125 to allow a user to place reverse bias pressure on the shaft clip 234 and release the detent 236 from the detent receiver 238 in the brush shaft 120 to allow for removal of the brush tip 125.

When the brush tip 125 is installed on the brush shaft 120 and a water flosser function is selected by the user by pressing one or more of the control buttons 122a, 122b in an appropriate control sequence, or by turning on the water flosser base unit, water from the base unit is pumped through the external connector 212, through the transport hose 202 within the handle 111, through the rocker arm 148, through the brush shaft 120, through the fluid channel 221 in the brush tip 125, into the brush head 224, and out through the nozzle tip 228 mounted amongst the bristles 127 in the bristle base insert 226. It may be noted that the mechanically driven, sonic toothbrush and water flosser device 110 could also make use of a separate, unique flosser tip in addition to, or instead of, the brush head 224 with integral nozzle tip 228.

Figure 12A:
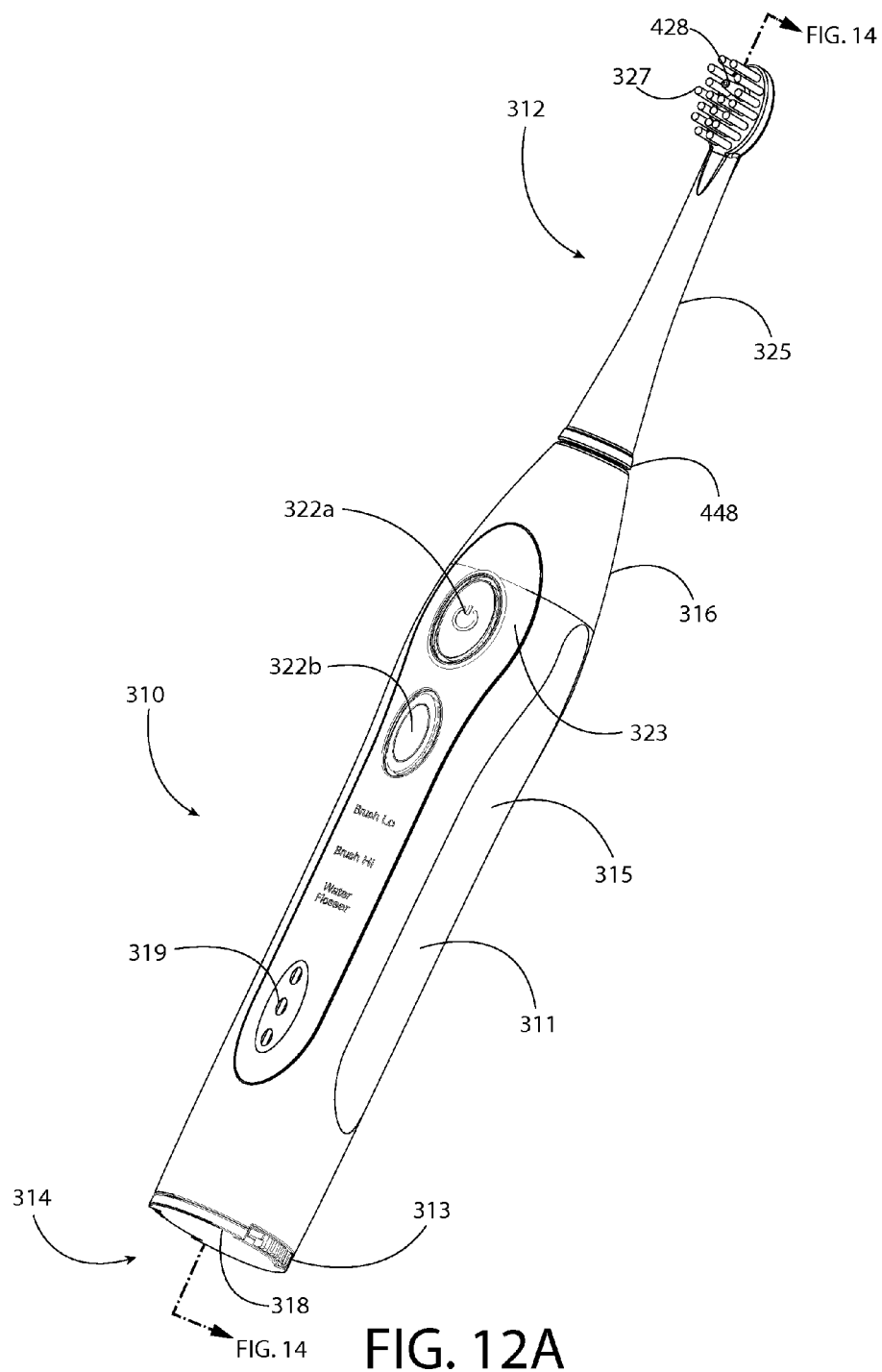
FIG. 12A is a front isometric view of an exemplary implementation of a combination mechanically-driven, sonic toothbrush and water flosser.
Figure 12B:
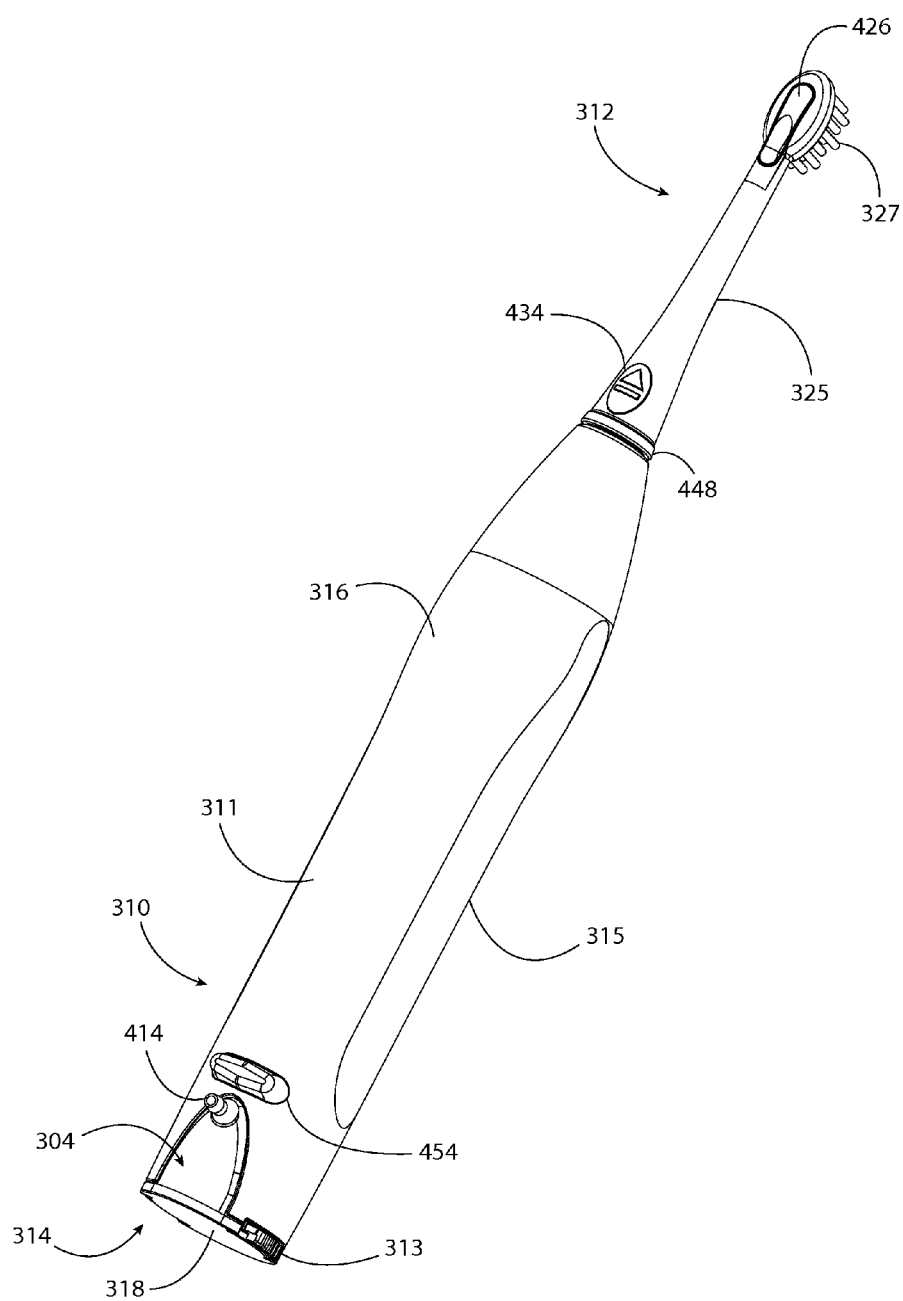
FIG. 12B is a rear isometric view of the toothbrush/flosser of FIG. 12A.
Figure 12C:
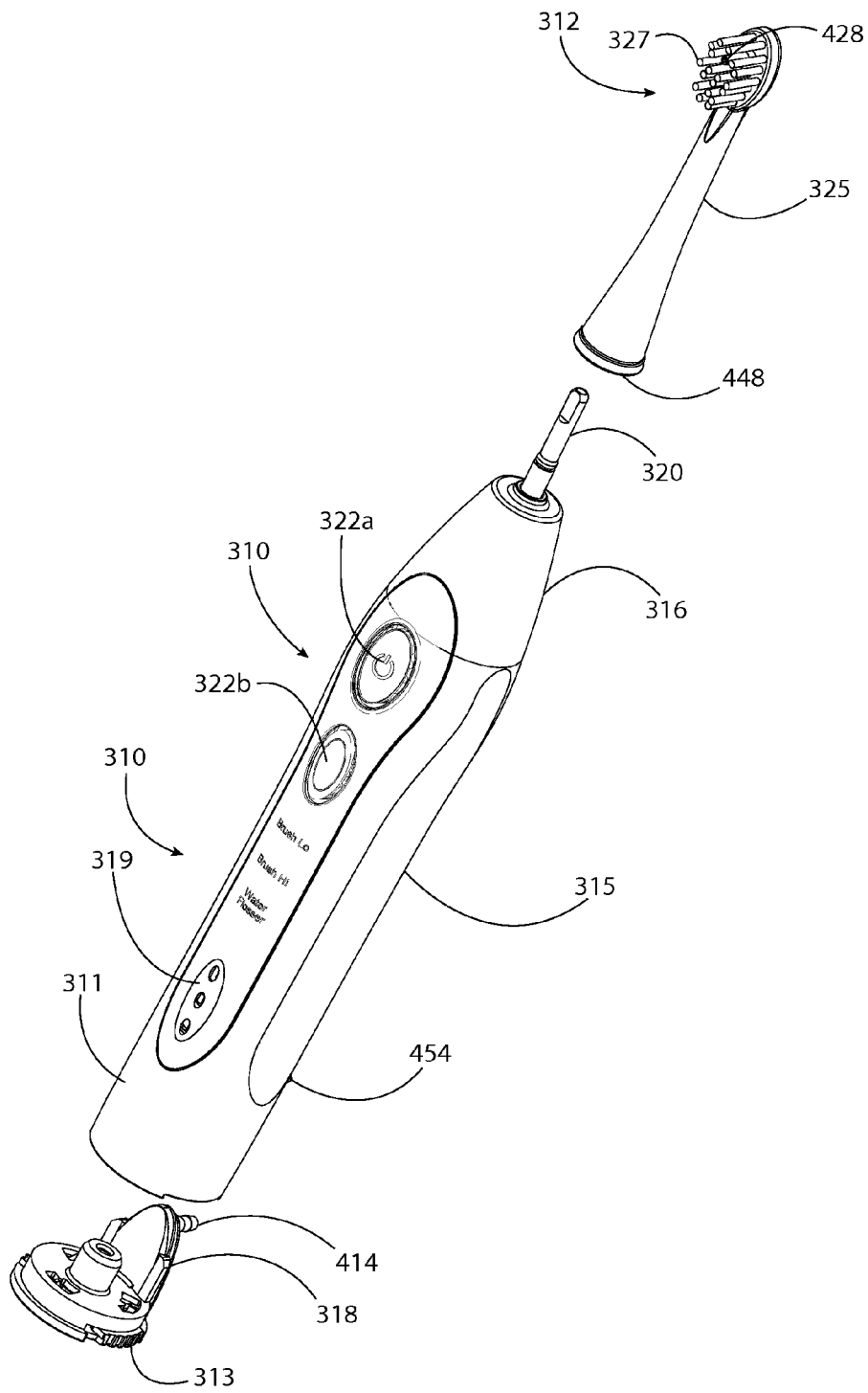
FIG. 12C is an exploded isometric view of the toothbrush/flosser of depicting the detachability of the brush tip and the base.

Another exemplary implementation of a combination mechanically driven, sonic toothbrush and water flosser 310 is presented in FIGS. 12A-32. As shown in FIGS. 12A-12C, the combination sonic toothbrush and flosser 310 is composed of a handle 311 and a removable brush tip 325. For purposes of reference, the distal end of the toothbrush/flosser 310 may be referred to as the brush end 312 and the proximal end may be referred to as a base end 314.

The handle 311 may be defined by a housing 316 that generally extends between the base end 314 and the brush end 312. The housing 316 may be generally cylindrical in shape to ergonomically fit in the hand of a user, but it may be formed in any other desirable ergonomic shapes. The cylindrical shape may begin to taper ballistically in the direction of the brush end 312 approximately one third the length of the housing 316 from the brush end 312. Elastomeric grip panels 315 may be overmoulded into oblong recesses 375 along the lateral sides of the housing 316 in order to provide a user with a comfortable grip that is less slippery when in use in a potentially wet environment.

The housing 316 may expose one or more actuation button covers 322a/b covering switches used to activate and control the functionality of the toothbrush/flosser 310. A face plate 323 may be supported on the housing 316 in a region extending about the control button covers 322a/b as either a separate plate or as an overmolded surface on the housing 316. The face plate 323 may further expose through one or more light apertures 319 or transparent areas one or more status indicators, e.g., LEDs, for indicating to a user a mode or status of operation of the toothbrush/flosser 310. Exemplary modes may be off, low speed, high speed, or water flosser mode, or some combination thereof. Exemplary status indications may be low battery, charging, and fully charged battery.

A removable base 318 may be attached to the base end 314 of the housing 316. A pair of release levers 313 may extend from lateral slots in the removable base 318 that may be operated by a user to release the removable base 318 from the housing 316. A fluid inlet 414 may extend from a portion of the removable base 318 for connection with a hose (not shown) that is connected to a water flosser base unit (not shown). An anti-roll bumper 454 may extend from a sidewall of the housing 316 to aid in preventing the toothbrush/flosser 310 from rolling off a counter or other surface if the toothbrush/flosser 310 is laid on its side.

The brush tip 325 may extend distally to form a brush head 424 from which a plurality of bristle tufts 327 may extend. In addition to the bristle tufts, a water jet nozzle 428 may extend from the brush head 424. A cover panel 426 may be provided on the rear of the brush tip 325 opposite the bristles 327 in order to aid in the assembly of the flosser nozzle 428. A release button 434 may be provided at a base of the brush tip 325 in order to release the brush tip 325 from the brush shaft 320 extending from the handle 311 as further described herein below. The brush tip 325 may further be provided with a color coded ring 448 at the base of the brush tip 325 or with some other coding scheme in any location on the brush tip 325 to allow multiple users to use the toothbrush/flosser 310 by easily identifying a personal brush tip that can be placed on the handle 311 after removing the brush tip of another user.

As shown in FIG. 12C and mentioned above, both the brush tip 325 and the base 318 of the toothbrush/flosser 310 may be removed from the handle 311. In addition to providing for multiple users, it is also desirable that the brush tip 325 be removable because the bristles 327 wear out after several months of use and it is therefore desirable for a user to purchase replacement brush tips 325 with new bristles 327 on a regular basis. The base 318 is removable to allow the handle 311 to be placed on an inductive charging unit (not shown) as further described below.

Figure 14:
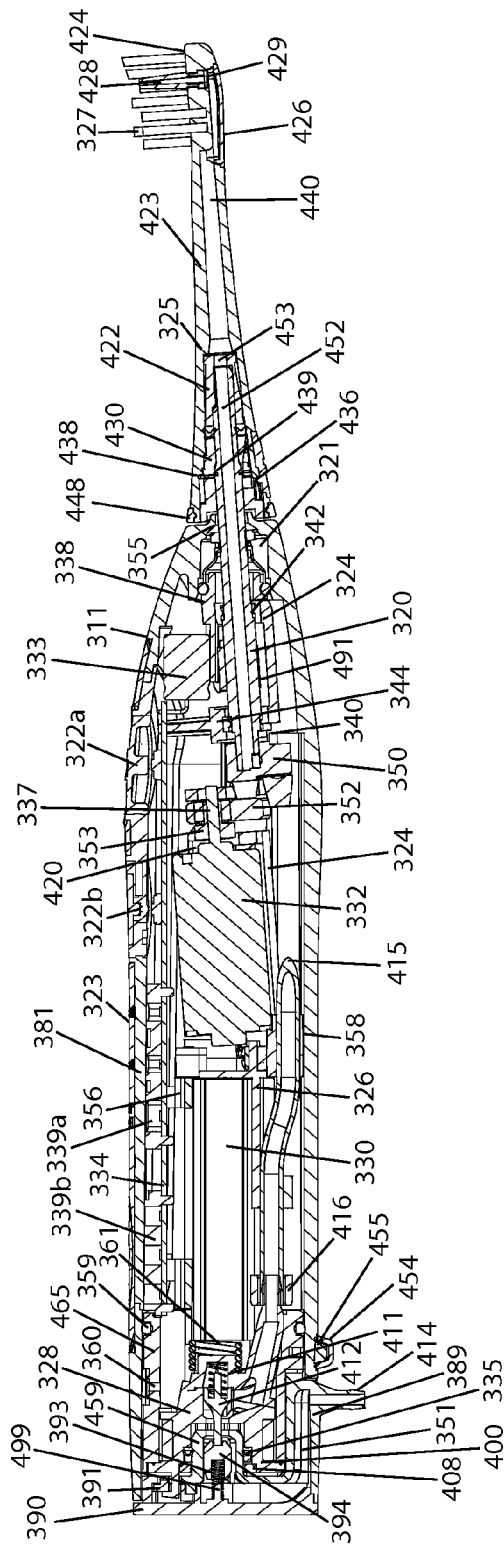
FIG. 14 is a right side elevation view in cross section of the toothbrush/flosser of FIG. 12A taken along line 14-14 in FIG. 12A.
Figure 15A:
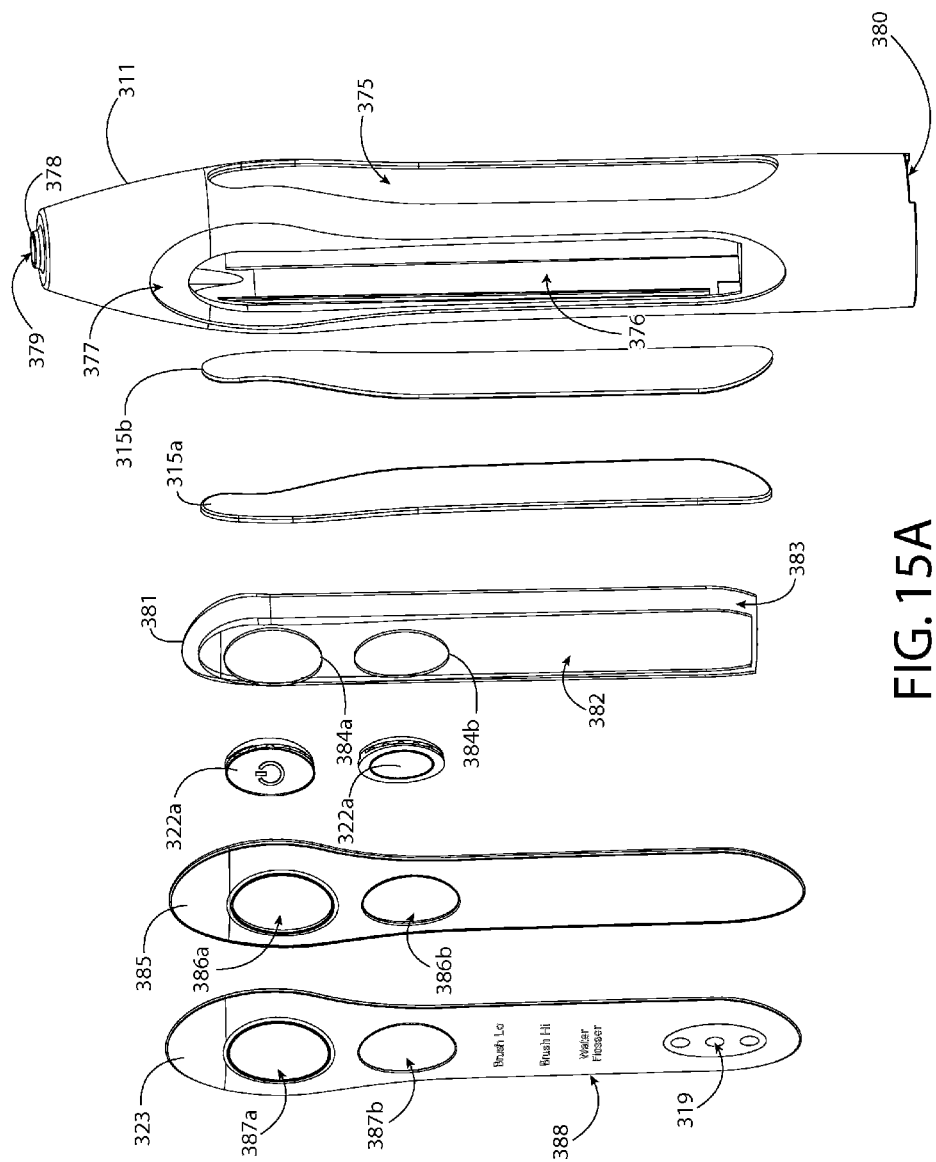
FIG. 15A is an exploded isometric view of the component parts of the toothbrush/flosser of FIG. 12A.

As shown in FIGS. 14 and 15A, the handle 311 may be composed of several different elements. The housing 316 as previously described is generally bullet-shaped. Two laterally opposed recesses 375 in the sidewall of the housing 316 on the lateral sides of the face plate 323 receive the overmould grips 315a/b. In some implementations, the grips 315a/b may be molded separately and adhered to the housing 316 with an adhesive. The housing 316 is a hollow shell that houses the functional components of the toothbrush/flosser system 310. A large, generally circular, bottom opening 380 is provided at the base end 314 of the housing 316 and a small circular opening is provided at the brush end 312 of the housing 316. A raised ring 378 may be formed on a top surface of the housing 316 to help provide alignment for engagement with the removable brush tip 325. An arched cutout 304 may be formed within the housing 316 on the back side at the base end 314 spaced laterally between the grips 315. (See FIGS. 1B and 17) in order to accommodate features of the removable base 318 as further described below. A pair of adjacent clip apertures (not visible) may also be formed in the back side of the housing 316 above the arched cutout 304. The housing 316 further defines a control system window 376 within a front surface of the housing 316. The control system window 376 may be oblong in shape and extend along a majority of the length of the housing 316 (about the same length as the grips 315a/b in the embodiment shown). A window cover recess 377 may be formed in the wall of the housing 316 around the control system window 376 as a depression in the surface of the housing 316 similar to the grip recesses 375.

A hermetic cover 381 may be placed within the control system window 376 from the inside of the housing 316 such that a raised window panel 382 conforming in size and shape to the control system window 376 fits through the control system window 376. The raised window panel 382 may extend from an edge flange 383 of the hermetic cover 381 at a thickness congruent to a thickness of the housing 316 through the area of the window cover recess 377. Thus, a top surface of the raised window panel 382 is flush with the window cover recess 377. The edge flange 383 extends beyond the perimeter of the control system window 377 to interface with an interior surface of the housing 316 surrounding the control system window 376. The edge flange 383 may be ultrasonically welded or otherwise adhered to the inner surface of the housing 316 to create a fluid tight seal between the hermetic cover 381 and the housing 316.

In this exemplary embodiment, the hermetic cover 381 may be made of a transparent plastic material in order to allow for transmission of LED light to the light apertures 319 in the face plate 323 noted above. The hermetic cover 381 may further define button apertures 384a/b within the window panel 382. The control button covers 322a/b fit within and seal against the sidewalls defining the apertures 384a/b. The control button covers 322a/b may be moulded or otherwise formed of an elastomeric material. The control button covers 322a/b may be overmoulded or adhered to the hermetic cover 381 in order to create a fluid tight seal.

A housing plate 385 of the same size and shape as the window cover recess 377 and having a thickness slightly less than congruent to a depth of the window cover recess 337 may be placed on top of the hermetic cover 381 and ultrasonically welded, adhered, or otherwise attached to the window cover recess 377 and the window panel 382 of the hermetic cover 381. The housing plate 385 thereby provides additional protection from fluids to the components inside the housing 316. Additional button cover apertures 386a/b may be formed in the housing plate 385 through which the control button covers 322a/b extend for access by a user. The housing plate 385 may be made of a transparent plastic material in order to allow for transmission of LED light to the light apertures 319 in the face plate 323 noted above.

The face plate 323 introduced above may be placed over the housing plate 385 and adhered, ultrasonically welded, or otherwise fastened thereto. The face plate 323 may define button cover apertures 387a/b through which the control button covers 322a/b extend for access by a user. The face plate 323 may be formed of a transparent plastic material, however, a surface of the face plate 323 may be coated with an opaque color or tint while areas of the coating may be removed or etched in relief in order to allow transmission of light through certain areas of the face plate 323. In another implementation, the material forming the face plate 323 may be formed with a pigment that is activated (or deactivated) in response to a stimulus and areas of the face plate may be fixed in a transparent state while other areas are fixed as opaque. For example, as shown in FIG. 15A, mode indicators 388 for the states of high speed brushing, low speed brushing, and water flosser, either independently or the latter in conjunction with one or the other of the two prior, may be provided in etched or screened openings in the face plate 323. Additionally, as shown, the light apertures 319 could be formed as transparent areas in the opaque coating or material. Alternatively, the light apertures 319 could be formed as actual apertures in the face plate 323.

Figure 13A:
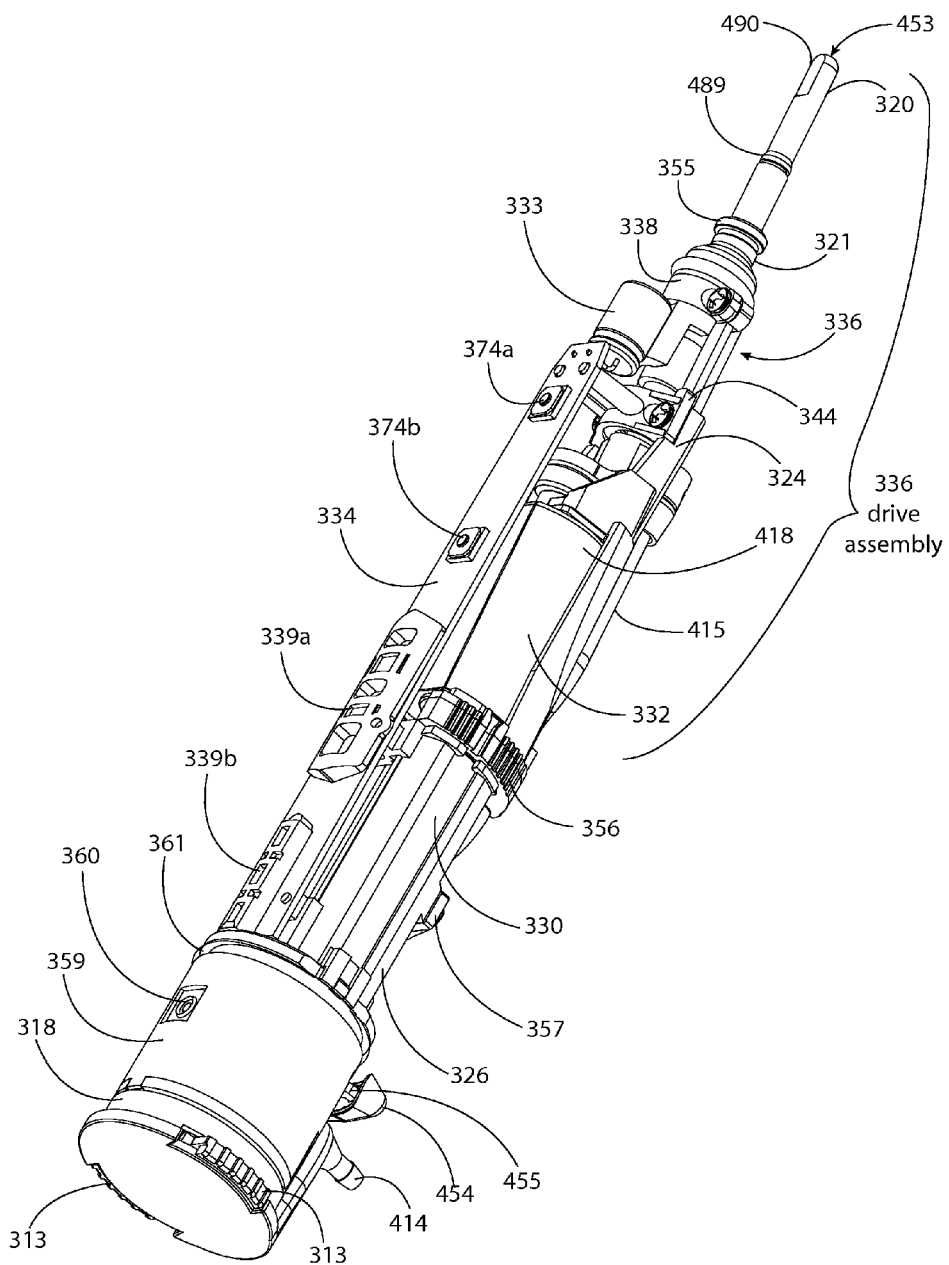
FIG. 13A is a front, right side, isometric view of the toothbrush/flosser of FIG. 12A with the housing and brush tip removed.
Figure 13B:
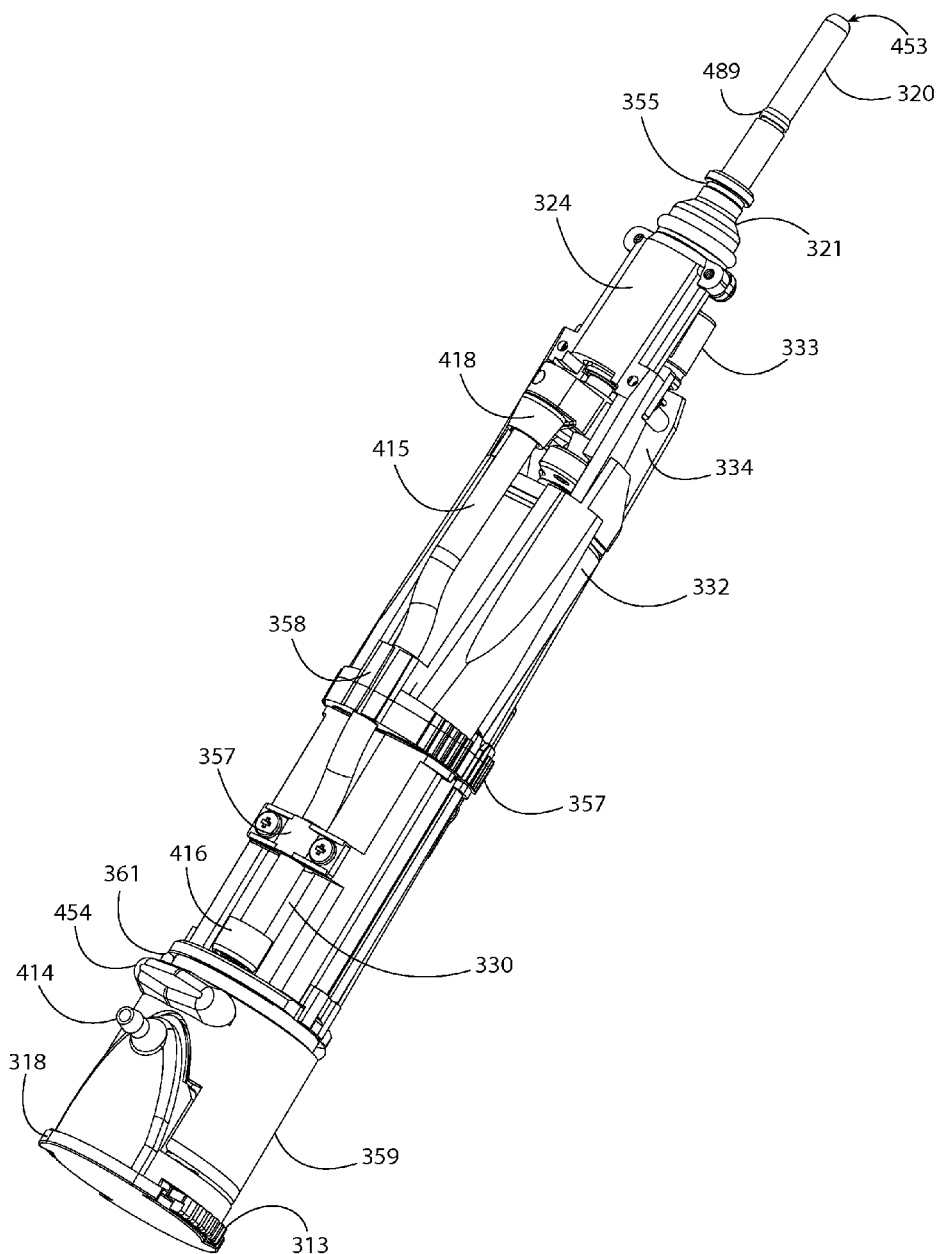
FIG. 13B is a rear, left side, isometric view of the toothbrush/flosser of FIG. 12A with the housing and brush tip removed.
Figure 15B:
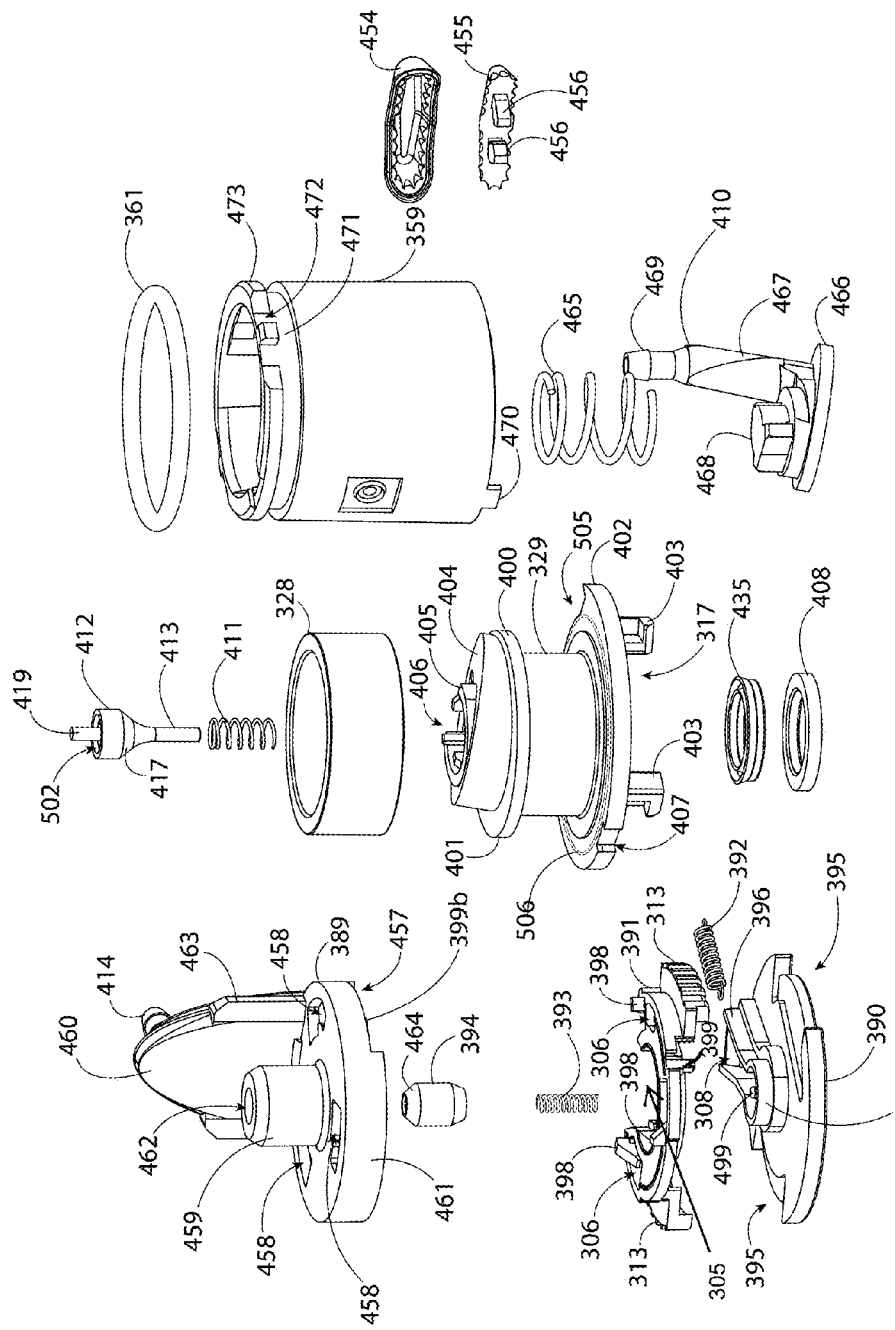
FIG. 15B is an exploded isometric view of the component parts of the toothbrush/flosser of FIG. 12A.

The internal components of the toothbrush/flosser 310 are shown assembled with the housing 316 removed in FIGS. 13A and 13B, assembled in cross section in FIG. 14, and separately in the exploded views of FIGS. 15A-15C. Beginning at the base end 314, the removable base 318 is formed of several components. A generally circular base plate 390 and a base cap 389 are joined together sandwiching a latch plate 391 therebetween to form the removable base 318. These components may also be seen in the enlarged views of FIGS. 16-19B detailing the removable base 318 in a connected configuration and in a disconnected configuration, respectively.

The bottom surface of the base plate 390 may be flat as shown in order to stand the toothbrush/flosser 310 upright on a flat surface when not in use. A sidewall of the base plate may define a pair of arcuate lever recesses 395 laterally disposed from each other to provide clearance for access to and movement of the base release levers 313 on the latch plate 391. A fluid channel 396 may be formed on a top surface of the base plate 390. In the embodiment shown, a stepped wall 309 in the shape of a keyway positioned between the lever recesses 395 and having an open end 308 directed radially outward from the center of the base plate 390 may define the fluid channel 396. A closed end 307 opposite the open end may be generally circular in shape and extend around a center of the base plate 390. A spring alignment post 499 may extend normally from the top surface of the base plate 390 within the center of the circular section (closed end 307) of the stepped wall 309 defining the fluid channel 396.

The latch plate 391 may be positioned on top of the base plate 390. The latch plate 391 may be generally circular in form with a wedge- or arc-section-shaped channel cutout 397 positioned between the release levers 313 about the circumference of the latch plate 391. The channel cutout 397 extends as a circular area from the wedge-shaped portion in the center of the latch plate 391. The channel cutout 397 may thus be formed to fit around the stepped walls 309 forming the fluid channel 396 in the base plate 390. As noted, the base release levers 313 may extend from lateral sides of the latch plate 391 and reside within the lever recesses 395 in the base plate 390. The area defined by the channel cutout 397 may be slightly larger than the width of the fluid channel. Similarly, the arc length of the lever recesses 395 may be slightly longer than the length of the release levers 313. This difference in size of the components allows the latch plate 391 to rotate or pivot back and forth a short and constrained travel distance with respect to the base plate 390.

A number of latch apertures 306 (in this exemplary implementation there are three) may be formed in the body of the latch plate 391. A number of latch fingers 398 (in this exemplary implementation there are three) extend with the latch apertures 306 and a portion of each of the latch fingers 398 also extends above a top surface of the latch plate 391 spaced around the center portion of the channel cutout 397. A spring post 399 may extend normally from a bottom surface of the latch plate 391 adjacent to one of the release levers 313. A post aperture 305 may also be formed in the body of the latch plate 391 between two of the latch apertures 306. The post aperture 305 may be formed in an oblong, arcuate shape.

The base cap 389 may be formed with a bottom sidewall 461 that defines a generally circular cavity on the bottom side of the base cap 389. A pair of laterally positioned lever cutouts 457 may be formed in the sidewall 461 to provide clearance for access to and movement of the base release levers 313 on the latch plate 391. The arc length of the lever cutouts 457 may be slightly longer than the length of the release levers 313. This difference in size of the components allows the latch plate 391 to rotate or pivot back and forth a short and constrained travel distance with respect to the base cap 389. A number of boot-shaped latch slots 458 (in this exemplary implementation there are three) may be formed in the top surface of the base cap 389. A spring post 499 may extend from a bottom surface of the base cap 389 and be positioned to extend through the post aperture 305 in the latch plate 391. A mating wall 302 in a symmetrical form to the stepped wall 309 forming the fluid channel 396 in the base plate 390 may extend from the bottom surface of the base cap 389. (See FIGS. 19A and 19B.) The mating wall 302 is configured to fit around the upper, inner step of the stepped wall 309 and mate face to face with the lower, outer step of the stepped wall 309 to cap the fluid channel 396.

A valve post 459 may be formed as a cylindrical extension centered on and normal to the top surface of the base cap 389. The valve post 459 defines a cavity that is open through the bottom of the base cap 389. Several ribs 301 may be formed along the inner walls of the cavity within the valve post 459. A post aperture 462 is also formed in the top of the valve post 459 to provide a fluid outlet from the cavity defined by the valve post 459. A fluid channel casing 460 may extend normally from the top of the base cap 389 along a circumferential edge thereof positioned laterally on the circumferential edge between the lever cutouts 457. In this exemplary implementation, the fluid channel casing 460 is in the form of an arch with a curved inner wall following the outer circumference of the base cap 389 at a shorter radius than the outer circumference. An outer wall of the fluid channel casing 460 is also curved to match the circumference of the base plate 390 which it abuts when the removable base 318 is fully assembled. A pair of guide flanges 463 may further extend laterally from the sides of the fluid channel casing 460. The inlet port 414 extends from the outer wall of the fluid channel casing 460. The inlet port 414 may have a barbed tip in order to create a secure, fluid-tight seal with a fluid hose from a base pump and reservoir unit (not shown). The fluid channel casing 460 defines a fluid channel 351 therein that provides fluid communication between the inlet port 414 and the fluid channel 396.

A barrel shaped lower poppet 394 is housed within the cavity defined by the valve post 459 and is biased against the top wall of the valve post 459 by a lower poppet spring 393 when the removable base 318 is in a removed configuration. The ribs 301 on this inner wall of the valve post 459 center the lower poppet 394 within the cavity to allow for fluid flow around the lower poppet 394, between the lower poppet 394 and the inner wall of the valve post 459. The lower poppet spring 393 is retained around the spring post 499 extending from the base plate 390 within the center of the fluid channel 396. A top end of the lower poppet spring 393 seats within a cylindrical cavity 500 in the bottom of the lower poppet 394. A shallow recess 501 may further be formed within a top surface of the lower poppet 394. The top edge of the lower poppet 394 may be beveled to form a sealing surface 464 that seals against the top wall of the valve post 459 defining the post aperture 462. The lower poppet 394 may be made of a dense rubber or other elastomeric material (i.e., an elastomer material with a relatively high elastic modulus) in order to maintain its form while simultaneously providing a fluid-tight seal against the valve post 459. Alternatively, the lower poppet 394 could be made of a plastic and coated with an elastomer on at least the sealing surface 464 in order to provide a fluid-tight seal.

The base cap 389 may be aligned with and placed over the latch plate 391 such that the latch slots 458 generally align with the latch apertures 306 in the latch plate 391. Portions of the latch fingers 398 of the latch plate 391 may extend through the latch slots 458 in the base cap 389. The spring post 499 extending from the bottom of the base cap 389 may extend through the post aperture 305 in the latch plate 391. A latch spring 392 may be attached between the latch plate 391 and the base plate 390 at a first end to the spring post 399a extending from the bottom of the latch plate 391 and at a second end to the spring post 499 extending from the bottom of the base cap 389. The base cap 389 may be ultrasonically welded or adhered to the base plate 390 to ensure a fluid tight seal between the mating wall 302 and the stepped wall 309 forming the fluid channel 396. The sidewall 461 and the spring post 499 of the base cap 389 may also be joined to the top surface of the base plate 390. As the diameter of the base plate 390 is slightly larger than the diameter of the sidewall 461, a lip or flange of the base plate 390 remains exposed over portions of the perimeter of the base plate 390. This exposed lip or flange mates against the bottom edge of the housing 316 when the removable base 318 is attached to the handle 311 to cap the bottom opening 380 in the housing 316. When the base plate 390 and base cap 389 are joined together, the latch plate 391 and lower poppet valve 394 and their corresponding springs 392, 393 are housed therein. The latch plate 391 is able to pivot between the base cap 389 and the base plate 390 and the lower poppet is able to move within the valve post 459 and the center of the fluid channel 396.

The removable base 318 mates with a coil bobbin 400 when it is attached to the handle 311. The coil bobbin 400 is a generally cylindrical structure that defines an outer winding surface 409 around which an induction charging coil 328 is wound. A retainer flange 401 extends radially outward to form a top boundary of the winding surface 409. A base flange 402 similarly extends radially outward to define a bottom boundary of the winding surface 409. The base flange 402 is larger in diameter than the retainer flange 401. An arcuate cutout 505 is formed in an edge of the base flange 402 on a back side of the coil bobbin 400 in order to accommodate the inner arcuate wall of the fluid channel casing 460 of the removable base 318. An alignment recess 407 is also formed in the edge of the base flange 402 on the front side opposite the arcuate cutout 505. A circumferential groove 506 (interrupted by the arcuate cutout 505) is formed in a top surface of the base flange 402. A number of latch feet 403 (in this exemplary implementation there are three) may extend normally from a bottom surface of the base flange 402 arranged and positioned to align with the latch slots 458 in the removable base 318.

The coil bobbin 400 further defines a stepped cavity on the base end 314 that receives the valve post 459 of the removable base 318 and also serves as an induction charging port 317 when the removable base 318 is removed. The charging port 317 receives a coil seal 335 (e.g., a cup seal) in a middle step between a smaller diameter of the charging port 317 that closely fits the valve post 459 and a larger diameter of the charging port 317 that receives an annular seal retainer 408 that holds the coil seal 335 in place. The seal retainer 408 may be press fit into the largest diameter shelf or step of the charging port 317 and sit flush with a base surface of the coil bobbin 400. The seal retainer 408 may further act as an energy director to aid in the inductive charging of the toothbrush/flosser 310.

A circular, angled mounting surface 404 may be formed as the top portion of the coil bobbin 400 above the retainer flange 401. The mounting surface 404 is offset from a front edge of the retainer flange 401 but extends to be almost congruent with a back edge of the retainer flange. The mounting surface 404 angles downward from the front edge to the back edge. A conduit wall 405 extends from the mounting surface 404 normally with respect to the retainer flange 401 and defines a fluid outlet 406 that is in fluid communication with the induction charging port 317 via a bobbin aperture 504 formed therebetween. A back section of the conduit wall 405 is notched and several ribs 503 are positioned vertically along the inner surface of the conduit wall 405.

A bobbin cap 410 seals against the mounting surface 404 of the coil bobbin 400. The bobbin cap 410 is formed with a flat seal plate 466 at its base that forms an opposing surface at a congruent angle with the mounting surface 404. A spring post 468 is formed above the seal plate 466 and defines a cavity therein that fits over the conduit wall 405 extending above the mounting surface 404. A tubular fluid connector 467 extends upward from a back side of the bobbin cap 410 and defines a fluid lumen 508 that is in fluid communication with the cavity under the spring post 468. When the bobbin cap 410 is joined to the mounting surface 404 of the coil bobbin 400 (e.g., by ultrasonic welding), a fluid-tight fluid passage is formed between the fluid outlet 406 in the conduit wall 405 and the fluid lumen 508. An outer surface at the end of the fluid connector 467 may be formed as a connector barb 469. A compression spring 465 seats around an outer surface of the spring post 468 on the bobbin cap 410.

An upper poppet 412 may also be positioned within the fluid outlet 406 defined by the conduit wall 405. The upper poppet 412 may have a downward extending plunger 413 that extends through the bobbin aperture 504 and an upward extending post 419 that receives an upper poppet spring 411. The upper poppet spring 411 may extend into the cavity defined by the spring post 468 in the bobbin cap 410. An annular recess may be defined in a top surface of the upper poppet 412 around the post 419 to further confine the upper poppet spring 411. A lower surface of the upper poppet 412 may be beveled to form a sealing surface 417 that creates a fluid-tight seal with the wall defining the bobbin aperture 504 when biased downward by the upper poppet spring 411 when the removable base 318 is removed from the handle 311. The upper poppet 412 may be made of a dense rubber or other elastomeric material (i.e., an elastomer material with a relatively high elastic modulus) in order to maintain its form while simultaneously providing a fluid-tight seal against the bobbin aperture 504. Alternatively, the upper poppet 412 could be made of a plastic and coated with an elastomer on at least the sealing surface 417 in order to provide a fluid-tight seal. The ribs 503 lining the inner surface of the conduit wall 405 center the upper poppet 412 within the cavity to allow for fluid flow around the upper poppet 412 to exit through the fluid outlet 406 in the coil bobbin.

A base cover 359 is a generally cylindrical structure that seats around the coil bobbin 400 and the bobbin cap 410. A vent hole 360 is formed in the front wall of the base cover 359 to vent any pressure that may build up if the certain components (e.g., batteries or the motor) malfunction (e.g., break down and release chemical fumes or overheat). The vent hole 360 may also act as a weep hole indicating a failure of a fluid seal within the handle 311. Any fluids (gases or liquids) escaping through the vent hole 360 will escape from the bottom end 314 of the housing 316. An annular recess adjacent a top edge of the base cover 359 functions as a seal retainer 471 and receives a base cap seal 361 (e.g., an O-ring) that seals the base cover 359 against an interior surface of the housing 316. A flange 473 immediately adjacent a top edge of the base cover 359 retains the base cap seal 361 in the seal retainer 471. Several clip recesses 472 may be formed in the flange 473 to aid in connecting the base cover 359 to other structures as further described below. Additionally, opposing shelves (not shown) may be formed on an inner wall of the base cover 359 generally at the same position longitudinally as the vent hole 360 on the lateral sidewalls with respect thereto to further aid in connecting the base cover 359 to other structures as further described below.

The bottom edge of the base cover 359 may seat against the base flange 402 of the coil bobbin 400. The bottom edge of the base cover 359 may define a small ridge 507 designed to mate with the groove 506 in the top surface of the base flange 402. The ridge 507 and groove 506 may provide for positional alignment between the base cover 359 and the base flange 400 and may further provide for a strong bond between the bottom edge of the base cover 359 and the base flange 402 when they are joined together (e.g., by ultrasonic welding). The alignment tab 470 extending from the bottom edge of the base cover 359 may also mate with the alignment recess 407 in the front edge of the base flange 402 to additionally align the base cover 359 on the coil bobbin 400. When the base cover 359 is attached to the coil bobbin 400, the connector barb 469 on the fluid connector 467 of the bobbin cap 410 extends above the top edge of the base cover 359.

The back side of the base cover 359 may further define an arched recess 479 sized and shaped to fit around the arch-shaped fluid channel casing 460 of the removable base 318. A horizontal channel 303 may also be formed in the back side of the base cover 359 above the arched recess 479. The horizontal channel 303 receives a pair clips 456 extending from an anti-roll bumper base 455 covered by the anti-roll bumper 454, which may be formed of an elastomeric material in order to provide a frictional grip against a surface. The anti-roll bumper 454 may be overmoulded on, adhered to, or press fit over the anti-roll base 455. The surface of the anti-roll base 455 may be knurled, fluted, or otherwise textured to provide a stronger bonding surface with the anti-roll bumper 454. Likewise, the anti-roll bumper 454, if formed separately, may be formed with an internal cavity that conforms to the surface shape of the anti-roll base 455. The clips 456 extend through the pair of clip apertures (not visible) in the housing 316 above the arched cutout 304 and may be press fit, adhered, or ultrasonically welded within the horizontal channel 303 in the base cover 359 to fasten the anti-roll bumper 454 to the handle 311.

Figure 16:
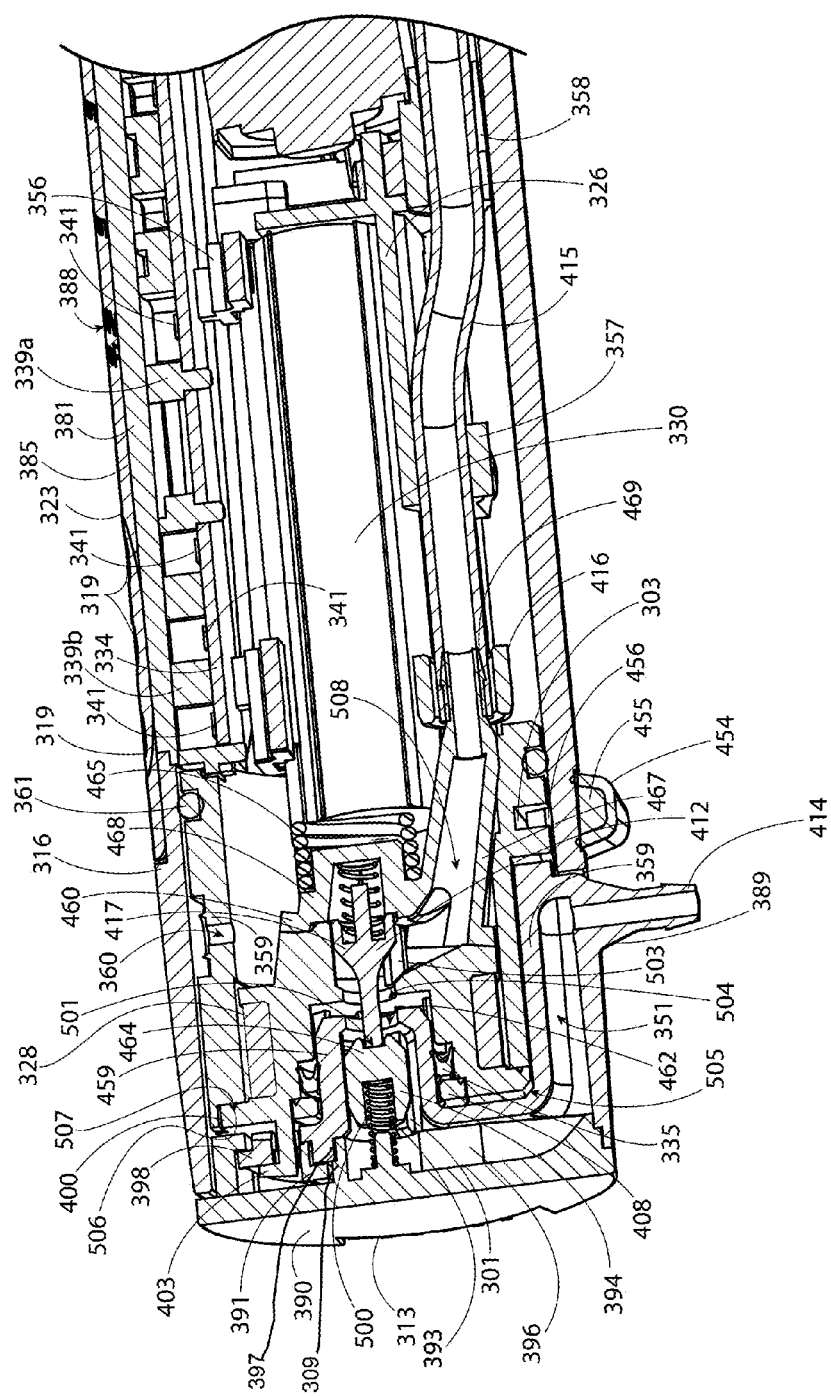
FIG. 16 is an enlarged, right side, isometric view in cross section of the toothbrush/flosser of FIG. 12A taken along line 14-14 in FIG. 12A detailing the bottom portion of the handle including the detachable base and the power supply.

As best depicted in FIGS. 14, 15C, and 16, a battery carrier 326 housing a battery pack 330 of rechargeable batteries may be mounted immediately above and connected to the base cover 359. The battery pack 330 may use 2 AA or 2AAA sized rechargeable batteries or any other size or configuration of batteries that may be appropriate to drive the toothbrush/flosser 310. The battery pack 330 may be contained within a framework of the battery carrier 326 forming a battery cage 373. A spacer cavity 349 is formed on the top of the battery carrier 326 above the battery pack 330 by a top plate 509 and a wall serving as a chassis mount 510. A number of mounting pins 348 may extend from a front side of the battery cage 373. A number of clip feet 346 (four in the exemplary embodiment) may extend downward from the bottom of the battery cage 373 and a number of side clips 347 may be provided on the lateral sides of the battery cage 373.

The battery carrier 326 may be attached to the base cover 359 by sliding the clip feet 346 along the inner wall of the base cover until the clip feet 346 engage the opposing shelves (not shown) formed on the inner wall of the base cover 359. Simultaneously, the side clips 347 may slide within the clip recesses 472 in the flange 473 at the top edge of the base cover 359 to appropriately align the battery carrier 326 with respect to the base cover 359. The battery carrier 326 is thereby secured to the base cover 359. The compression spring 465 mounted on the bobbin cap 410 may bias the battery pack 330 upward within the battery carrier 326 to abut the bottom surface of the top plate 509.

A lower portion of a circuit board 334 is mounted to the mounting pins 348 extending from the front side of the battery carrier 326 as best depicted in FIGS. 13A, 14, and 15C. The circuit board 334 may be positioned underneath the hermetic cover 381 mounted within the control system window 376 in the housing 316 and extend generally the length of the control system window 376. In addition to a microcontroller device (not shown) and a capacitor 333 (to reduce electrical noise in the voltage step-up portion of the control circuit), a number of components under control of the microcontroller may be mounted on the circuit board 334 and electrically connected to a circuit printed on the circuit board 334 to control the functionality of the toothbrush/flosser 310. For example, a number of LEDs 341 may be mounted to the circuit board 334 to provide operational mode and status information to a user. One or more light guides 339*a/b* may be mounted over the LEDs 341 in order to contain and collimate the light emitted by the LEDs and direct the light through the hermetic cover 381 and housing plate 385 to illuminate the mode indicators 388 and LED apertures 319 in the face plate 323. The light guides 339*a/b* may be formed with specifically shaped apertures that are positioned to fit around the LEDs 341. In this exemplary implementation, the upper light guide 339*a* may direct light from the LEDs 341 to specifically illuminate the mode indicators 388 (e.g., high speed brush, low speed brush, water flosser, and off as noted above). Also as shown in this implementation, the lower light guide 339*b* may direct light from the LEDs 341 to the LED apertures 319 to provide an indication of the power level of the battery pack 330 so the user will know when the battery pack 330 needs to be recharged. Additionally, the light guides may be made from rubber and thus act to damp vibration transfer from the motor 332 to the housing 316.

A pair of switches 345*a/b* may also be mounted on the circuit board 334 directly underneath respective button covers 322*a/b*. The button covers 322*a/b* may be flexible enough to allow a user to depress the button covers 322*a/b* and contact the switches underneath. Alternatively, the button covers 322*a/b* could be formed with posts that extend below the covers to actuate the switches 345*a/b* if the depth beneath the button covers 322*a/b* is too great. The switches 345*a/b* may be cycle switches used to select and control the various modes or functions of the toothbrush/flosser 310. For example, one switch might turn the toothbrush function on to a low speed from off with a first actuation, then to high speed with a second actuation, then to off with a third actuation. The second switch might be used to separately control the water pump in the base unit by turning the pump on at a low speed pulse with a first actuation, selecting a high speed pulse with a second actuation, and turning the pump in the base unit off with a third actuation. In some implementations, both the tooth brush function and the flosser function may be operable at the same time. In some implementations, an RF transmitter or transceiver (not shown) may be mounted on the circuit board 334 and connected to one of the switches for wireless control of a base unit equipped with an RF receiver or transceiver linked to its control system. In other implementations, other short range wireless protocols could be implemented, (e.g., using Bluetooth transceivers in the handle 311 and base unit). In other implementations, the handle 311 may be directly wired to the base unit to exercise control of the base unit. The wires may be separate from or incorporated with the fluid hose connected between the fluid inlet 414 and the base unit.

A pair of battery leads 331*a/b* may be connected to terminals of the batteries and extend to connect with the inductive charging coil 328 in order to recharge the battery pack 330. A separate pair of electrical leads may further connect the battery pack to the circuit board 334 for powering the control system, LED lights 341 and the motor 332. Alternatively, the battery leads 331*a/b* may be connected to terminals on the circuit board 334 to allow for microcontroller control of the charging process or to provide a conditioning circuit for the charging energy before it is connected to the battery pack 330.

As best depicted in FIGS. 13A, 13B, 14, 15C, 20A, and 20B, a bottom end of a drive train chassis 324 may be connected to the chassis mount 510 on the top of the battery carrier 326, e.g., by one or more screws, and extend upward therefrom. A motor 332 may be mounted within a motor tray 474 defined within a lower section of the chassis 324 such that the motor 332 is positioned directly above the spacer cavity 349 on the top of the battery carrier 326. A motor mount 475 may extend forward transverse to the longitudinal form of the chassis 324. The motor mount 475 may be secured to a top surface of the motor 332 by one or more fasteners, e.g., set screws that pass through apertures in the motor mount 475 and screw into threaded mounting apertures 511 in the top surface of the motor 332. When the motor 332 is anchored to the motor mount 475 on the chassis 324, the base of the motor 332 is positioned nominally within the spacer cavity 349 such that the motor contacts 421 are protected within the spacer cavity 349 and can be connected by electrical leads (not shown) to the circuit board 334.

A vibration isolator 356 may be placed about the base of the chassis 324 at the joint with the battery carrier 326. The vibration isolator 356 further extends around the wall forming the chassis mount 510 on the battery carrier 326. The vibration isolator 356 may be formed of rubber or another elastomeric material and fills the gap between the chassis 324 and battery carrier 326 and the housing 316 to dampen the vibration of the motor 332 that otherwise may be imparted to the housing. The vibration isolator 356 also provides a soft mounting structure for the base of the drive train 336 with respect to the housing 316 rather than attaching the chassis 324 directly to a structure on the housing 316. The vibration isolator 356 also provides clocking (anti-rotation) for both the drive assembly 336 and the battery carrier 326. The vibration isolator 356 isolator also forms an isolator clamp 415n a back side of the chassis 324. This structure will be explained in greater detail below.

The motor mount 475 may further define a semi-circular shaft cutout 512 to provide clearance around an output shaft 337 of the motor 332. In one implementation, a spacer plate 420 may further be placed on top of the motor mount 475 and secured to the motor mount 475 by the same set screws connecting the motor mount 475 to the motor 332. The spacer plate 420 may have a similar semi-circular cutout 513 as the motor mount 475 in order to provide adequate clearance for the output shaft 337. The spacer plate 420 may be made of metal in order to both provide additional rigidity to the chassis 324 where the motor 332 is mounted and also to provide a long wearing surface adjacent the connection between the motor 332 and a drive assembly 336 should some of the components unintentionally interface with the spacer plate 420.

The chassis 324 further extends above the motor mount 475 to provide additional structural support for the drive assembly 336. The drive assembly 336, which is best depicted in FIGS. 13A, 13B, 14, 15C, and 20A-25B, includes an eccentric cam 353 that is press fit onto the output shaft 337 of the motor 332. As shown in FIGS. 25A and 25B, the eccentric cam 353 is formed with a cam post 366 extending off center from a top surface of a disk base 515. A shaft bore 514 extends through both the disk base 515 and the cam post 366 and receives the output shaft 337 of the motor 332. The shaft bore 514 is centered within the disk base 515; however, because the cam post 366 is offset with respect to the disk base 515, the shaft bore 514 is off center with respect to the cam post 366, thus defining the outer surface of the cam post 366 as a cam surface. The disk base 515 is provided to balance the eccentric cam 353 both longitudinally and radially with respect to the output shaft 337 to reduce the potential for motor vibration. Motor vibration is undesirable mechanically because it causes significant wear on the components of the drive system 336, it results in a larger load and strain on the motor 332, it results in greater battery drain, and it transfers vibration through the handle 311 to the user. The disk base 515 may also be formed with one or more balance recesses (not shown) in order to remove an appropriate amount of mass at appropriate locations to refine the balance on the output shaft 337.

A dog bone coupler 352 may be connected with the cam post 366 as the first link in a four bar linkage in order to drive the drive system 336 with the motor 332. A support bushing 354 may be seated within a cam aperture 365 of the dog bone coupler 352 and press fit around the cam post 366. In one exemplary embodiment, a bearing race of ball bearings, needle bearings, or any other appropriate friction reducing structure may be substituted as the support bushing 354. As shown, the output shaft 337 may extend entirely through and above the eccentric cam 353. An end bushing 367 may be placed on the end of the output shaft 337 above the cam bushing 354 to hold the cam bushing 354 and the eccentric post 366 in place. The chassis 324 may further provide an eccentric cap bracket 476 that extends horizontally outward from a frame of chassis 324 in the form of a shelf with a disk-shaped eccentric cap aperture 517 that is positioned on top of the end bushing 367. In some embodiments, the end bushing 367 may be press fit within the eccentric cap aperture 517. The eccentric cap bracket 476 helps prevent wobble that could be generated by the motor 332 or the output shaft 337 that result from only having a single point of restraint on the output shaft 337. It should be considered that the disk base 515 may also be used to take into account the mass of the support bushing 354, the end bushing 367, and the dog bone coupler 352 on the balance of the output shaft 337 and any balance recess in the disk base 515 can be sized and shaped to do so.

The second half of the dog bone coupler 352 defines a drive aperture 369 that receives a drive bushing 368 press fit therein, which in turn receives a lower end of a rocker drive shaft 372 press fit therein. The rocker drive shaft 372 is thus able to freely pivot with low resistance within the drive aperture 369. An upper end of the rocker drive shaft 372 is received in a driver nubbin 371 extending from a rear surface of a rocker arm 350. The rocker arm 350 is positioned above and offset from the output shaft 337. In the exemplary implementation shown, the rocker drive shaft 372 is a cylindrical pin that may be press fit into receiving aperture in the driver nubbin 371. In exemplary alternative embodiments, the rocker drive shaft 372 may have a keyed or knurled shape that fits within a correspondingly shaped aperture in the driver nubbin 371 to prevent rotation or slippage there between, limiting any rotation to the dog bone coupler 352 around the bottom portion of the rocker drive shaft 372. In yet another embodiment, the upper portion of the rocker drive shaft 372 may be keyed and the rocker arm 350 may be insert molded around the upper portion of the rocker drive shaft 372, thereby preventing relative movement or slippage therebetween.

A front surface of the rocker arm 350 may define an aperture or shaft cavity 363 into which the brush shaft 320 is inserted and mechanically connected. The shaft cavity 363 is aligned with an axis A parallel to, but offset from, an axis B of the rocker drive shaft 372 on the opposite side of the rocker arm 350. The rear or distal end of the brush shaft 320 inserted into the shaft cavity 363 may be keyed and fit within a reciprocal keyway formed in the shaft cavity 363 in order to prevent rotation between the brush shaft 320 and the rocker arm 350. In some implementations, the brush shaft 320 may be ultrasonically welded to the rocker arm 350. In other implementations, the rocker arm 350 may be insert molded about the brush shaft 350 to form a strong bond between the two components. In any of these ways, the output shaft 337 of the motor 332 is thereby coupled with the rocker arm 350 via the dog bone coupler 352 and further to the brush shaft 320 via the rocker arm 350, forming a four-bar linkage.

Similar to the eccentric cam 353, the rocker arm 350 may be formed with additional mass used to balance the rocker arm 350 about the brush shaft 350 to minimize undesired wobble or vibration in the brush shaft. As shown in the figures, this additional mass may be modeled and molded in an appropriate form and position on the rocker arm 350. In the embodiment shown, a balance arm 362 is molded to extend from the body of the rocker arm 350. An aperture is formed in the balance arm 362 in order to receive additional mass elements of different density in order to appropriately balance the rocker arm 350 for different configurations of the toothbrush/flosser device 310.

In this implementation, the rocker arm 350 further defines a fluid passage 518 that extends from an inlet barb 370, which is oriented generally parallel with respect to the longitudinal axis of the toothbrush/flosser device 110, and bends laterally across the rocker arm 350 to intersect with the shaft cavity 363. The brush shaft 320 mounted within the shaft cavity 363 of the rocker arm 350 may have a keyed fluid inlet 486 formed as a cutout in the sidewall of the brush shaft 320 at the proximal or rear end that is aligned with the lateral branch of the fluid passage 518 within the rocker arm 350, thereby allowing fluid to flow from fluid passage 518 in the rocker arm 148 into the fluid lumen 452 in the brush shaft 320. In some embodiments, the rocker arm 350 may be made of a moulded plastic material. In order to mould the transverse portion of the fluid passage 518 in the rocker arm 350, a mould insert is required to provide form to the fluid passage 518. Thus, an aperture in the sidewall of the rocker arm 350 remains where the transverse mold insert was placed and removed. In such an implementation, a plug 364 may be inserted into the aperture in the sidewall of the rocker arm 350 to seal the fluid passage 518. The plug 364 may be fixed in place with an adhesive or ultrasonically welded in place in the rocker arm 350.

The outer diameter of the brush shaft 320 varies between the base end 314 and the brush end 312. Starting at the based end 314, the brush shaft 320 may have a rocker connection 485 of a first diameter that is configured to seat within the shaft aperture 363 in the rocker arm 350. Moving toward the brush end 312, the brush shaft 320 may have a first bearing mount 487a of a second diameter larger than the first upon which a rear bearing race 340 is press fit. The brush shaft 320 may have a bearing separator section 388 of a third diameter larger than the second that prevents movement of the rear bearing race 340 in a distal direction. A balance weight 491 in the form of a cylinder may further be placed around the bearing separator section 388 of the brush shaft 320 if additional balancing of the brush shaft 320 is desired. The brush shaft 320 may have a second bearing mount 487b of a fourth diameter that is equal to the second upon which a front bearing race 342 is press fit. The widths of the first and second bearing mounts 487a/b may generally be congruent with the widths of the bearing races 340, 342. The balance weight 491 may have a length that is shorter than the distance between the first and second bearing mounts 487a/b.

The chassis 324 may extend from the eccentric cap 476 to support certain sections of the brush shaft 320. A rear pillow block 447 may be formed in the chassis 324 and align with and conform to the outer diameter of the rear bearing race 340. Similarly, a front pillow block 478 may be formed at the distal end of the chassis 324 and align with and conform to the outer diameter of the front bearing race 342. A shaft tray 479 may be formed in the chassis 324 between the rear pillow block 340 and the front pillow block 342 to support the balance weight. The shaft tray 479 may conform to the outer diameter of the balance weight 491 or it may be set off from the outer diameter of the balance weight 491 to ensure that the brush shaft 320 has adequate rotational clearance.

A rear bearing bracket 344 may be fastened to the chassis 324 (e.g., with screws) in alignment with the rear bearing race 340 and the rear pillow block 477 to hold the rear bearing race 340 in place. Similarly, a front bearing bracket 338 may be fastened to the chassis 324 (e.g., with screws) through mount tabs 482 in alignment with the front bearing race 342 and the front pillow block 478 to hold the front bearing race 342 in place. In some embodiments, an O-ring or similar dampening material may be placed around the bearing races 340, 342 between them and the respective bearing brackets 338, 344 and pillow blocks 477, 478 to dampen any transmission of vibration from the brush shaft 320 to the housing 316 or from the motor 332 mounted on the chassis 324 to the brush shaft 320. The rear bearing bracket 344 may further be formed with a circuit board support 480 (e.g., posts) that connect with the brush end 312 of the circuit board 334 to provide a set off distance from the drive train 336. The front bearing mount 338 may further be formed with an annular boot mount 484 that slides around the distal end of the brush shaft 320 to a position adjacent the front bearing race 342. A sidewall of the front bearing mount 338 may also form a capacitor tray 481 to support the capacitor 333 connected to the brush end 312 of the circuit board 334.

The brush shaft 320 may have a shaft seal section 351 of a fifth diameter smaller than the fourth diameter that is sized to fit through the shaft aperture in the housing 316 and upon which a boot seal 321 is mounted. The base of the boot seal 321 may be connected to the boot mount 484 of the front bearing bracket 338. An annular rib 493 is formed on an inner wall of the boot seal 321 and fits within an annular recess 483 in the boot mount 484 to secure the boot seal 321 to the front bearing bracket 338. The boot seal 321 tapers in diameter toward its distal end such that a distal aperture 520 in the boot seal 321 fits snugly against the brush shaft 320. An annular recess 492 is also formed in the boot seal 321 adjacent the distal aperture 520 within which a seal band 355 (e.g., a brass ring) is placed to clamp the boot seal 321 to the shaft seal section 351 of the brush shaft 320.

A portion of the brush shaft 320 extends distally through the shaft aperture 379 in the housing 316. The exposed portion of the brush shaft 320 defines an annular clip recess 489 toward a proximal or rear end and an alignment tip 490 at the distal or front end. The alignment tip 490 may be take the form of one or more flattened or keyed surfaces that may provide appropriate alignment of the brush tip 325 with respect to the handle 311 when the brush tip 325 is connected thereto.

A fluid tube 415 extends from the fluid connector 467 on the bobbin cap 410 to the fluid port 370 on the rocker arm 350. The base end 314 of the fluid tube 415 fits over the connector barb 469 on the fluid connector 467 and is fastened in place by a locking sleeve 416. Similarly, the brush end 312 of the fluid tube 415 is positioned over the barb on the fluid port 370 and a locking sleeve 418 secures the connection. A tube clamp 357 further holds a bottom portion of the fluid tube 415 against the battery carrier 326.

The tube clamp 357 may be fastened to the battery carrier 326 (e.g., with screws) and the fluid tube 415 is clamped between the two. Additionally, the fluid tube 415 is restrained within the housing 316 by the isolator clamp 358 on the back of the vibration isolator 356. The isolator clamp 358 defines a channel between two walls extending from the back of the vibration isolator 356 that are separated by a small gap. The elastomeric material forming the vibration isolator 356 is flexible such that the vibration isolator 356 can be bent to open the gap in the isolator clamp 358 wide enough to insert the fluid tube 415 into the isolator clamp 358. Alternatively, the fluid tube 415 could be advanced longitudinally through the isolator clamp 358 from either end before it is connected to the connector barb 469 or the fluid port 370 on the rocker arm 350.

One of several exemplary brush tips 325 is depicted in greater detail in FIGS. 26-32. The brush tip 325 may be easily connected to or disconnected from the brush shaft 320 extending from the brush end of the handle 311. The brush tip 325 is composed primarily of a tip shaft 423 and a brush head 424. The tip shaft 423 defines a tip fluid passage 440 therethrough to the brush head 424. The brush head 424 defines a bristle base 427 composed of a plurality of recesses into which a plurality of bristle tufts 327 may be inserted and glued in place. In addition, the brush head 424 defines a nozzle aperture 425 that opens in the bristle base 427 in an area surrounded by bristle tufts 327. A colored ring 448 may be attached to the base of the tip shaft 423 to allow for multiple users of the toothbrush/flosser 310 to easily identify their personal brush tip 325 for attachment to the handle 311. The base of the tip shaft may define a recess with a retention groove 446. The inner wall of the colored ring 448 may define a number of retention detents 447 that may snap into the retention groove to retain the colored ring 448 around the base of the brush tip 325.

An elastomeric water jet nozzle 428 is positioned within the nozzle aperture 425 and extends normal to the bristle base 427 approximately the same distance as the bristle tufts 327. The nozzle 428 defines a fluid lumen, is generally conical, and tapers in diameter from its base, which is received in the nozzle aperture 425, to its tip. A cavity 523 is formed in the back of the brush head 424 to provide access to the nozzle aperture 425 and a fluid flow connection between the nozzle aperture 425 and the tip fluid passage 440. The cavity 523 may be enclosed by a brush head plug 426 that snaps into the sidewalls defining the cavity 523 and is ultrasonically welded or otherwise adhered to provide a fluid-tight seal in the brush head 424.

A cylindrical recessed band 521 is formed in a sidewall of the nozzle 428 adjacent the base, which thus appears as a raised band 522. The outer diameter of the recessed band 521 is generally congruent with the diameter of the nozzle aperture 425 while the outer diameter of the raised band 522 is larger than the diameter of the nozzle aperture 425. When the nozzle 428 is inserted into the nozzle aperture 425 from the cavity 523 in the rear of the brush head 424, the recessed band 521 fits snugly within the nozzle aperture 425 and the raised band 522 abuts the back of the bristle base 427, preventing the nozzle 428 from being pushed through the nozzle aperture 425 when under pressure. In addition, a nozzle insert 429, e.g., a brass tube with a rear flange, may be inserted into the base of the nozzle 428 to prevent the nozzle 428 from bending or collapsing under high water pressure and contact with teeth and thereby dislodging from the nozzle aperture 425.

An alignment mount 422 may be inserted into and permanently affixed within the tip fluid passage 440 from the base end 314 of the brush tip 325. In the exemplary implementation shown, the alignment mount 422 may be generally formed as a frustum with open sidewalls. A top ring 494 is joined to a larger diameter bottom ring 495 by an alignment rib 496 on one side and a support rib 407 laterally opposed thereto. The alignment rib 496 may mate with opposing structures within the sidewalls of the tip shaft 423 defining the inner diameter of the tip fluid passage 440 to appropriately align the alignment insert 422 before the brush shaft 320 is inserted. The top ring 494 defines an outlet aperture 451 for transmitting fluid flow from the shaft outlet 452 into the tip fluid passage 440. The bottom ring 495 defines a shaft aperture 452 for receipt of the shaft tip 490. The inner side of the alignment rib 496 mates with the alignment tip 490 on the brush shaft 320 in order to align the brush tip 325 appropriately on the brush shaft 320.

Figure 27:
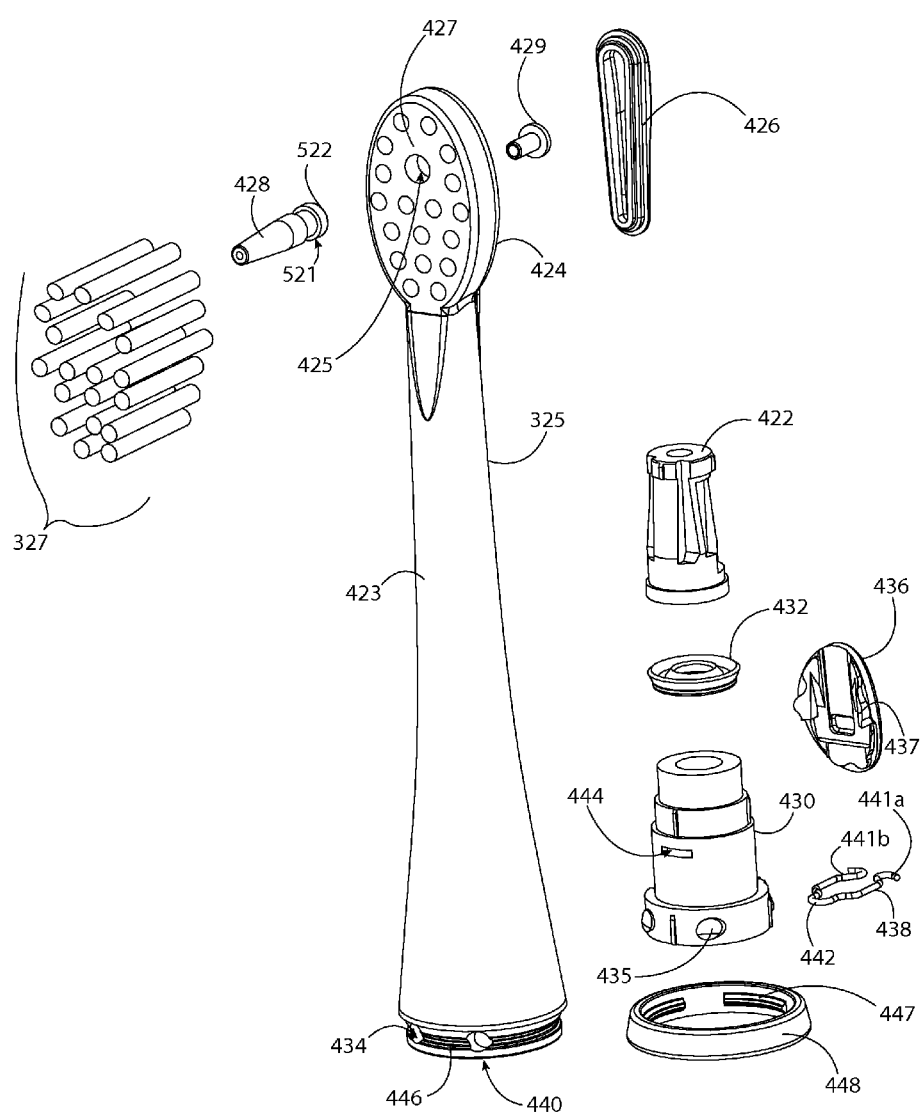
FIG. 27 is an exploded isometric view of the brush tip of FIG. 26.
Figure 28:
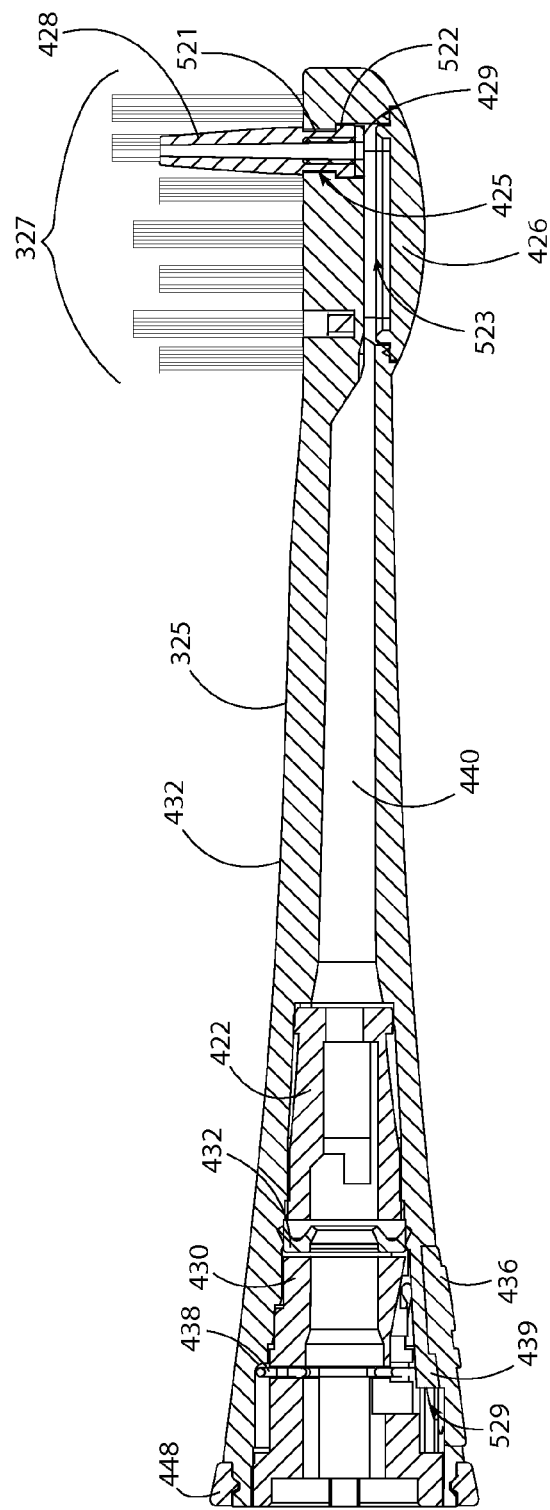
FIG. 28 is a cross section view of the brush tip of FIG. 26 taken along line 28-28 in FIG. 26.
Figure 29:
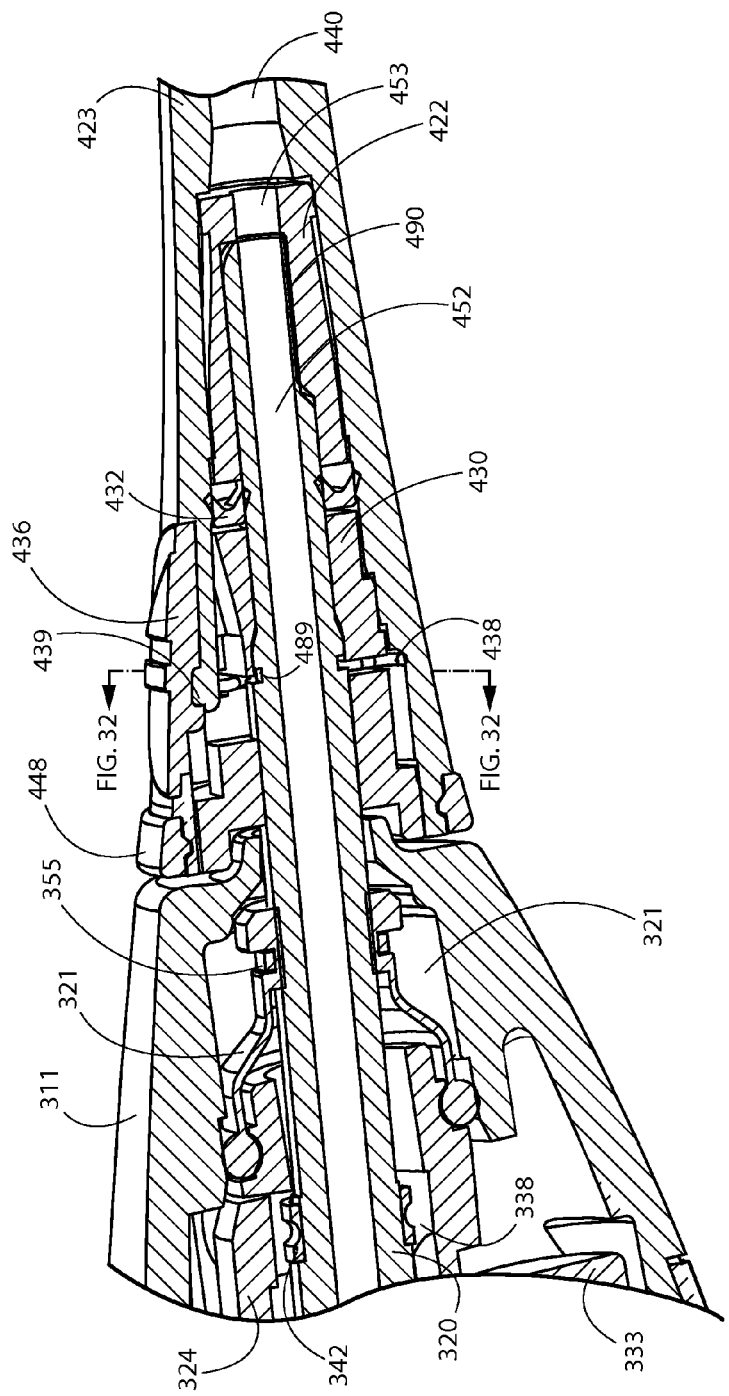
FIG. 29 is an enlarged, right side, isometric view in cross section of the toothbrush/flosser of FIG. 12A taken along line 14-14 in FIG. 12A detailing the top portion of the handle and the base of the brush tip.

A cup seal 432 may be inserted into the tip fluid passage 440 of the brush shaft 320 after the alignment insert 422 and may be held in place against the alignment insert 422 by a shaft retainer 430. In this exemplary implementation, the shaft retainer 430 is formed as a series of stacked cylinders with decreasing diameters as they extend toward the brush head 424. The shaft retainer 430 defines a retainer lumen 449 through which the brush shaft 320 passes when the brush tip 325 is placed on the handle 311. A number of short, beveled retainer posts 435 extend outward from the sidewall of the base cylinder 525 of the largest diameter. A pair of compression slots 431 is also formed within the base cylinder 525. As shown in FIG. 27, a number of retainer holes 434 corresponding to the retainer posts 435 are formed in the tip shaft 423 adjacent a base end thereof. When the base cylinder 525 is inserted into the brush tip 325, the compression slots 431 allow the base cylinder 525 to compress slightly so that the retainer posts 435 can enter the lumen of the tip shaft 423 and then expand again when the retainer posts 435 seat within the retainer holes 434 to retain the shaft retainer 430 within the tip shaft 423.

Figure 32:
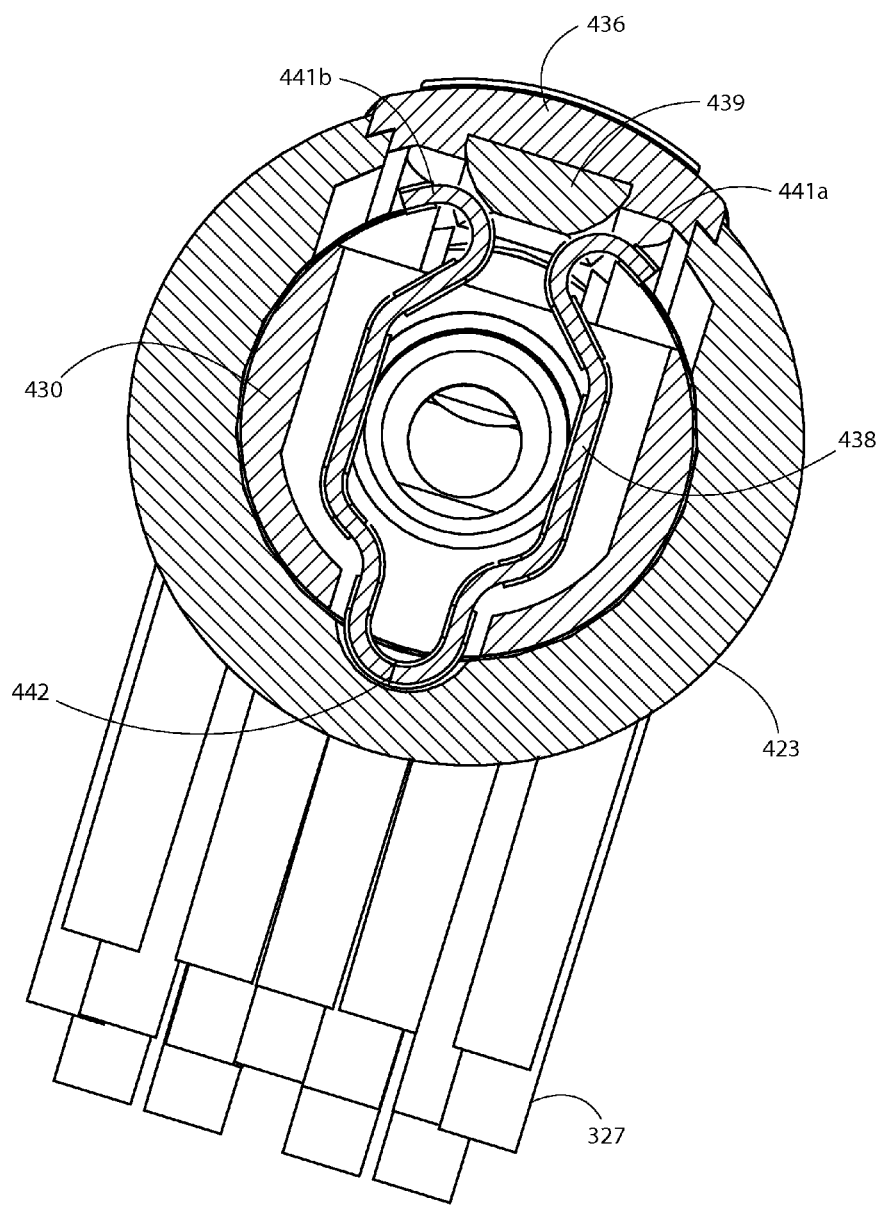
FIG. 32 is a bottom plan view in cross section of the brush tip taken along line 32-32 in FIG. 29.

A button opening 445 is formed in a second cylinder 526 adjacent the base cylinder 525 on the rear sidewall of the shaft retainer 430 that extends through to the lumen 449. A clip slot 443 is also formed in the sidewall of the second cylinder 526 above the button opening 445. The clip slot 443 extends transversely through the shaft retainer 430 and extends out the front wall as a smaller clip slot outlet 444. The clip slot 443 is configured to retain a spring retainer clip 438 therein to secure the brush tip 325 to the brush shaft 320. The spring retainer clip 438 is formed from a piece of stiff wire to have a pair of clip arms 441a/b that oppose each other and are joined at a clip arch 442. The free ends of the clip arms 441a/b each form a reverse curve that opens away from the other. As shown in FIG. 32, when installed in the clip slot, the clip arch 442 extends through the clip slot outlet 444, the middle sections of the clip arms 441a/b are retained within the clip slot in the front wall, and the free ends of the clip arms 441a/b are exposed outside of the second cylinder 526.

Portions of the second cylinder 526 above the clip slot 443, a third cylinder 527 above the second cylinder 526, and a top cylinder 528 together define a lever recess 433 within the rear wall of the shaft retainer 430. An elastomeric release button 436 is mounted within a button opening 529 in the back side of the tip shaft 423 that is positioned directly across from the button opening 445 in the shaft retainer 430. A cantilevered clip lever 439 may extend downward within the button opening 529 from a top edge of the button opening 529 from which it depends. The clip lever 439 is oriented longitudinally within the sidewall of the tip shaft 423 and is configured to bend inward under pressure of the release button 436 and then return to its longitudinal position. The release button 436 may have a number of retaining features 437 on its back side that interface with corresponding features on the clip lever 439 and tip shaft 423 to connect the release button 436 to the tip shaft 423. In one exemplary embodiment, the release button 436 may be adhered to the clip lever 439 and compliance fit within the button opening 529.

To connect a brush tip 325 to the brush shaft 320, a user need only place the brush tip 325 on the brush shaft 320 and rotate the brush tip 325 until the alignment tip 490 of the brush shaft 320 mates with the key surface 524 of the alignment insert 422 within the tip shaft 423. Then the user needs to press the brush tip 325 onto the brush shaft 320 until the lateral arms 441a/b of the spring retainer clip 438 seat within the clip recess 489 on the brush shaft 320. The diameter of the brush shaft 320 increases along a beveled edge immediately adjacent the clip recess 489. The arms 441a/b of the spring retainer clip 438 expand laterally outward along this edge and then, when past the beveled edge, the arms 441a/b contract laterally inward to lodge within the clip recess 489. The separation distance between the lateral arms 441a/b when at rest is selected to be congruent with the diameter of the clip recess 489. Typically, an audible "click" can be heard by the user when the lateral arms 441a/b lodge within the clip recess 489 so that the user knows that the brush tip 325 is securely attached to the handle 311. The gauge, material strength, and elasticity of the wire forming the spring retainer clip 438 are specifically chosen to ensure retention of the brush tip 325 on the brush shaft 320 under the operating pressures of the water jet function and further to reliably expand during engagement and disengagement of the brush tip 325 over an appropriate number of cycles equivalent to or greater than an estimated life of the bristles 327.

To disconnect a brush tip 325 from the brush shaft 320, the user need merely press down on the release button 436 and pull the brush tip 235 away from the handle 311. The depression of the release button 436 bends the clip lever 439 inward and pushes it in between the free ends of the clip arms 441a/b. The width of the clip lever 439 is wider than the gap between the clip arms 441a/b so the clip arms 441a/b are pushed apart. The width of the clip lever 439 is chosen such that the clip arms 441a/b spread apart wider than the outer diameter of the brush shaft 320 adjacent the clip recess 489 therein so that the brush tip 325 can be easily removed from the brush shaft 320.

In order to operate the toothbrush/flosser 310, the removable base must be attached to the handle 311. Further, for the water jet flosser function to operate, the inlet port 414 on the removable base 318 must be attached via a fluid hose to a water jet base unit with a pump and a reservoir. The removable base 318 may be attached to the handle 311 by aligning the arch-shaped fluid channel casing 460 with the arched cutout 304 in the housing 316 and inserting the valve post 459 into the induction port 317 of the coil bobbin 400. A fluid tight seal between the valve post 459 and the coil bobbin 400 is provided by the coil seal 335 in the induction port 317 fitting around and against the valve post 459. When the arched cutout 304 and the arch-shaped fluid channel casing 460 are aligned, the latch feet 403 extending from the coil bobbin 400 will necessarily align with and extend through both the latch slots 458 in the base cap 389 and the latch apertures 306 in the latch plate 390. The user may press the removable base 318 into the bottom opening 380 of the housing 316 until the bottom edge of the housing is flush against the base plate 390. This ensures that the compression spring 465 is in compression against the batteries 330, thus pushing the chassis 324 and drive train 336 into a firm but soft mount relationship with the housing 316, and further ensures that the latch feet 403 are in a proper position for engagement by the latch fingers 398 on the latch plate 391. The user then grasps the base release levers 313 and turns the base plate 391 clockwise against the bias of the latch spring 392 (which maintains the latch plate in an open position when the removable base 318 is not attached to the handle 311) to latch the latch feet 403 under the latch fingers 398 and thus connect the removable base 318 to the handle 311.

When the removable base 318 is attached to the handle 311, the lower poppet 394 engages the upper poppet 412. In particular, the plunger 413 in the upper poppet 412 interfaces with the shallow recess in the upper surface of the lower poppet 394. The lower poppet 394 is pushed away from a sealing interface position against the post aperture 462, compressing the lower poppet spring 393 in the process. Simultaneously, the upper poppet 412 is pushed away from a sealing interface position against the bobbin aperture 504, compressing the upper poppet spring 411 in the process. In this position, a fluid flow pathway from the fluid inlet 414 to the nozzle 428 in the brush tip 325 is opened. Fluid from the water flosser base unit travels through the fluid inlet 414, through the fluid channel 351 in the base cap 389, through the fluid channel 396 formed between the base plate 390 and the base cap 389, around the lower poppet 394 in the valve post 459, through the post aperture 504, into the induction port 317, through the bobbin aperture 504, around the upper poppet 412, through the fluid outlet 406 and the fluid chamber 508 formed between the coil bobbin 400 and the bobbin cap 410, and to the connector barb 469. Fluid then transfers from the connector barb 469 into and through the fluid tube 415 to the fluid port 370 in the rocker arm 350, through the transverse fluid passage 518 in the rocker arm 350, into the fluid lumen 452 defined in the brush shaft 320, out the outlet port 453 of the shaft, into the tip fluid passage 440, and finally out the nozzle 428. The cup seal 432 in the tip shaft 423 provides a fluid seal between the interior of the brush tip 325 and the outer diameter of the brush shaft 320. This prevents the fluid that is exiting the fluid outlet 453 of the brush shaft 320 from escaping out the base of the brush tip 325 and forces the fluid to continue on to the cavity 523 in the brush head 424.

As noted previously, the fluid flow from a base pump unit may be controlled by the switches 345a/b in the handle 311 of the toothbrush/flosser 310. The switches 345a/b may also be used to control the action of the brush tip 325. Selection of one of the switches 345a/b may actuate the motor 332 at either a low or high speed. The motor 332 may be a two-speed motor or a variable speed motor and the microcontroller on the circuit board 334 may vary the voltage to the motor 332 at discrete and controlled levels and thereby change the motor speed between low and high options. The motor speed is preferably sonic, from 13,000 RPM to 17,000 RPM and often may be 15,000 RPM.

Once the motor 332 is actuated by a switch 345a/b, the output shaft 37, which is fixed within the shaft bore 514 of the eccentric cam 514, rotates continuously in a single rotational direction until the switch 345a/b is depressed to deactivate the motor 332 and stop its rotation. The rotation of the eccentric cam 353 causes the dog bone coupler 352 to move back and forth or, oscillate, primarily in an oblong or linear orientation.

The rocker drive shaft 372 connecting the dog bone coupler 352 to the rocker arm 350 pivots within the bushing 368 as the dog bone coupler 352 reciprocates but is fixed within the driver nubbin 371 in the rocker arm 350. The back and forth or oscillating displacement of the dog bone coupler 352 causes the rocker arm 350 to pivot back and forth about the axis passing through the center of the brush shaft 320. As a result, the brush shaft 320, which is mounted in the aperture 363 in the rocker arm 358, pivots back and forth about the longitudinal axis of the brush shaft 320. The pivot movement of the brush shaft 320 causes the brush head 424 to move in about a 5 degree arc at sonic speeds. The alignment insert 422 in the tip shaft 423 is permanently assembled to the interior of the tip shaft 423 and serves to locate and key the brush tip 325 relative to the brush shaft 320. This forces the brush head 424 to follow the oscillation of the brush shaft 320 and thereby produces sonic movement of the bristle tufts 327.

It may be appreciated that the sonic drive system of the handle 311 could be constructed in several alternate configurations from that which is described above. For example, the drive system could be designed to convert the input motion into rotary oscillatory output motion about an axis perpendicular to the brush axis. Similarly, the drive system could be designed to convert the input motion into linear oscillatory motion on an axis approximately parallel to the brush axis. Alternately, the drive system could be designed to make use of a vibratory system that would cause the brush head to move in a somewhat random pattern.

When the toothbrush/flosser 310 is low on power, the user may recharge the battery pack 330 by removing the removable base 318. The user may grasp the base release levers 313 and turn them counter clockwise to release the interface between the latch fingers 398 on the latch plate 390 and the latch feet 402 on the coil bobbin 400 and pull the removable base 318 off of the handle 311. When the removable base 318 is removed from the handle 311, the lower poppet 394 is forced to seal the post aperture 462 by the lower poppet spring 393. This prevents any residual water in the hose from the base pump unit from leaking, or alternatively prevents a leak if the base unit is accidentally turned on while the hose is still attached to the removable base 318. Similarly, the upper poppet 412 is forced to seal the bobbin aperture 504 by the upper poppet spring 411. This prevents any residual water in the handle 311 from leaking. The handle 316 may then be placed on an inductive charging post (not shown) with an inductive post sized to fit within the induction port 317. The inductive post may be designed to have a center recess in the top surface so as not to engage the plunger 413 on of the upper poppet 412 and disrupt the seal against leakage from residual fluid within the handle 311.

Another exemplary embodiment of a brush tip 625 is presented in FIGS. 33A-33C. In this embodiment, the connection structure for connecting the brush tip 625 to a brush shaft is the same as in the embodiment of FIGS. 26-32 using the alignment insert 622, cup seal 632, shaft retainer 630, and release button 636. A colored ring 648 may be attached to the base of the tip shaft 623 to allow for multiple users of the toothbrush/flosser to easily identify their personal brush tip 625 for attachment to the handle. The configuration of the brush head 624 is the primary difference. The tip shaft 623 defines a tip fluid passage 640 therethrough to the brush head 624. The brush head 624 defines a bristle base 637 composed of a plurality of recesses into which a plurality of bristle tufts 627 may be inserted and glued in place. In addition, a cylindrical nozzle enclosure 645 extends normally from the bristle base 637 in an area surrounded by bristle tufts 627 to about one quarter to one third the height of the bristle tufts 627. The nozzle enclosure 645 defines a nozzle aperture 635 that opens in a top surface of the nozzle enclosure 645.

An elastomeric water jet nozzle 828 is positioned within the nozzle enclosure 845 and extends upward out of the nozzle aperture 635 approximately two thirds the height of the bristle tufts 627. The nozzle 628 defines a fluid lumen, is generally cylindrical, and defines a cup-shaped flange 642 at its base, which is received in nozzle enclosure 645 and is retained thereby. The nozzle aperture 635 is slightly larger in diameter than the outer diameter of the nozzle above the flange 642 and smaller in diameter than the diameter of the flange 642. A cavity 633 is formed in the back of the brush head 624 to provide access to the nozzle enclosure 645 and a fluid flow connection between the nozzle enclosure 645 and the tip fluid passage 640. The nozzle enclosure 645 may extend below the bristle base 637 to the bottom of the cavity 633. As shown in FIG. 33B, this allows the nozzle 628 to drop below the height of the bristle tufts 627 when the water jet is not in operation and thereby not interfere with the brushing modes. The cavity 633 may be enclosed by a brush head plug 626 that snaps into the sidewalls defining the cavity 633 and is ultrasonically welded or otherwise adhered to provide a fluid-tight seal in the brush head 624.

When the water jet function is selected on the handle, the pressurized water flow through the tip fluid channel 640 and into the nozzle enclosure 645 pushes on the flange 642 and causes the nozzle 628 to rise within the nozzle enclosure 645. The nozzle 628 extends through the nozzle aperture 635 until the top of the flange 642 interfaces with the top of the nozzle enclosure 645 around the nozzle aperture 635 as shown in FIG. 33C. The nozzle 628 thus rises above the height of the bristle tufts 627. This extended, exposed nozzle location provides the user with the necessary feedback to accurately position the nozzle 628 and fluid stream along the gum line. When the water jet mode is discontinued, the nozzle 628 may fall within the nozzle enclosure 645 back to the base or it can be pushed downward into the nozzle enclosure 645 with a finger or through brushing action against a user's teeth.

Figures 34A, 34B:
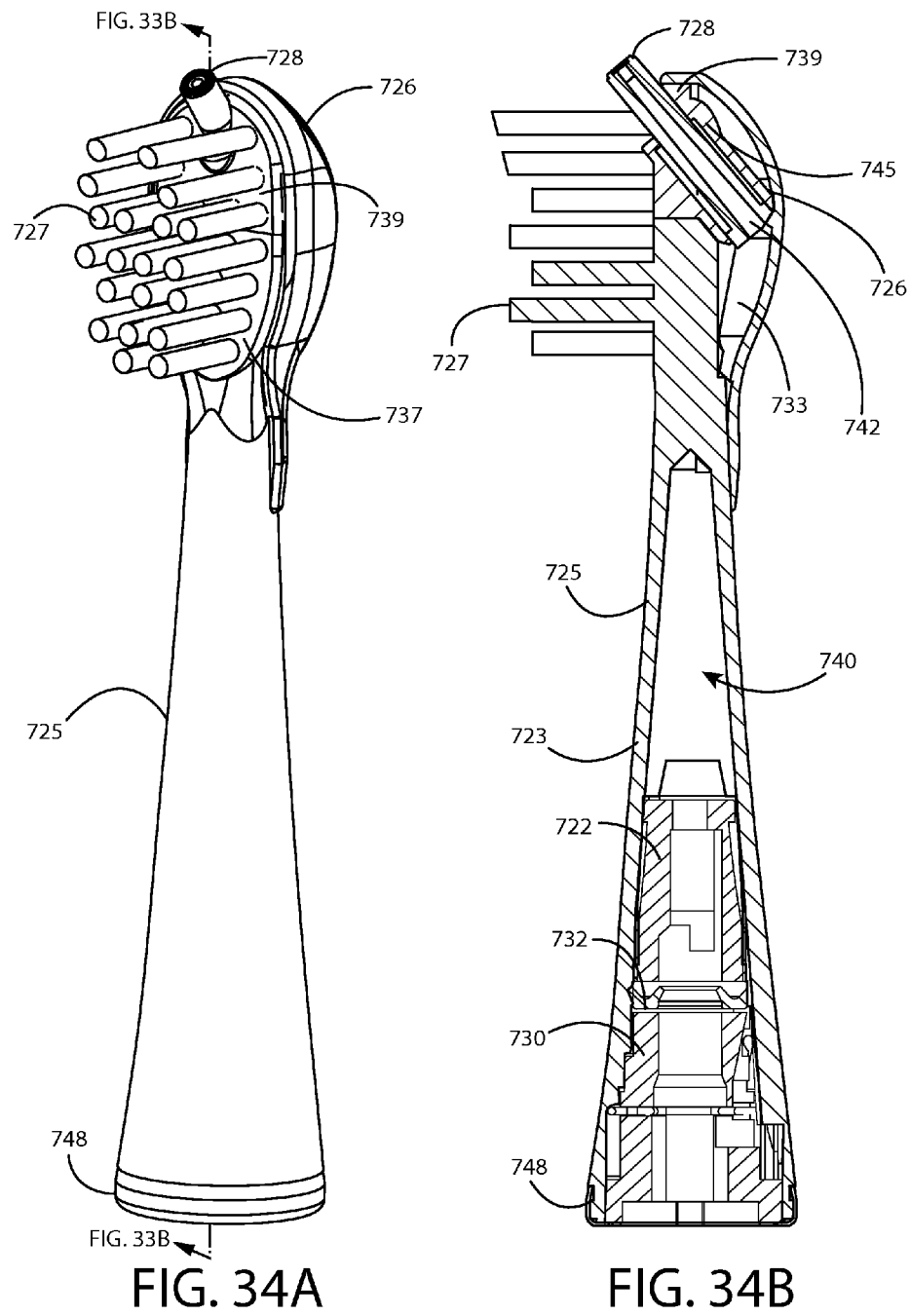
FIG. 34A is an isometric view of a third exemplary implementation of a removable toothbrush/flosser head.
FIG. 34B is a cross section view of the toothbrush/flosser head of FIG. 35A taken along line 34B-34B in FIG. 34A.

A further exemplary embodiment of a brush tip 725 is presented in FIGS. 34A and 34B. In this embodiment, the connection structure for connecting the brush tip 725 to a brush shaft is the same as in the embodiment of FIGS. 26-32 using the alignment insert 722, cup seal 732, shaft retainer 730, and release button 736. A colored ring 748 may be attached to the base of the tip shaft 723 to allow for multiple users of the toothbrush/flosser to easily identify their personal brush tip 725 for attachment to the handle. The configuration of the brush head 724 is the primary difference. The tip shaft 723 defines a tip fluid passage 740 therethrough to the brush head 724. The brush head 724 defines part of a bristle base 737 composed of a plurality of recesses into which a plurality of bristle tufts 627 may be inserted and glued in place. A second bristle base 739 may be separately formed from the tip shaft 723 and connected to the bristle base 737 (e.g., by ultrasonic welding). In addition, a cylindrical nozzle enclosure 745 is formed within the second bristle base 739 at an obtuse angle with respect to the surface plane of the second bristle base 739. The nozzle enclosure 745 emerges in surface plane of the second bristle base 739 adjacent the distal tip of the brush head 724 in a position directed distally away from the bristle tufts 727. The nozzle enclosure 745 defines a nozzle aperture 735 that opens in a top surface of the nozzle enclosure 745.

An elastomeric water jet nozzle 728 is positioned within the nozzle enclosure 645 and extends out of the nozzle aperture 735 distally at the same angle as the nozzle enclosure 745 with respect to the surface plane of the second bristle base 739. The nozzle 728 defines a fluid lumen, is generally cylindrical, and defines a flange 742 at its base, which is received in nozzle enclosure 745 and is retained thereby. The nozzle aperture 735 is slightly larger in diameter than the outer diameter of the nozzle 728 above the flange 742 and smaller in diameter than the diameter of the flange 742. A cavity 733 is formed in the back of the brush head 724 to provide access to the nozzle enclosure 745 and a fluid flow connection between the nozzle enclosure 745 and the tip fluid passage 740. The nozzle enclosure 745 may extend at an angle below the bristle base 739 to the bottom of the cavity 733. As shown in FIG. 34B, this allows the nozzle 728 to stay out of the way of the bristle tufts 627 when the water jet is not in operation and thereby not interfere with the brushing modes. The cavity 733 may be enclosed by a brush head cover 726 that is overmoulded or ultrasonically welded around the bristle bases 737, 739 to define the cavity 733 and provide a fluid-tight seal in the brush head 624.

When the water jet function is selected on the handle, the pressurized water flow through the tip fluid passage 740 and into the nozzle enclosure 745 pushes on the flange 742 and causes the nozzle 728 to extend within the nozzle enclosure 745. The nozzle 728 extends through the nozzle aperture 735 until the top of the flange 742 interfaces with the top of the nozzle enclosure 745 around the nozzle aperture 735. The nozzle 728 thus rises to extend beyond the distal end of the brush head 724. When the water jet mode is discontinued, the nozzle 728 may slide or fall within the nozzle enclosure 745 back to the base or it can be pushed downward into the nozzle enclosure 745 with a finger or through brushing action against a user's teeth.

Figure 35A:
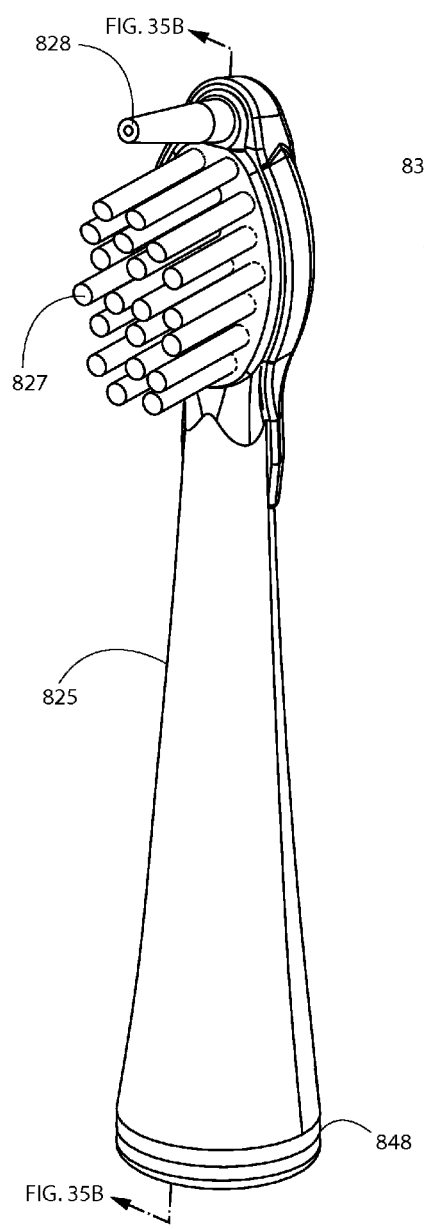
FIG. 35A is an isometric view of a fourth exemplary implementation of a removable toothbrush/flosser head.
Figure 35B:
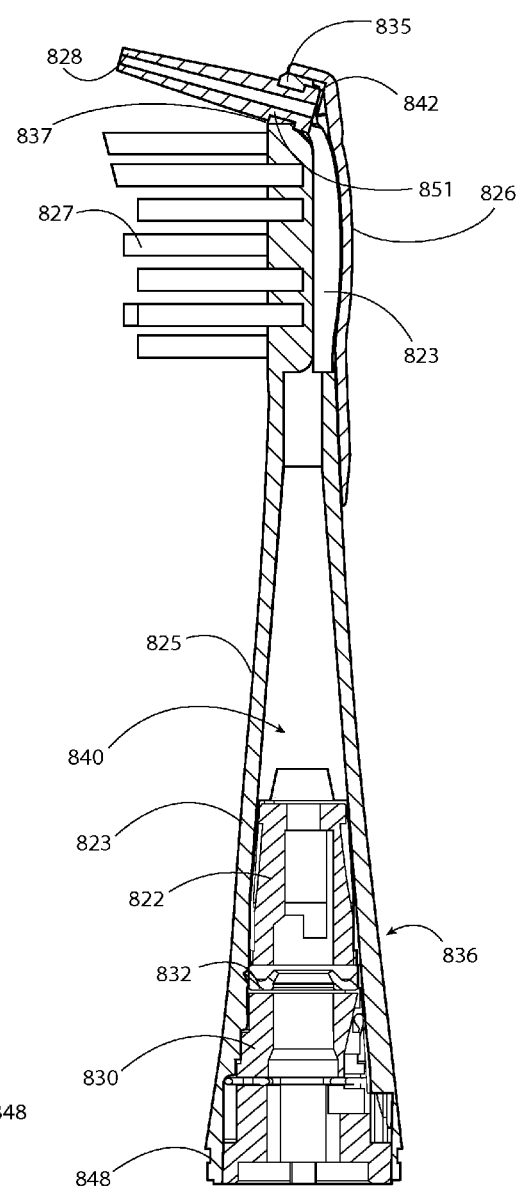
FIG. 35B is a cross section view of the toothbrush/flosser head of FIG. 35A taken along line 35B-35B in FIG. 35A.

An additional exemplary embodiment of a brush tip 825 is presented in FIGS. 35A and 35B. In this embodiment, the connection structure for connecting the brush tip 825 to a brush shaft is the same as in the embodiment of FIGS. 26-32 using the alignment insert 822, cup seal 832, shaft retainer 830, and release button 836. A colored ring 848 may be attached to the base of the tip shaft 823 to allow for multiple users of the toothbrush/flosser to easily identify their personal brush tip 825 for attachment to the handle. The configuration of the brush head 824 is the primary difference. The tip shaft 823 defines a tip fluid passage 840 therethrough to the brush head 824. The brush head 824 defines a bristle base 837 composed of a plurality of recesses into which a plurality of bristle tufts 827 may be inserted and glued in place.

In addition, the brush head 824 defines a nozzle aperture 835 that opens adjacent the distal tip of the brush head 824 in a position directed distally away from the bristle tufts 827. An elastomeric water jet nozzle 828 is positioned within the nozzle aperture 835 and extends distally at in a direction normal to the place of the nozzle aperture 835. The nozzle 828 defines a fluid lumen, is generally conical, and tapers in diameter from its base, which is received in the nozzle aperture 835, to its tip. A cavity 833 is formed in the back of the brush head 824 to provide access to the nozzle aperture 835 and a fluid flow connection between the nozzle aperture 835 and the tip fluid passage 840. The cavity 823 may be enclosed by a brush head cover 826 that that is overmoulded or ultrasonically welded around the bristle base 837 to define the cavity 833 and provide a fluid-tight seal in the brush head 824.

A cylindrical recessed band 851 is formed in a sidewall of the nozzle 828 adjacent the base, which thus appears as a raised band 842. The outer diameter of the recessed band 851 is generally congruent with the diameter of the nozzle aperture 835 while the outer diameter of the raised band 842 is larger than the diameter of the nozzle aperture 835. When the nozzle 828 is inserted into the nozzle aperture 835 from the cavity 833 in the rear of the brush head 824, the recessed band 851 fits snugly within the nozzle aperture 835 and the raised band 842 abuts the back of the bristle base 827, preventing the nozzle 828 from being pushed through the nozzle aperture 835 when under pressure. In some embodiments, a nozzle insert (not shown), e.g., a brass tube with a rear flange, may be inserted into the base of the nozzle 828 to prevent the nozzle 828 from bending or collapsing under high water pressure and contact with teeth and thereby dislodging from the nozzle aperture 835.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A toothbrush with combined sonic brushing and water flossing attributes comprising
   an electric motor including a drive shaft, wherein, when the electric motor is caused to operate, the drive shaft continuously rotates in a single direction;
   a brush tip supporting a brush head on a distal end and defining a fluid conduit therein;
   a drive assembly coupled between the drive shaft and the brush tip and configured to convert rotation of the drive shaft into sonic oscillation of the brush head whereby the brush tip pivots back and forth about a longitudinal axis of the brush tip;
   a fluid passage configured to transport fluid from a fluid source external to the toothbrush to the fluid conduit in the brush tip, wherein a portion of the fluid passage is formed within and defined by a portion of the drive assembly located between the motor and the base of the brush tip;

a removable baes plate comprising a fluid inlet in fluid communication with the fluid passage and configured to connect with the fluid source; and a first valve positioned within the fluid passage, wherein the first valve closes the fluid passage when the base plate is removed from the toothbrush and opens the fluid passage when the base plate is connected to the toothbrush.

2. The toothbrush of claim 1 further comprising
a motor control circuit in electrical communication with the electric motor; and
a motor control switch in electric communication with the motor control circuit; wherein
the motor control circuit is configured to change an output speed of the electric motor and thus a rotational speed of the drive shaft upon actuation of the motor control switch.

3. The toothbrush of claim 1 further comprising
a fluid control switch; and
a radio frequency transmitter connected to the fluid control switch and configured to transmit a signal to the fluid source to control fluid flow from the fluid source.

4. The toothbrush of claim 1 wherein the drive assembly further comprises
a coupler having a first end and a second end, and
an eccentric cam connected to the drive shaft; wherein
the first end of the coupler is operably coupled to the brush tip and the eccentric cam is rotationally received within the second end of the coupler;
rotation of the drive shaft causes the eccentric cam to rotate within the second end; and
rotation of the eccentric cam causes the coupler to oscillate.

5. The toothbrush of claim 4 further comprising
a chassis to which the electric motor is mounted; wherein
the chassis further defines a bracket that restrains the drive shaft to reduce wobble imparted by the eccentric cam.

6. The toothbrush of claim 1, wherein the brush head further comprises a fluid outlet in fluid communication with the fluid conduit in the brush tip.

7. The toothbrush of claim 6, wherein
the brush head further comprises a jet tip that forms the fluid outlet;
the jet tip extends to an extended position with respect to a surface of the brush head when fluid under pressure is in the fluid conduit of the brush head; and
the jet tip retracts to a retracted position with respect to a surface of the brush head when there is no fluid pressure in the fluid conduit of the brush head.

8. The toothbrush of claim 7, wherein
the brush head further comprises a plurality of bristles extending from the surface of the brush head;
a distal end of the jet tip extends beyond a distal end of the bristles when the jet tip is in the extended position; and
a distal end of the jet tip does not extend beyond a distal end of the bristles when the jet tip is in the retracted position.

9. The toothbrush of claim 1 further comprising a second valve housed within the base plate and configured to close a fluid outlet of the base plate when the base plate is removed from the toothbrush and configured to open when the base plate is connected to the toothbrush.

10. The toothbrush of claim 9 further comprising a charging port cavity that is exposed upon removal of the base plate for receipt of an inductive charging post.

11. The toothbrush of claim 1 further comprising a charging port cavity for receipt of an inductive charging post.

12. The toothbrush of claim 1, wherein the portion of the fluid passage formed within the drive assembly is a cavity defined by one or more components of the drive assembly, wherein the cavity is in fluid communication with the fluid source external to the toothbrush and the fluid conduit in the brush tip.

13. The toothbrush of claim 1, wherein the drive assembly further comprises a rocker arm, wherein the rocker arm defines a cavity that forms the portion of the fluid passage that provides fluid communication between the fluid conduit in the brush tip and the fluid source external to the toothbrush.

14. The toothbrush of claim 1, wherein the drive assembly comprises one or more linkage components, wherein at least one of the linkage components defines a flow lumen defining the portion of the fluid passage that provides fluid communication between the fluid conduit in the brush tip and the fluid source external to the toothbrush.

15. A toothbrush with combined sonic brushing and water flossing attributes, comprising
an electric motor including a drive shaft, wherein, when the electric motor is caused to operate, the drive shaft continuously rotates in a single direction;
a brush tip supporting a brush head on a distal end and defining a fluid conduit therein;
a drive assembly coupled between the drive shaft and the brush tip and configured to convert rotation of the drive shaft into sonic oscillation of the brush head whereby the brush tip pivots back and forth about a longitudinal axis of the brush tip, wherein the drive assembly comprises
a coupler having a first end and a second end, and
an eccentric cam connected to the drive shaft;
a rocker arm that mechanically connects the coupler to the brush tip; wherein
the first end of the coupler is operably coupled to the brush tip and the eccentric cam is rotationally received within the second end of the coupler;
rotation of the drive shaft causes the eccentric cam to rotate within the second end; and
rotation of the eccentric cam causes the coupler to oscillate; and
a fluid passage configured to transport fluid from a fluid source external to the toothbrush to the fluid conduit in the brush tip, wherein a portion of the fluid passage is formed within the drive assembly, wherein the rocker arm further defines a cavity which forms the portion of the fluid passage that provides fluid communication between the fluid conduit in the brush tip and the fluid source external to the toothbrush.

16. The toothbrush of claim 15 further comprising
a brush shaft fixed at a first end to the rocker arm and defining a lumen from the first end to a second end; and
a fluid tube connected to the rocker arm and forming part of the fluid passage; wherein
the brush tip receives the second end of the brush shaft therein;
the lumen of the brush shaft is in fluid communication with the fluid conduit in the brush tip and the cavity in the rocker arm; and
the fluid tube is in fluid communication with the cavity within the rocker arm and thereby the fluid conduit in the brush tip.

17. The toothbrush of claim 16, wherein the brush tip is removably connected to the brush shaft.

18. A toothbrush with combined sonic brushing and water flossing attributes comprising
- an electric motor including a drive shaft, wherein, when the electric motor is caused to operate, the drive shaft continuously rotates in a single direction;
- a brush tip supporting a brush head on a distal end and defining a fluid conduit therein;
- a drive assembly coupled between the drive shaft and the brush tip and configured to convert rotation of the drive shaft into sonic oscillation of the brush head whereby the brush tip pivots back and forth about a longitudinal axis of the brush tip;
- a fluid passage configured to transport fluid from a fluid source external to the toothbrush to the fluid conduit in the brush tip;
- a removable base plate comprising a fluid inlet in fluid communication with the fluid passage and configured for connection with the fluid source; and
- a first valve positioned within the fluid passage and configured to close the fluid passage when the base plate is removed from the toothbrush and configured to open when the base plate is connected to the toothbrush.

19. The toothbrush of claim 18 further comprising a charging port cavity that is exposed upon removal of the base plate for receipt of an inductive charging post.

20. The toothbrush of claim 18 further comprising a second valve housed within the base plate and configured to close a fluid outlet of the base plate when the base plate is removed from the toothbrush and configured to open when the base plate is connected to the toothbrush.

21. The toothbrush of claim 20 wherein the first valve and the second valve interfaces with each other to reciprocally open each other when the base plate is attached to the toothbrush.

22. The toothbrush of claim 20 further comprising
- a charging port cavity that is exposed upon removal of the base plate for receipt of an inductive charging post; wherein
- the second valve is positioned within the charging port cavity;
- and the charging port cavity forms part of the fluid passage.

* * * * *